US006297239B1

(12) United States Patent
deSolms et al.

(10) Patent No.: US 6,297,239 B1
(45) Date of Patent: Oct. 2, 2001

(54) INHIBITORS OF PRENYL-PROTEIN TRANSFERASE

(75) Inventors: S. Jane deSolms, Norristown; John H. Hutchinson, Philadelphia; Anthony W. Shaw, Lansdale; Samuel L. Graham, Schwenksville; Terrence M. Ciccarone, Telford, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/167,180

(22) Filed: Oct. 6, 1998

Related U.S. Application Data

(60) Provisional application No. 60/062,660, filed on Oct. 8, 1997.

(51) Int. Cl.$^7$ ................. A61K 31/4174; A61K 31/5377; C07D 233/61; C07D 413/06
(52) U.S. Cl. ................. 514/235.8; 514/399; 544/122; 548/335.1; 548/336.1; 548/346.1
(58) Field of Search ................. 544/122; 548/335.5, 548/336.1, 346.1; 514/235.8, 399

(56) References Cited

U.S. PATENT DOCUMENTS

| | | | |
|---|---|---|---|
| 3,769,422 | 10/1973 | Timmler et al. | 424/273 |
| 4,006,243 | 2/1977 | Strehlke et al. | 424/273 |
| 4,916,144 | 4/1990 | Strehlke et al. | 514/326 |
| 5,155,118 | * 10/1992 | Carini et al. | 514/381 |
| 5,210,079 | * 5/1993 | Carini et al. | 514/94 |
| 5,710,171 | 1/1998 | Dinsmore et al. | 514/396 |
| 5,756,528 | 5/1998 | Anthony et al. | 514/399 |
| 5,780,488 | 7/1998 | Bergman et al. | 514/357 |
| 5,780,492 | 7/1998 | Dinsmore et al. | 514/397 |

FOREIGN PATENT DOCUMENTS

| | | |
|---|---|---|
| 2 842 759 A1 | 4/1980 | (DE) . |
| 0 050 298 A2 | 4/1982 | (EP) . |
| 0 131 845 | 9/1987 | (EP) . |
| 0 236 913 | 9/1987 | (EP) . |
| 0 289 919 A2 | 11/1988 | (EP) . |
| 0 445 073 A1 | 9/1991 | (EP) . |
| 0 600 315 A1 | 6/1994 | (EP) . |
| 0 633 252 A1 | 1/1995 | (EP) . |
| 0 684 235 A1 | 11/1995 | (EP) . |
| 0 782 852 A1 | 7/1997 | (EP) . |
| 1 469 617 | 4/1977 | (GB) . |
| 1 476 106 | 6/1977 | (GB) . |
| 2 026 159 A | 1/1980 | (GB) . |
| 2 130 584 A | 6/1984 | (GB) . |
| 62-187403 | 8/1987 | (JP) . |
| 08-059638 | 3/1996 | (JP) . |
| WO 96/37204 | 11/1996 | (WO) . |

OTHER PUBLICATIONS

Gibbs, J.B. et al., "Selective Inhibition of Farnesyl–Protein Transferase Blocks Ras Processing in Vivo," The Journal of Biological Chemistry, vol. 268, No. 11, pp. 7617–7620 (1993).

Graham, S.L. and Williams, Theresa M., "Inhibitors of protein franesylation," Exp. Opin. Ther. Patents, vol. 6 (12), pp. 1295–1304 (1996).

Graham, S.L., "Inhibitors of protein farnesylation: a new approach to cancer chemotherapy," Exp. Opin. Ther. Patents, vol. 5, (12), pp. 1269–1285 (1995).

Goldstein, J.L. et al., "Nonfarnesylated Tetrapeptide Inhibitors of Protein Farnesyltransferase," The Journal of Biological Chemistry, vol. 266, No. 24, pp. 15575–15578 (1991).

James, G.L. et al., "Benzodiazepine Peptidomimetic BZA–5B Interrupts the MAP Kinase Activation Pathway in H–Ras–transformed Rat–1 Cells, but Not in Untransformed Cells," The Jour. of Biol. Chem., vol. 269, No. 44, pp. 27705–27714 (1994).

James, G.L., et al., "Polylysine and CVIM Sequences of K–RasB Dictate Specificity of Prenylation and Confer Resistance to Benzodiazepine Peptidomimetic in Vitro", The Jour. of Biol. Chem., vol. 270, No. 11, pp. 6221–6226 (1995).

Kohl, N.E., et al., "Inhibition of farnesyltransferase induces regression of mammary and salivary carcinomas in ras transgenic mice," Nature Medicine, vol. 1, No. 8, pp. 792–797 (1995).

Kohl, N.E. et al., "Protein farnesyltransferase inhibitors block the growth of ras–dependent tumors in nude mice", Proc. Natl. Acad. Sci. USA, Med. Sciences, vol. 91, pp. 9141–9145 (1994).

Kohl, N.E. et al., "Selective Inhibition of ras–Dependent Transformation by a Farnesyltransferase Inhibitor", Science, vol. 260, pp. 1934–1937 (1993).

Pompliano, D.L., "Steady–State Kinetic Mechanism of Ras Farnesyl:Protein Transferase," Biochemistry, vol. 31, pp. 3800–3807 (1992).

Sepp–Lorenzino, L., et al., "A Peptidomimetic Inhibitor of Farnesyl:Protein Transferase Blocks the Anchorage–dependent and –independent Growth of Human Tumor Cell Lines," Cancer Research, vol. 55, pp. 5302–5309 (1995).

Sebolt–Leopold, J.S. et al., "Inhibition of ras farnesyltransferase by a novel class of peptides containing no cysteine or thiol moieties," Proc. Am. Assoc. Cancer Res., vol. 35, No. 3535, p. 593 (1994).

O–Yang, C. et al., "New Approaches to the Preparation of 1–Substituted 1,3–Dihydroimidazole–2–thione Derivatives: Thionation of Imidazoles," Synlett, vol. 6, p.655–658 (1995).

* cited by examiner

Primary Examiner—Fiona T. Powers
(74) Attorney, Agent, or Firm—Dianne Brown; Mark R. Daniel

(57) ABSTRACT

The present invention is directed to compounds which inhibit a prenyl-protein transferase (FTase) and the farnesylation of the oncogene protein Ras. The invention is further directed to chemotherapeutic compositions containing the compounds of this invention and methods for inhibiting a prenyl-protein transferase and the prenylation of the oncogene protein Ras.

31 Claims, No Drawings

INHIBITORS OF PRENYL-PROTEIN TRANSFERASE

DOMESTIC PRIORITY CLAIM

The priority of U.S. Provisional Application No. 60/062,660, filed Oct. 8, 1997, is claimed.

BACKGROUND OF THE INVENTION

The Ras proteins (Ha-Ras, Ki4a-Ras, Ki4b-Ras and N-Ras) are part of a signaling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. Such enzymes may be generally termed prenyl-protein transferase. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop compounds that inhibit prenyl-protein transferase and thus, the post-translational isoprenylation of proteins. It is a further object of this invention to develop chemotherapeutic compositions containing the compounds of this invention and methods for producing the compounds of this invention.

SUMMARY OF THE INVENTION

The present invention comprises small molecule phenyl-containing compounds which inhibit a prenyl-protein transferase. Further contained in this invention are chemotherapeutic compositions containing these prenyl transferase inhibitors and methods for their production.

The compounds of this invention are illustrated by the formula A:

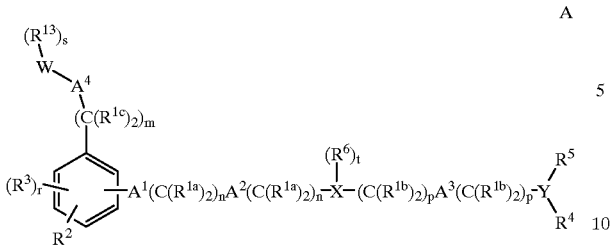

DETAILED DESCRIPTION OF THE INVENTION

The compounds of this invention are useful in the inhibition of prenyl-protein transferase and the prenylation of the oncogene protein Ras. In a first embodiment of this invention, the inhibitors of prenyl-protein transferase are illustrated by the formula A:

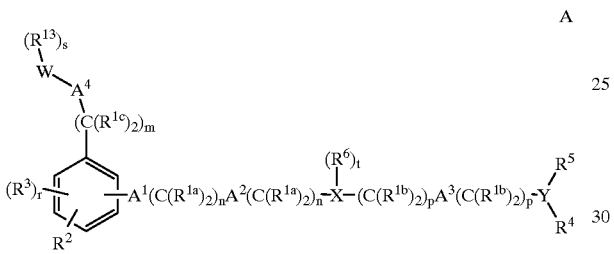

wherein:

$R^{1a}$, $R^{1b}$ and $R^{1c}$ are independently selected from:
a) hydrogen,
b) unsubstituted or substituted aryl, unsubstituted or substituted heterocycle, $C_3-C_{10}$ cycloalkyl, $C_2-C_6$ alkenyl, $C_2-C_6$ alkynyl, $R^8O-$, $R^9S(O)_q-$, CN, $NO_2$, $R^8C(O)-$, $R^8OC(O)-$, $R^8(C_1-C_6$ alkyl)O—, $N_3$, $N(R^8)_2$ or —OC(O)O-heteroaralkyl;
c) $C_1-C_6$ alkyl, unsubstituted or substituted by aryl, heterocyclic, $C_3-C_{10}$ cycloalkyl, $C_2-C_6$ alkenyl, $C_2-C_6$ alkynyl, $R^8O-$, $R^9S(O)_q-$, CN, $R^8C(O)-$, $R^8OC(O)-$, $N_3$, or $R^8C(O)O-$;

$R^2$ is selected from:
a) hydrogen,
b) CN,
c) $NO_2$,
d) halogen,
e) aryl, unsubstituted or substituted
f) heteroaryl, unsubstituted or substituted
g) $C_1-C_6$ alkyl, unsubstituted or substituted
h) $N_3$,
i) $R^9S(O)_q$,
j) $R^8HC=CH-$,
k) $R^8C\equiv C-$, and
l) $OR^8$;

$R^3$, $R^4$ and $R^5$ are independently selected from:
H, CN, $NO_2$, halogen, unsubstituted or substituted $C_1-C_6$ alkyl, $N_3$, $R^9S(O)_q$, $HC\equiv C-$, unsubstituted or substituted aryl, unsubstituted or substituted heterocycle, $CF_3$, $CF_3O-$, $CF_3CH_2O-$, $C_3-C_{10}$ cycloalkyl, $OR^8$, $N(R^8)_2$, $-C(O)R^8$, $-O(C_1-C_6$ alkyl)$OR^8$, $-NHC(O)R^8$, aralkyl, heteroaralkyl, $-(C_1-C_6$ alkyl)$OR^8$, $-(C_1-C_6$ alkyl)$C(O)R^8$, $-CH=CH-R^8$ and

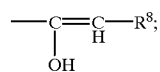

$R^6$ is independently selected from:
a) hydrogen,
b) CN,
c) $NO_2$,
d) halogen,
e) aryl, unsubstituted or substituted,
f) heteroaryl, unsubstituted or substituted,
g) $C_1-C_6$ alkyl, unsubstituted or substituted,
h) $R^8O-$,
i) $N_3$,
j) $R^9S(O)_q-$,
k) $-HC=CH_2$,
l) $-C\equiv CH$,
m) $CF_3$
n) $R^8O(C=O)-$, and
o) $R^8$ (O=C)O—;

$R^8$ is independently selected from
hydrogen, unsubstituted or substituted $C_1-C_6$ alkyl, cycloalkyl, benzyl and unsubstituted or substituted aryl;

$R^9$ is independently selected from
H, unsubstituted or substituted $C_1-C_6$ alkyl, benzyl and unsubstituted or substituted aryl;

$R^{13}$ is independently selected from
H, unsubstituted or substituted $C_1-C_6$ alkyl, unsubstituted or substituted aryl, unsubstituted or substituted heterocycle, $-(C_1-C_6$ alkyl)$OR^8$, $-(C_1-C_6$ alkyl)$OC(O)(C_1-C_6$ alkyl), $-(C_1-C_6$ alkyl)$N(R^8)_2$, and $-(C_1-C_6$ alkyl)$NHC(O)(C_1-C_6$ alkyl)$R^8$;

$A^1$, $A^2$ and $A^3$ are independently selected from:
a) a bond,
b) $-HC=CH-$,
c) $-C\equiv C-$,
d) $-O-$,
e) $-(C=O)-$,
f) $-O(C=O)-$,
g) $-(C=O)O-$,
h) $-NR^8-$,
i) $-C(O)N(R^8)-$,
j) $-N(R^8)C(O)-$,
k) $-NHC(O)NH-$,
l) $-S(O)_q-$,
m) $-S(O)_qNH-$, and
n) $-NHS(O)_q-$;

$A^4$ is selected from a bond, C(O), $C=CH_2$, or spiro $C_3-C_6$ cycloalkyl;

W is selected from:
a) hydrogen,
b) heterocycle, and
c) aryl;

X is selected from:
a) aryl,
b) cycloalkyl,
c) heterocycle, and
d) a bond;

Y is selected from:
a) aryl, unsubstituted or substituted
b) heterocycle, unsubstituted or substituted, and
c) cycloalkyl;

m is 0, 1, 2, 3 or 4;

n is 0, 1, 2, 3 or 4;
p is 0, 1, 2, 3 or 4;
q is 0, 1 or 2;
r is 0, 1, 2 or 3;
s is 0, 1, 2, 3 or 4; and;
t is 0, 1, 2 or 3;
provided that

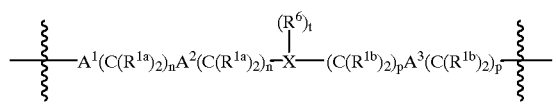

is not a bond;
or the pharmaceutically acceptable salts thereof.

In a further embodiment of this invention, the inhibitors of a prenyl-protein transferase are illustrated by the formula A:

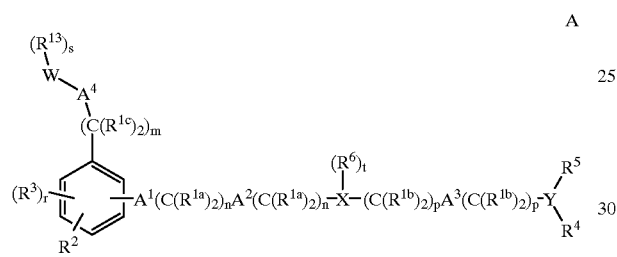

wherein:

$R^{1a}$, $R^{1b}$ and $R^{1c}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $R^8(C_1$–$C_6$ alkyl)O—, $N_3$, $N(R^8)_2$ or —OC(O)O-heteroaralkyl;
  c) $C_1$–$C_6$ alkyl, unsubstituted or substituted by aryl, heterocyclic, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N_3$, or $R^8C(O)O$—;

$R^2$ is selected from:
  a) hydrogen,
  b) CN,
  c) $NO_2$,
  d) halogen,
  e) aryl, unsubstituted or substituted
  f) heteroaryl, unsubstituted or substituted
  g) $C_1$–$C_6$ alkyl, unsubstituted or substituted
  h) $N_3$,
  i) $R^9S(O)_q$,
  j) $R^8HC$=C—,
  k) $R^8C$≡C—, and
  l) $OR^8$;

$R^3$, $R^4$ and $R^5$ are independently selected from:
  H, CN, $NO_2$, halogen, unsubstituted or substituted $C_1$–$C_6$ alkyl, $N_3$, $R^9S(O)_q$, —C≡CH, unsubstituted or substituted aryl, unsubstituted or substituted heterocycle, $CF_3$, $CF_3O$—, $CF_3CH_2O$—, $C_3$–$C_{10}$ cycloalkyl, $OR^8$, $N(R^8)_2$, —C(O)$R^8$, —O($C_1$–$C_6$ alkyl)$OR^8$, —NHC(O)$R^8$, aralkyl, heteroaralkyl, —($C_1$–$C_6$ alkyl)C(O)$R^8$, —CH=CH—$R^8$ and

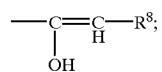

$R^6$ is independently selected from:
  a) hydrogen,
  b) CN,
  c) $NO_2$,
  d) halogen,
  e) aryl, unsubstituted or substituted,
  f) heteroaryl, unsubstituted or substituted,
  g) $C_1$–$C_6$ alkyl, unsubstituted or substituted,
  h) $R^8O$—, unsubstituted or substituted,
  i) $N_3$,
  j) $R^9S(O)_q$—,
  k) —HC=$CH_2$,
  l) —C≡CH,
  m) $CF_3$
  n) $R^8O(C$=O)—, and
  o) $R^8$ (O=C)O—;

$R^8$ is independently selected from
  hydrogen, unsubstituted or substituted $C_1$–$C_6$ alkyl, cycloalkyl, benzyl and unsubstituted or substituted aryl;

$R^9$ is independently selected from
  H, unsubstituted or substituted $C_1$–$C_6$ alkyl, benzyl and unsubstituted or substituted aryl;

$R^{13}$ is independently selected from
  H, unsubstituted or substituted $C_1$–$C_6$ alkyl, unsubstituted or substituted aryl, unsubstituted or substituted heterocycle, —($C_1$–$C_6$ alkyl)$OR^8$, —($C_1$–$C_6$ alkyl)OC(O)($C_1$–$C_6$ alkyl), —($C_1$–$C_6$ alkyl)N($R^8)_2$, and —($C_1$–$C_6$ alkyl)NHC(O)($C_1$–$C_6$ alkyl)$R^8$;

$A^1$, $A^2$ and $A^3$ are independently selected from:
  a) a bond,
  b) —HC=CH—,
  c) —C=C—,
  d) —O—,
  e) —(C=O)—,
  f) —O(C=O)—,
  g) —(C=O)O—,
  h) —$NR^8$—,
  i) —C(O)N($R^8$)—,
  j) —N($R^8$)C(O)—,
  k) —NHC(O)NH—,
  l) —S(O)$_q$—,
  m) —S(O)$_q$NH—, and
  n) —NHS(O)$_q$—;

$A^4$ is selected from a bond, C(O), C=$CH_2$, or spiro $C_3$–$C_6$ cycloalkyl;

W is selected from:
  a) heterocycle, and
  b) aryl;

X is selected from:
  a) aryl,
  b) cycloalkyl,
  c) heterocycle, and
  d) a bond;

Y is selected from:
  a) aryl,
  b) heterocycle, and
  c) cycloalkyl;

m is 0, 1, 2, 3 or 4;
n is 0, 1, 2, 3 or 4;

p is 0, 1, 2, 3 or 4;
q is 0, 1 or 2;
r is 1 or 2;
s is 0, 1, 2, 3 or 4; and
t is 0, 1, 2 or 3;
provided that

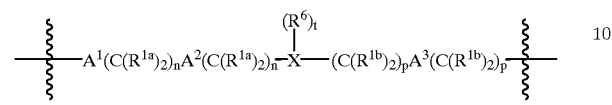

is not a bond;
or the pharmaceutically acceptable salts thereof.

In another embodiment of the instant invention, the inhibitors of a prenyl-protein transferase are illustrated by formula B:

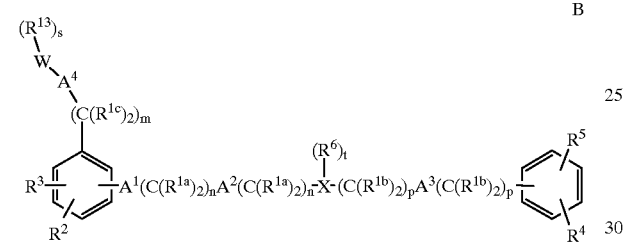

wherein:

$R^{1a}$, $R^{1b}$ and $R^{1c}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $R^8(C_1$–$C_6$ alkyl)O—, $N_3$, $N(R^8)_2$ or —OC(O)O-heteroaralkyl;
  c) $C_1$–$C_6$ alkyl, unsubstituted or substituted by aryl, heterocyclic, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N_3$, or $R^8C(O)O$—;

$R^2$ is selected from:
  a) hydrogen,
  b) CN,
  c) $NO_2$,
  d) halogen,
  e) aryl, unsubstituted or substituted
  f) heteroaryl, unsubstituted or substituted
  g) $C_1$–$C_6$ alkyl, unsubstituted or substituted
  h) $N_3$,
  i) $R^9S(O)_q$,
  j) $R^8HC$=CH—,
  k) $R^8C$≡C—, and
  l) $OR^8$;

$R^3$, $R^4$ and $R^5$ are independently selected from:
  H, CN, $NO_2$, halogen, unsubstituted or substituted $C_1$–$C_6$ alkyl, $N_3$, $R^9S(O)_q$, HC≡C—, unsubstituted or substituted aryl, unsubstituted or substituted heterocycle, $CF_3$, $CF_3O$—, $CF_3CH_2O$—, $C_3$–$C_{10}$ cycloalkyl, $OR^8$, $N(R^8)_2$, —$C(O)R^8$, —$O(C_1$–$C_6$ alkyl)$OR^8$, —$NHC(O)R^8$, aralkyl, heteroaralkyl, —$(C_1$–$C_6$ alkyl)$OR^8$, —$(C_1$–$C_6$ alkyl)$C(O)R^8$, —CH=CH—$R^8$ and

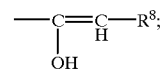

$R^6$ is independently selected from:
  a) hydrogen,
  b) CN,
  c) $NO_2$,
  d) halogen,
  e) aryl, unsubstituted or substituted,
  f) heteroaryl, unsubstituted or substituted,
  g) $C_1$–$C_6$ alkyl, unsubstituted or substituted,
  h) $R^8O$—,
  i) $N_3$,
  j) $R^9S(O)_q$—,
  k) —HC=$CH_2$,
  l) —C≡CH,
  m) $CF_3$
  n) $R^8O(C$=O)—, and
  o) $R^8$ (O=C)O—;

$R^8$ is independently selected from
  hydrogen, unsubstituted or substituted $C_1$–$C_6$ alkyl, cycloalkyl, benzyl and unsubstituted or substituted aryl;

$R^9$ is independently selected from
  H, unsubstituted or substituted $C_1$–$C_6$ alkyl, benzyl and unsubstituted or substituted aryl;

$R^{13}$ is independently selected from
  H, unsubstituted or substituted $C_1$–$C_6$ alkyl, unsubstituted or substituted aryl, unsubstituted or substituted heterocycle, —$(C_1$–$C_6$ alkyl)$OR^8$, —$(C_1$–$C_6$ alkyl)$OC(O)(C_1$–$C_6$ alkyl), —$(C_1$–$C_6$ alkyl)$N(R^8)_2$, and —$(C_1$–$C_6$ alkyl)$NHC(O)(C_1$–$C_6$ alkyl)$R^8$;

$A^1$, $A^2$ and $A^3$ are independently selected from:
  a) a bond,
  b) —HC=CH—,
  c) —C≡C—,
  d) —O—,
  e) —(C=O)—,
  f) —O(C=O)—,
  g) —(C=O)O—,
  h) —$NR^8$—,
  i) —C(O)N($R^8$)—,
  j) —N($R^8$)C(O)—,
  k) —NHC(O)NH—,
  l) —S(O)$_q$—,
  m) —S(O)$_q$NH—, and
  n) —NHS(O)$_q$—;

$A^4$ is selected from a bond, C(O), C=$CH_2$, or spiro $C_3$–$C_6$ cycloalkyl;

W is selected from:
  a) heterocycle, and
  b) aryl;

X is selected from:
  a) aryl,
  b) cycloalkyl,
  c) heterocycle, and
  d) a bond;

m is 0, 1, 2, 3 or 4;
n is 0, 1, 2, 3 or 4;
p is 0, 1, 2, 3 or 4;
q is 0, 1 or 2;
s is 0, 1, 2, 3 or 4; and
t is 0, 1, 2, or 3;

provided that

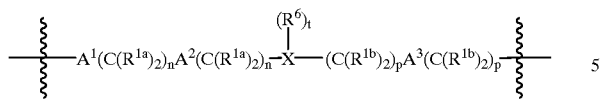

is not a bond;
or the pharmaceutically acceptable salts thereof.

In further embodiment of the instant invention, the inhibitors of a prenyl-protein transferase are illustrated by formula B:

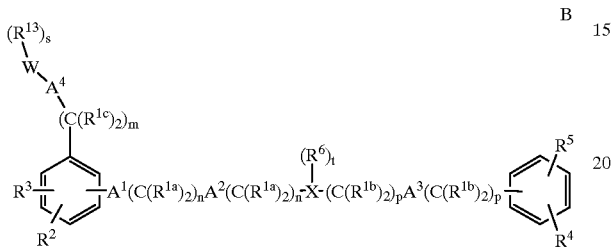

wherein:
$R^{1a}$, $R^{1b}$ and $R^{1c}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $R^8(C_1$–$C_6$ alkyl)O—, $N_3$, $N(R^8)_2$ or —OC(O)O-heteroaralkyl;
c) $C_1$–$C_6$ alkyl, unsubstituted or substituted by aryl, heterocyclic, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N_3$, or $R^8C(O)O$—;

$R^2$ is selected from:
a) hydrogen,
b) CN,
c) $NO_2$,
d) halogen,
e) aryl, unsubstituted or substituted
f) heteroaryl, unsubstituted or substituted
g) $C_1$–$C_6$ alkyl, unsubstituted or substituted
h) $N_3$,
i) $R^9S(O)_q$,
j) $R^8HC=CH$—,
k) $R^8C\equiv C$, and
l) $OR^8$;

$R^3$, $R^4$ and $R^5$ are independently selected from:
H, CN, $NO_2$, halogen, unsubstituted or substituted $C_1$–$C_6$ alkyl, $N_3$, $R^9S(O)_q$, $HC\equiv C$—, unsubstituted or substituted aryl, unsubstituted or substituted heterocycle, $CF_3$, $CF_3O$—, $CF_3CH_2O$—, $C_3$–$C_{10}$ cycloalkyl, $OR^8$, $N(R^8)_2$, —C(O)$R^8$, —O($C_1$–$C_6$ alkyl)$OR^8$, —NHC(O)$R^8$, aralkyl, heteroaralkyl, —($C_1$–$C_6$ alkyl)$OR^8$, —($C_1$–$C_6$ alkyl)C(O)$R^8$, —CH=CH—$R^8$ and

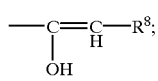

$R^6$ is independently selected from:
a) hydrogen,
b) CN,
c) $NO_2$,
d) halogen,
e) aryl, unsubstituted or substituted,
f) heteroaryl, unsubstituted or substituted,
g) $C_1$–$C_6$ alkyl, unsubstituted or substituted,
h) $R^8O$—,
i) $N_3$,
j) $R^9S(O)_q$—,
k) —HC=$CH_2$,
l) —C$\equiv$CH,
m) $CF_3$
n) $R^8O(C=O)$—, and
o) $R^8$ (O=C)O—;

$R^8$ is independently selected from
hydrogen, unsubstituted or substituted $C_1$–$C_6$ alkyl, cycloalkyl, benzyl and unsubstituted or substituted aryl;

$R^9$ is independently selected from
H, unsubstituted or substituted $C_1$–$C_6$ alkyl, benzyl and unsubstituted or substituted aryl;

$R^{13}$ is independently selected from
H, unsubstituted or substituted $C_1$–$C_6$ alkyl, unsubstituted or substituted aryl, unsubstituted or substituted heterocycle, —($C_1$–$C_6$ alkyl)$OR^8$, —($C_1$–$C_6$ alkyl)OC(O)($C_1$–$C_6$ alkyl), —($C_1$–$C_6$ alkyl)N($R^8)_2$, and —($C_1$–$C_6$ alkyl)NHC(O)($C_1$–$C_6$ alkyl)$R^8$;

$A^1$ is selected from:
a) a bond,
b) —O—,
c) —(C=O)—,
d) —$NR^8$—,
e) —C(O)N($R^8$)—, and
f) —S(O)$_q$—;

$A^2$ and $A^3$ are independently selected from:
a) a bond,
b) —HC=CH—,
c) —C$\equiv$C—,
d) —O—,
e) —(C=O)—,
f) —O(C=O)—,
g) —(C=O)O—,
h) —$NR^8$—,
i) —C(O)N($R^8$)—,
j) —N($R^8$)C(O)—,
k) —NHC(O)NH—,
l) —S(O)$_q$—,
m) —S(O)$_q$NH—, and
n) —NHS(O)$_q$—;

$A^4$ is selected from a bond, C(O), C=$CH_2$, or spiro $C_3$–$C_6$ cycloalkyl;

W is a heterocycle,

X is selected from:
a) aryl,
b) heterocycle, and
c) a bond;

m is 0, 1, 2, 3 or 4;
n is 0, 1, 2, 3 or 4;
p is 0, 1, 2, 3 or 4;
q is 0, 1 or 2;
s is 0, 1, 2, 3 or 4; and
t is 0, 1, 2 or 3;

provided that

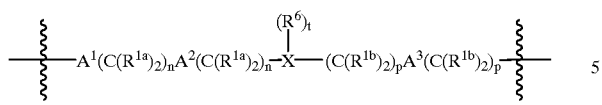

is not a bond;
or the pharmaceutically acceptable salts thereof.

In another embodiment of the instant invention, the inhibitors of a prenyl-protein transferase are illustrated by the formula C:

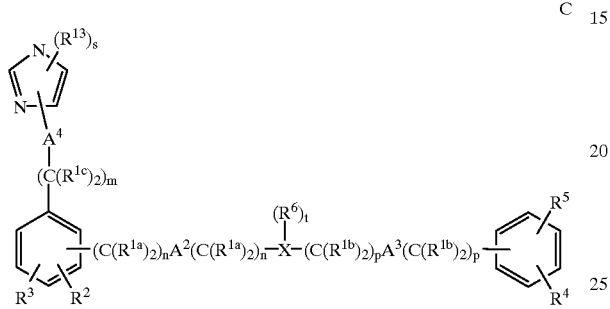

wherein:
$R^{1a}$, $R^{1b}$ and $R^{1c}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $R^8(C_1$–$C_6$ alkyl)O—, $N_3$, $N(R^8)_2$ or —OC(O)O-heteroaralkyl;
  c) $C_1$–$C_6$ alkyl, unsubstituted or substituted by aryl, heterocyclic, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N_3$, or $R^8C(O)O$—;

$R^2$ is selected from:
  a) hydrogen,
  b) CN,
  c) $NO_2$,
  d) halogen,
  e) aryl, unsubstituted or substituted
  f) heteroaryl, unsubstituted or substituted
  g) $C_1$–$C_6$ alkyl, unsubstituted or substituted
  h) $R^9S(O)_q$, and
  i) $OR^8$;

$R^3$, $R^4$ and $R^5$ are independently selected from:
  H, CN, $NO_2$, halogen, unsubstituted or substituted $C_1$–$C_6$ alkyl, $N_3$, $R^9S(O)_q$, HC≡C—, unsubstituted or substituted aryl, unsubstituted or substituted heterocycle, $CF_3$, $CF_3O$—, $CF_3CH_2O$—, $C_3$–$C_{10}$ cycloalkyl, $OR^8$, $N(R^8)_2$, —$C(O)R^8$, —$O(C_1$–$C_6$ alkyl)$OR^8$, —$NHC(O)R^8$, aralkyl, heteroaralkyl, —$(C_1$–$C_6$ alkyl)$OR^8$, —$(C_1$–$C_6$ alkyl)$C(O)R^8$, —CH=CH—$R^8$ and

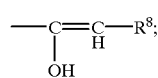

$R^6$ is independently selected from:
  a) hydrogen,
  b) CN,
  c) $NO_2$,
  d) halogen,
  e) aryl, unsubstituted or substituted,
  f) heteroaryl, unsubstituted or substituted,
  g) $C_1$–$C_6$ alkyl, unsubstituted or substituted,
  h) $R^8O$—,
  i) $N_3$,
  j) $R^9S(O)_q$—,
  k) $CF_3$
  l) $R^8O(C=O)$—, and
  m) $R^8$ (O=C)O—;

$R^8$ is independently selected from
  hydrogen, unsubstituted or substituted $C_1$–$C_6$ alkyl, cycloalkyl, benzyl and unsubstituted or substituted aryl;

$R^9$ is independently selected from
  H, unsubstituted or substituted $C_1$–$C_6$ alkyl, benzyl and unsubstituted or substituted aryl;

$R^{13}$ is independently selected from
  H, unsubstituted or substituted $C_1$–$C_6$ alkyl, unsubstituted or substituted aryl, unsubstituted or substituted heterocycle, —$(C_1$–$C_6$ alkyl)$OR^8$, —$(C_1$–$C_6$ alkyl)$OC(O)(C_1$–$C_6$ alkyl), —$(C_1$–$C_6$ alkyl)$N(R^8)_2$, and —$(C_1$–$C_6$ alkyl)$NHC(O)(C_1$–$C_6$ alkyl)$R^8$;

$A^2$ is selected from:
  a) a bond,
  b) —HC=CH—,
  c) —C≡C—,
  d) —O—,
  e) —(C=O)—,
  f) —O(C=O)—,
  g) —(C=O)O—,
  h) —$NR^8$—,
  i) —$C(O)N(R^8)$—,
  j) —$N(R^8)C(O)$—,
  k) —NHC(O)NH—,
  l) —$S(O)_q$,
  m) —$S(O)_qNH$—, and
  n) $NHS(O)_q$—;

$A^3$ is selected from:
  a) a bond,
  b) —O—,
  c) —$S(O)_q$—,
  d) —$S(O)_qNH$—,
  e) —$NR^8$—,
  f) —(C=O)—,
  g) —(C=O)O—,
  h) —O(C=O)—,
  i) —$C(O)N(R^8)$—,
  j) —$N(R^8)C(O)$—, and
  k) —NHC(O)NH—;

$A^4$ is selected from a bond, C(O), C=$CH_2$, or spiro $C_3$–$C_6$ cycloalkyl;

X is selected from:
  a) aryl,
  b) heterocycle, and
  c) a bond;

m is 0, 1, 2, 3 or 4;
n is 0, 1, 2, 3 or 4;
p is 0, 1, 2, 3 or 4;
q is 0, 1 or 2;
s is 0, 1, 2, 3 or 4; and
t is 0, 1, 2 or 3;

provided that

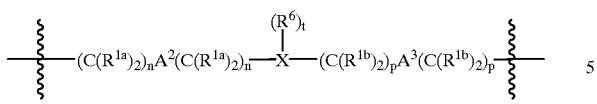

is not a bond;
or the pharmaceutically acceptable salts thereof.

In another embodiment of the instant invention, the inhibitors of a prenyl-protein transferase are illustrated by the formula D:

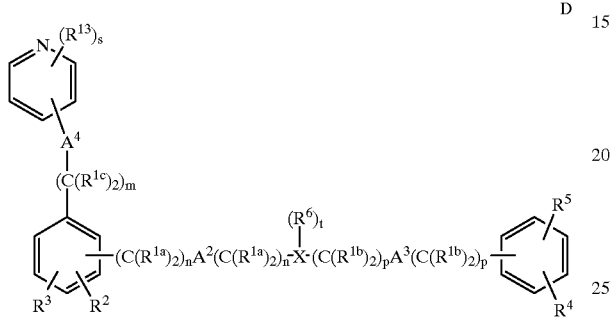

wherein:
$R^{1a}$, $R^{1b}$ and $R^{1c}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $R^8(C_1$–$C_6$ alkyl)O—, $N_3$, $N(R^8)_2$ or —OC(O)O-heteroaralkyl;
  c) $C_1$–$C_6$ alkyl, unsubstituted or substituted by aryl, heterocyclic, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N_3$, or $R^8C(O)O$—;

$R^2$ is selected from:
  a) hydrogen,
  b) CN,
  c) $NO_2$,
  d) halogen,
  e) aryl, unsubstituted or substituted
  f) heteroaryl, unsubstituted or substituted
  g) $C_1$–$C_6$ alkyl, unsubstituted or substituted
  h) $R^9S(O)_q$, and
  i) $OR^8$;

$R^3$, $R^4$ and $R^5$ are independently selected from:
  H, CN, $NO_2$, halogen, unsubstituted or substituted $C_1$–$C_6$ alkyl, $N_3$, $R^9S(O)_q$, HC≡C—, unsubstituted or substituted aryl, unsubstituted or substituted heterocycle, $CF_3$, $CF_3O$—, $CF_3CH_2O$—, $C_3$–$C_{10}$ cycloalkyl, $OR^8$, $N(R^8)_2$, —$C(O)R^8$, —$O(C_1$–$C_6$ alkyl)$OR^8$, —$NHC(O)R^8$, aralkyl, heteroaralkyl, —($C_1$–$C_6$ alkyl)$OR^8$, —($C_1$–$C_6$ alkyl)$C(O)R^8$, —CH=CH—$R^8$ and

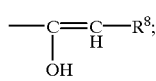

$R^6$ is independently selected from:
  a) hydrogen,
  b) CN,
  c) $NO_2$,
  d) halogen,
  e) aryl, unsubstituted or substituted,
  f) heteroaryl, unsubstituted or substituted,
  g) $C_1$–$C_6$ alkyl, unsubstituted or substituted,
  h) $R^8O$—,
  i) $N_3$,
  j) $R^9S(O)_q$—,
  k) $CF_3$
  l) $R^8O(C=O)$—, and
  m) $R^8(O=C)O$—;

$R^8$ is independently selected from
  hydrogen, unsubstituted or substituted $C_1$–$C_6$ alkyl, cycloalkyl, benzyl and unsubstituted or substituted aryl;

$R^9$ is independently selected from
  H, unsubstituted or substituted $C_1$–$C_6$ alkyl, benzyl and unsubstituted or substituted aryl;

$R^{13}$ is independently selected from
  H, unsubstituted or substituted $C_1$–$C_6$ alkyl, unsubstituted or substituted aryl, unsubstituted or substituted heterocycle, —($C_1$–$C_6$ alkyl)$OR^8$, —($C_1$–$C_6$ alkyl)$OC(O)(C_1$–$C_6$ alkyl), —($C_1$–$C_6$ alkyl)$N(R^8)_2$, and —($C_1$–$C_6$ alkyl)$NHC(O)(C_1$–$C_6$ alkyl)$R^8$;

$A^2$ is selected from:
  a) a bond,
  b) —HC=CH—,
  c) —C≡C—,
  d) —O—,
  e) —(C=O)—,
  f) —O(C=O)—,
  g) —(C=O)O—,
  h) —$NR^8$—,
  i) —$C(O)N(R^8)$—,
  j) —$N(R^8)C(O)$—,
  k) —NHC(O)NH—,
  l) —$S(O)_q$—,
  m) —$S(O)_qNH$—, and
  n) —$NHS(O)_q$—;

$A^3$ is selected from:
  a) a bond,
  b) —O—,
  c) —$S(O)_q$,
  d) —$S(O)_qNH$—,
  e) —$NR^8$—,
  f) —(C=O)—,
  g) —(C=O)O—,
  h) —O(C=O)—,
  i) —$C(O)N(R^8)$—,
  j) —$N(R^8)C(O)$—, and
  k) —NHC(O)NH—;

$A^4$ is selected from a bond, C(O), C=$CH_2$, or spiro $C_3$–$C_6$ cycloalkyl;

X is selected from:
  a) aryl,
  b) heterocycle, and
  c) a bond;

m is 0, 1, 2, 3 or 4;
n is 0, 1, 2, 3 or 4;
p is 0, 1, 2, 3 or 4;
q is 0, 1 or 2; and
s is 0, 1, 2, 3 or 4; and
t is 0, 1, 2, or 3;

provided that

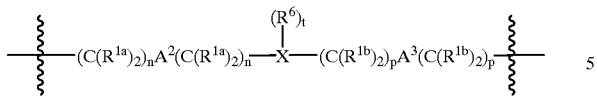

is not a bond;
or the pharmaceutically acceptable salts thereof.

In another embodiment of the instant invention, the inhibitors of a prenyl-protein transferase are illustrated by the formula E:

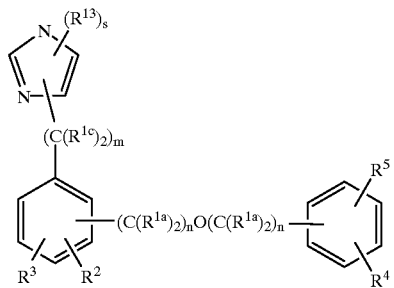

wherein:
$R^{1a}$ and $R^{1c}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $R^8(C_1$–$C_6$ alkyl)O—, $N_3$, $N(R^8)_2$ or —OC(O)O-heteroaralkyl;
  c) $C_1$–$C_6$ alkyl, unsubstituted or substituted by aryl, heterocyclic, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N_3$, or $R^8C(O)O$—;
$R^2$ is selected from:
  a) hydrogen,
  b) CN,
  c) $NO_2$,
  d) halogen,
  e) aryl, unsubstituted or substituted
  f) heteroaryl, unsubstituted or substituted
  g) $C_1$–$C_6$ alkyl, unsubstituted or substituted
  h) $R^9S(O)_q$, and
  i) $OR^8$;
$R^3$, $R^4$ and $R^5$ are independently selected from:
  H, CN, $NO_2$, halogen, unsubstituted or substituted $C_1$–$C_6$ alkyl, $N_3$, $R^9S(O)_q$, HC≡C—, unsubstituted or substituted aryl, unsubstituted or substituted heterocycle, $CF_3$, $CF_3O$—, $CF_3CH_2O$—, $C_3$–$C_{10}$ cycloalkyl, $OR^8$, $N(R^8)_2$, —C(O)$R^8$, —O($C_1$–$C_6$ alkyl)$OR^8$, —NHC(O)$R^8$, aralkyl, heteroaralkyl, —($C_1$–$C_6$ alkyl)$R^8$, —($C_1$–$C_6$ alkyl)C(O)$R^8$, —CH=CH—$R^8$ and

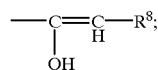

$R^8$ is independently selected from
  hydrogen, unsubstituted or substituted $C_1$–$C_6$ alkyl, cycloalkyl, benzyl and unsubstituted or substituted aryl;

$R^9$ is independently selected from
  H, unsubstituted or substituted $C_1$–$C_6$ alkyl, benzyl and unsubstituted or substituted aryl;
$R^{13}$ is independently selected from
  H, unsubstituted or substituted $C_1$–$C_6$ alkyl, unsubstituted or substituted aryl, unsubstituted or substituted heterocycle, —($C_1$–$C_6$ alkyl)$OR^8$, —($C_1$–$C_6$ alkyl)OC(O)($C_1$–$C_6$ alkyl), —($C_1$–$C_6$ alkyl)N($R^8$)$_2$, and —($C_1$–$C_6$ alkyl)NHC(O)($C_1$–$C_6$ alkyl)$R^8$;
m is 0, 1, 2, 3 or 4;
n is 0, 1, 2, 3 or 4;
q is 0, 1 or 2; and
s is 0, 1, 2, 3 or 4;
or the pharmaceutically acceptable salts thereof.

In another embodiment of the instant invention, the inhibitors of a prenyl-protein transferase are illustrated by the formula F:

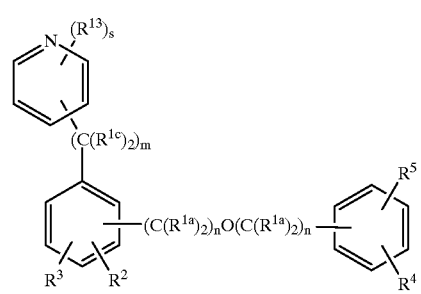

wherein:
$R^{1a}$ and $R^{1c}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $R^8(C_1$–$C_6$ alkyl)O—, $N_3$, $N(R^8)_2$ or —OC(O)O-heteroaralkyl;
  c) $C_1$–$C_6$ alkyl, unsubstituted or substituted by aryl, heterocyclic, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N_3$, or $R^8C(O)O$—;
$R^2$ is selected from:
  a) hydrogen,
  b) CN,
  c) $NO_2$,
  d) halogen,
  e) aryl, unsubstituted or substituted
  f) heteroaryl, unsubstituted or substituted
  g) $C_1$–$C_6$ alkyl, unsubstituted or substituted
  h) $R^9S(O)_q$, and
  i) $OR^8$;
$R^3$, $R^4$ and $R^5$ are independently selected from:
  H, CN, $NO_2$, halogen, unsubstituted or substituted $C_1$–$C_6$ alkyl, $N_3$, $R^9S(O)_q$, HC≡C—, unsubstituted or substituted aryl, unsubstituted or substituted heterocycle, $CF_3$, $CF_3O$—, $CF_3CH_2O$—, $C_3$–$C_{10}$ cycloalkyl, $OR^8$, $N(R^8)_2$, —C(O)$R^8$, —O($C_1$–$C_6$ alkyl)$OR^8$, —NHC(O)$R^8$, aralkyl, heteroaralkyl, —($C_1$–$C_6$ alkyl)$OR^8$, —($C_1$–$C_6$ alkyl)C(O)$R^8$, —CH=CH—$R^8$ and

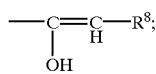

R⁸ is independently selected from
hydrogen, unsubstituted or substituted $C_1$–$C_6$ alkyl, cycloalkyl, benzyl and unsubstituted or substituted aryl;

R⁹ is independently selected from
H, unsubstituted or substituted $C_1$–$C_6$ alkyl, benzyl and unsubstituted or substituted aryl;

R¹³ is independently selected from
H, unsubstituted or substituted $C_1$–$C_6$ alkyl, unsubstituted or substituted aryl, unsubstituted or substituted heterocycle, —($C_1$–$C_6$ alkyl)OR⁸, —($C_1$–$C_6$ alkyl)OC(O)($C_1$–$C_6$ alkyl), —($C_1$–$C_6$ alkyl)N(R⁸)$_2$, and —($C_1$–$C_6$ alkyl)NHC(O)($C_1$–$C_6$ alkyl)R⁸;

m is 0, 1, 2, 3 or 4;
n is 0, 1, 2, 3 or 4;
q is 0, 1 or 2; and
s is 0, 1, 2, 3 or 4;
or the pharmaceutically acceptable salts thereof.

In second embodiment of the instant invention, the inhibitors of a prenyl-protein transferase are illustrated by the formula I:

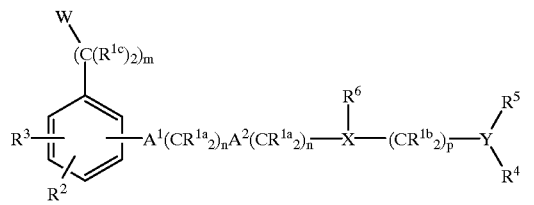

I wherein:
$R^{1a}$, $R^{1b}$ and $R^{1c}$ are independently selected from:
a) hydrogen,
b) unsubstituted or substituted aryl; unsubstituted or substituted heterocycle; unsubstituted or substituted heteroaryl; $C_3$–$C_{10}$ cycloalkyl, $C_2$–$C_6$ alkenyl, $C_2$–$C_6$ alkynyl, R⁸O—, R⁹S(O)$_q$—, CN, NO$_2$, R⁸C(O)—, R⁸OC(O)—, or N$_3$;
c) $C_1$–$C_6$ alkyl, unsubstituted or substituted by aryl, heterocyclic, $C_3$–$C_{10}$ cycloalkyl, $C_2$–$C_6$ alkenyl, $C_2$–$C_6$ alkynyl, R⁸O—, R⁹S(O)$_q$—, CN, R⁸C(O)—, R⁸OC(O)—, N$_3$, or R⁸C(O)O—;

R² is selected from:
a) hydrogen,
b) CN,
c) NO$_2$,
d) halogen,
e) aryl,
f) heteroaryl,
g) $C_1$–$C_6$ alkyl,
h) $C_1$–$C_6$ alkoxy,
i) N$_3$,
j) R⁹S(O)$_q$,
k) R⁸C=C, and
l) R⁸C≡C;

R³, R⁴ and R⁵ are independently selected from:
a) H,
b) CN,
c) NO$_2$,
d) halogen,
e) $C_1$–$C_6$ alkyl,
f) $C_1$–$C_6$ alkoxy,
g) N$_3$,
h) R⁹S(O)$_q$,
i) —HC=CH$_2$,
j) —C≡CH,
k) aryl, unsubstituted or substituted,
l) heterocycle, unsubstituted or substituted,
m) CF$_3$O—,
n) CF$_3$CH$_2$O—,
o) $C_3$–$C_{10}$ cycloalkyl, and
p) CF$_3$;

R⁶ is independently selected from:
a) hydrogen,
b) CN,
c) NO$_2$,
d) halogen,
e) aryl, unsubstituted or substituted,
f) heteroaryl, unsubstituted or substituted,
g) $C_1$–$C_6$ alkyl, unsubstituted or substituted,
h) R⁸O,
i) N$_3$,
j) R⁹S(O)$_q$,
k) —HC=CH$_2$,
l) —C≡CH,
m) CF$_3$
n) R⁸O(C=O), and
o) R⁸ (O=C)O;

R⁸ is independently selected from hydrogen, $C_1$–$C_6$ alkyl, benzyl and aryl;

R⁹ is independently selected from $C_1$–$C_6$ alkyl, benzyl and aryl;

A¹ and A² are independently selected from:
a) a bond,
b) —HC=CH—,
c) —C≡C—,
d) O,
e) S(O)$_q$,
f) O(C=O),
g) (O=C), and
h) (C=O)O;

W is selected from:
a) hydrogen,
b) heterocycle, unsubstituted or substituted, and
c) aryl, unsubstituted or substituted;

X is selected from:
a) aryl,
b) heteroaryl,
c) cycloalkyl,
d) heterocycle, and
e) a bond;

Y is selected from:
a) aryl, unsubstituted or substituted,
b) heterocycle, unsubstituted or substituted, and
c) heteroaryl, unsubstituted or substituted;

m is 0, 1, 2, 3 or 4;
n is 0, 1, 2, 3 or 4;
p is 0, 1, 2, 3 or 4; and
q is 0, 1 or 2;

provided that

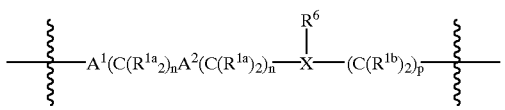

is not a bond;
or the pharmaceutically acceptable salts thereof.

A preferred embodiment of the compounds of this invention are illustrated by the formula Ia:

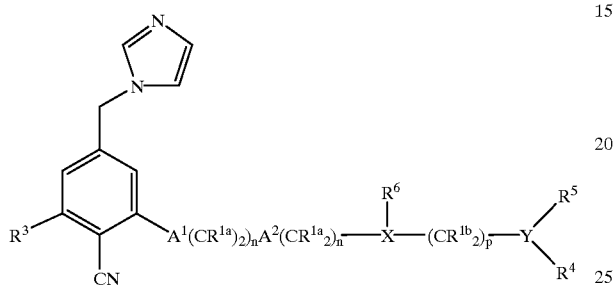

Ia wherein:
R$^{1a}$ is selected from: hydrogen or C$_1$–C$_6$ alkyl;
R$^{1b}$ is independently selected from:
 a) hydrogen,
 b) aryl, heterocycle, C$_3$–C$_{10}$ cycloalkyl, R$^8$O— or C$_2$–C$_6$ alkenyl,
 c) C$_1$–C$_6$ alkyl unsubstituted or substituted by aryl, heterocycle, cycloalkyl, alkenyl, or R$^8$O—;
R$^3$ and R$^4$ are independently selected from hydrogen, F, Cl, Br, N$_3$,
 CN, C$_1$–C$_6$ alkyl, substituted or unsubstituted aryl and substituted or unsubstituted heterocycle;
R$^5$ is selected from:
 a) hydrogen, and
 b) C$_1$–C$_6$ alkyl substituted with hydrogen or a group selected from unsubstituted or substituted aryl, unsubstituted or substituted heterocyclic, unsubstituted or substituted C$_3$–C$_{10}$ cycloalkyl, CF$_3$, NO$_2$, R$^8$O—, R$^9$S(O)$_q$—, R$^8$C(O)—, R$^8$OC(O)—, N$_3$, and CN; R$^6$ is independently selected from:
 a) hydrogen,
 b) C$_1$–C$_6$ alkyl, C$_1$–C$_6$ perfluoroalkyl, F, Cl, CN, NO$_2$, and
 c) C$_1$–C$_6$ alkyl substituted by C$_1$–C$_6$ perfluoroalkyl, R$^8$O—, R$^8$C(O)—, or R$^8$OC(O)—;
R$^8$ is independently selected from hydrogen, C$_1$–C$_6$ alkyl, benzyl and aryl;
R$^9$ is independently selected from C$_1$–C$_6$ alkyl, benzyl and aryl;
A$^1$ and A$^2$ are independently selected from: a bond, —HC=CH—, —C≡C—, O, S(O)$_q$, O(C=O), and (O=C)O;
X is selected from:
 a) aryl,
 b) heteroaryl,
 c) cycloalkyl,
 d) heterocycle, and
 e) a bond;
Y is selected from:
 a) aryl,
 b) substituted aryl,
 c) heterocycle, and
 d) substituted heterocycle;
n is 0, 1, 2, 3 or 4;
p is 0, 1, 2, 3 or 4; and
q is 0, 1, or 2;
provided that

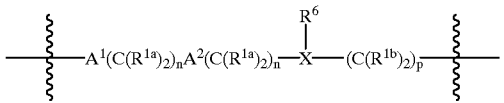

is not a bond;
or the pharmaceutically acceptable salts thereof.

A further embodiment of the compounds of the instant invention is illustrated by Formula Ib:

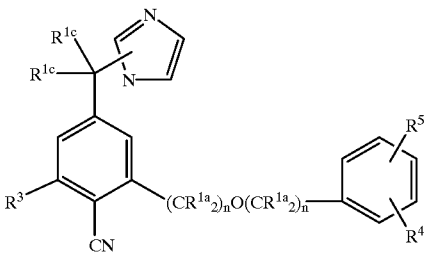

Ib wherein:
R$^{1a}$ is selected from:
 a) hydrogen,
 b) unsubstituted or substituted aryl; unsubstituted or substituted heterocycle; unsubstituted or substituted heteroaryl; C$_3$–C$_{10}$ cycloalkyl, C$_2$–C$_6$ alkenyl, C$_2$–C$_6$ alkynyl, R$^8$O—, R$^9$S(O)$_q$—, CN, NO$_2$, R$^8$C(O)—, R$^8$OC(O)—, or N$_3$;
 c) C$_1$–C$_6$ alkyl, unsubstituted or substituted by aryl, heterocyclic, C$_3$–C$_{10}$ cycloalkyl, C$_2$–C$_6$ alkenyl, C$_2$–C$_6$ alkynyl, R$^8$O—, R$^9$S(O)$_q$—, CN, R$^8$C(O)—, R$^8$OC(O)—, N$_3$, or —R$^8$C(O)O—;
R$^{1c}$ is independently selected from: H, unsubstituted or substituted C$_1$–C$_6$ alkyl, unsubstituted or substituted aryl, and unsubstituted or substituted heteroaryl;
R$^3$ is selected from hydrogen, F, Cl, Br, N$_3$, CN, C$_1$–C$_6$ alkyl, substituted or unsubstituted aryl and substituted or unsubstituted heterocycle;
R$^4$ and R$^5$ are independently selected from:
 a) H,
 b) halogen,
 c) aryl, unsubstituted or substituted,
 d) heteroaryl, unsubstituted or substituted, and
 e) C$_1$–C$_6$ alkyl;
R$^8$ is independently selected from hydrogen, C$_1$–C$_6$ alkyl, benzyl and aryl;
R$^9$ is independently selected from C$_1$–C$_6$ alkyl, benzyl and aryl;
n is independently selected from: 0, 1, 2, 3 or 4; and
q is 0, 1 or 2;
or the pharmaceutically acceptable salts thereof.

Specific examples of the compounds of the invention are:
 3-(biphenyl-4-ylmethoxy)-4-imidazol-1-ylmethyl-benzonitrile 3-(biphenyl-4-yl-2-ethoxy)-4-imidazol-1-ylmethylbenzonitrile
3-(biphenyl-3-ylmethoxy)-4-imidazol-1-ylmethyl-benzonitrile
2-(biphenyl-4-ylmethoxy)-4-imidazol-1-ylmethyl-benzonitrile
2-(biphenyl-4-yl-2-ethoxy)-4-imidazol-1-ylmethyl-benzonitrile
1-tert-butoxycarbonyl-4-(3-chlorophenyl)-2(S)-[2-(2-cyano-5-imidazol-1-ylmethyl-phenoxy)ethyl]piperazine
2-(3-chlorophenoxy)-4-imidazol-1-ylmethyl-benzonitrile
2-(4-chlorophenyl-2-ethoxy)-4-imidazol-1-ylmethyl-benzonitrile
2-(3-chlorophenyl-2-ethoxy)-4-imidazol-1-ylmethyl-benzonitrile
2-(2-chlorophenyl-2-ethoxy)-4-imidazol-1-ylmethyl-benzonitrile
2-(phenyl-2-ethoxy)-4-imidazol-1-ylmethyl-benzonitrile
2-(3-chlorobenzyloxy)-4-imidazol-1-ylmethyl-benzonitrile
2-(4-chlorobenzyloxy)-4-imidazol-1-ylmethyl-benzonitrile
2-(2,4-dichlorobenzyloxy)-4-imidazol-1-ylmethyl-benzonitrile
2-(benzyloxy)-4-imidazol-1-ylmethyl-benzonitrile
2-(biphenyl-2-ylmethoxy)-4-imidazol-1-ylmethyl-benzonitrile
2-(phenyl-4-butoxy)-4-imidazol-1-ylmethyl-benzonitrile
2-(phenyl-3-propoxy)-4-imidazol-1-ylmethyl-benzonitrile
2-(biphenyl-4-yl-2-ethoxy)-4-(1,2,4-triazol-1-yl)methyl-benzonitrile
2-(biphenyl-4-yl-2-ethoxy)-4-(2-methyl-imidazol-1-yl)methyl-benzonitrile
2-(biphenyl-4-yl-2-ethoxy)-4-benzimidazol-1-yl)methyl-benzonitrile
4-imidazol-1-ylmethyl-2-(naphthalen-2-yloxy)-benzonitrile
2-(3-cyanophenoxy)-4-imidazol-1-ylmethyl-benzonitrile
2-(3-bromophenoxy)-4-imidazol-1-ylmethyl-benzonitrile
2-(biphen-3-yloxy)-4-imidazol-1-ylmethyl-benzonitrile
2-(biphen-4-yloxy)-4-imidazol-1-ylmethyl-benzonitrile
2-(3-acetylphenoxy)-4-imidazol-1-ylmethyl-benzonitrile
2-(2-acetylphenoxy)-4-imidazol-1-ylmethyl-benzonitrile
2-(3-trifluoromethylphenoxy)-4-imidazol-1-ylmethyl-benzonitrile
2-(3-methylphenoxy)-4-imidazol-1-ylmethyl-benzonitrile
2-(2-methylphenoxy)-4-imidazol-1-ylmethyl-benzonitrile
2-(4-methylphenoxy)-4-imidazol-1-ylmethyl-benzonitrile
2-(3-methoxyphenoxy)-4-imidazol-1-ylmethyl-benzonitrile
2-(2-methoxyphenoxy)-4-imidazol-1-ylmethyl-benzonitrile
2-(4-methoxyphenoxy)-4-imidazol-1-ylmethyl-benzonitrile
2-(3,5-dimethylphenoxy)-4-imidazol-1-ylmethyl-benzonitrile
2-(3,4-dimethylphenoxy)-4-imidazol-1-ylmethyl-benzonitrile
2-(3,5-dimethoxyphenoxy)-4-imidazol-1-ylmethyl-benzonitrile
2-(1-naphthyloxy)-4-imidazol-1-ylmethyl-benzonitrile
2-(2,4-dichlorophenoxy)-4-imidazol-1-ylmethyl-benzonitrile
2-(3-fluorophenoxy)-4-imidazol-1-ylmethyl-benzonitrile
2-(3-t-butylphenoxy)-4-imidazol-1-ylmethyl-benzonitrile
2-[3-(N,N-diethylamino)phenoxy]-4-imidazol-1-ylmethyl-benzonitrile
2-(3-n-propylphenoxy)-4-imidazol-1-ylmethyl-benzonitrile
2-(2,3-dimethoxyphenoxy)-4-imidazol-1-ylmethyl-benzonitrile
2-(2,3-dimethylphenoxy)-4-imidazol-1-ylmethyl-benzonitrile
2-(3,4-dimethoxyphenoxy)-4-imidazol-1-ylmethyl-benzonitrile
2-(2,5-dimethoxyphenoxy)-4-imidazol-1-ylmethyl-benzonitrile
2-(3,4-dichlorophenoxy)-4-imidazol-1-ylmethyl-benzonitrile
2-(2,4-dimethylphenoxy)-4-imidazol-1-ylmethyl-benzonitrile
2-(4-chloro-2-methylphenoxy)-4-imidazol-1-ylmethyl-benzonitrile
2-(5-chloro-2-methylphenoxy)-4-imidazol-1-ylmethyl-benzonitrile
2-(2-chloro-4,5-dimethylphenoxy)-4-imidazol-1-ylmethyl-benzonitrile
2-(5-hydroxymethyl-2-methoxyphenoxy)-4-imidazol-1-ylmethyl-benzonitrile
4-imidazol-1-ylmethyl-2-(3-phenylamino-phenoxy)-benzonitrile
4-imidazol-1-ylmethyl-2-[3-(2-methylphenylamino)-phenoxy]-benzonitrile
4-imidazol-1-ylmethyl-2-(3-phenoxy-phenoxy)-benzonitrile
2-(2-benzoyl-phenoxy)-4-imidazol-1-ylmethyl-benzonitrile
1-(5-chloro-2-methoxy-phenyl)-3-[3-(2-cyano-5-imidazol-1-ylmethyl-phenoxy)-phenyl]-urea
1-(2,5-dimethoxy-phenyl)-3-[3-(2-cyano-5-imidazol-1-ylmethyl-phenoxy)-phenyl]-urea
2-(3-benzyloxy-phenoxy)-4-imidazol-1-ylmethyl-benzonitrile
2-(4-benzyloxy-phenoxy)-4-imidazol-1-ylmethyl-benzonitrile
2-(2-benzyl-phenoxy)-4-imidazol-1-ylmethyl-benzonitrile
2-(3-ethynyl-phenoxy)-4-imidazol-1-ylmethyl-benzonitrile
2-(4-acetyl-3-methyl-phenoxy)-4-imidazol-1-ylmethyl-benzonitrile
4-imidazol-1-ylmethyl-2-(1H-indazol-6-yloxy)-benzonitrile
4-imidazol-1-ylmethyl-2-(5,6,7,8-tetrahydro-naphthalen-1-yloxy)-benzonitrile
4-imidazol-1-ylmethyl-2-(8-oxo-5,6,7,8-tetrahydro-naphthalen-1-yloxy)-benzonitrile 4-imidazol-1-ylmethyl-2-(1H-indol-7-yloxy)-benzonitrile
4-imidazol-1-ylmethyl-2-(3-oxo-indan-4-yloxy)-benzonitrile
4-imidazol-1-ylmethyl-2-(1-indol-4-yloxy)-benzonitrile
2-[3-(2-hydroxy-ethoxy)-phenoxy]-4-imidazol-1-ylmethyl-benzonitrile
4-imidazol-1-ylmethyl-2-(4-imidazol-1-yl-phenoxy)-benzonitrile
4'-(2-cyano-5-imidazol-1-ylmethyl-phenoxy)-biphenyl-4-carbonitrile
N-[3-(2-cyano-5-imidazol-1-ylmethyl-phenoxy)-phenyl]-acetamide
4-imidazol-1-ylmethyl-2-(9-oxo-9H-fluoren-4-yloxy)-benzonitrile
3-(2-cyano-5-imidazol-1-ylmethyl-phenoxy)-Nphenyl-benzamide
3-(2-cyano-5-imidazol-1-ylmethyl-phenoxy)-N-ethyl-N-phenyl-benzamide
3-(2-cyano-5-imidazol-1-ylmethyl-phenoxy)-N-cyclopropylmethyl-N-phenyl-benzamide
2-(5-chloro-pyridin-3-yloxy)-4-imidazol-1-ylmethyl-benzonitrile
N-[3-(2-cyano-5-imidazol-1-ylmethyl-phenoxy)-phenyl]-benzenesulfonamide
4-imidazol-1-ylmethyl-2-(indan-5-yloxy)-benzonitrile
3-(9H-carbazol-2-yloxy)-4-imidazol-1-ylmethyl-benzonitrile
4-imidazol-1-ylmethyl-2-(5,6,7,8-tetrahydro-naphthalen-2-yloxy)-benzonitrile
4-imidazol-1-ylmethyl-2-(2-methoxy-4-propenyl-phenoxy)-benzonitrile
4-imidazol-1-ylmethyl-2-[4-(3-oxo-butyl)-phenoxy]-benzonitrile
2-(3-chlorophenoxy)-5-imidazol-1-ylmethyl-benzonitrile
2-(4-chlorophenoxy)-4-imidazol-1-ylmethyl-benzonitrile
2-(3,5-dichlorophenoxy)-4-imidazol-1-ylmethyl-benzonitrile
2-(pyridin-3-yloxy)-4-imidazol-1-ylmethyl-benzonitrile
2-(2-chlorophenoxy)-4-imidazol-1-ylmethyl-benzonitrile
2-(3-chlorophenoxy)-5-(4-phenyl-imidazol-1-ylmethyl)-benzonitrile
2-(biphen-2-yloxy)-4-imidazol-1-ylmethyl-benzonitrile
2-(phenoxy)-4-imidazol-1-ylmethyl-benzonitrile
2-(2-chloro-4-methoxyphenoxy)-4-imidazol-1-ylmethyl-benzonitrile
2-(2-chloro phenylsulfanyl)-4-imidazol-1-ylmethyl-benzonitrile
4-imidazol-1-ylmethyl-2-(naphthalen-2-ylsulfanyl)-benzonitrile
2-(2,4-dichlorophenylsulfanyl)-4-imidazol-1-ylmethyl-benzonitrile
2-(2,4-dichloro-benzenesulfinyl)-4-imidazol-1-ylmethyl-benzonitrile
2-(2,4-dichloro-benzenesulfonyl)-4-imidazol-1-ylmethyl-benzonitrile
2-(2-methyl-pyridin-3-yloxy)-4-imidazol-1-ylmethyl-benzonitrile
2-(2,4-dimethyl-pyridin-3-yloxy)-4-imidazol-1-ylmethyl-benzonitrile
2-(4-chloro-2-methoxyphenoxy)-4-imidazol-1-ylmethyl-benzonitrile
2-(2-chlorophenoxy)-4-(5-methyl-imidazol-1-ylmethyl)-benzonitrile
2-(2-chlorophenoxy)-4-(4-methyl-imidazol-1-ylmethyl)-benzonitrile
2-(3-chloro-5-trifluoromethyl-pyridin-2-yloxy)-4-imidazol-1-ylmethyl-benzonitrile
2-(2,4-dichlorophenoxy)-4-(2-methyl-imidazol-1-ylmethyl)-benzonitrile
N-[3-(2-cyano-5-imidazol-1-ylmethyl-phenoxy)-phenyl]-benzamide
2-[3-(2-cyano-5-imidazol-1-ylmethyl-phenoxy)-phenyl]-N-phenyl-acetamide
4-imidazol-1-ylmethyl-2-(quinolin-6-yloxy)-benzonitrile
4-imidazol-1-ylmethyl-2-(2-oxo-1,2-dihydro-quinolin-6-yloxy)-benzonitrile
N-[3-(2-cyano-5-imidazol-1-ylmethyl-phenoxy)-pheny]-2-phenyl-acetamide
5-(2-cyano-5-imidazol-1-ylmethyl-phenoxy)-N-cyclohexyl-nicotinamide
N-(3-chloro-phenyl)-5-(2-cyano-5-imidazol-1-ylmethyl-phenoxy)-nicotinamide
2-(2,3-dimethoxyphenoxy)-4-(2,4-dimethyl-imidazol-1-ylmethyl)-benzonitrile
4-(2-methyl-imidazol-1-ylmethyl)-2-(naphthalen-2-yloxy)-benzonitrile
4-(1-imidazol-1-yl-1-methyl-ethyl)-2-(naphthalen-2-yloxy)-benzonitrile
1-[4-iodo-3-(naphthalen-2-yloxy)-benzyl]-1H-imidazole
acetic acid 3-[3-(2-chloro-phenoxy)-4-cyano-benzyl]-3H-imidazol-4-ylmethyl ester
2-(2-chloro-phenoxy)-4-(5-hydroxymethyl-imidazol-1-ylmethyl)-benzonitrile
4-(5-aminomethyl-imidazol-1-ylmethyl)-2-(2-chloro-phenoxy)-benzonitrile
N-{3-[4-cyano-3-(2,3-dimethoxy-phenoxy)-benzyl]-3H-imidazol-4-ylmethyl}-2-cyclohexyl-acetamide
2-(3-chloro-phenoxy)-4-[(4-chloro-phenyl)-imidazol-1-yl-methyl]-benzonitrile
2-(3-chloro-phenoxy)-4-[1-(4-chloro-phenyl)-2-hydroxy-1-imidazol-1-yl-ethyl]-benzonitrile
2-(3-chloro-phenoxy)-4-[(4-chloro-phenyl)-hydroxy-(3H-imidazol-4-yl)-methyl]-benzonitrile
2-(2,4-dichloro-phenylsulfanyl)-4-[5-(2-morpholin-4-yl-ethyl)-imidazol-1-ylmethyl]-benzonitrile
2-(2,4-dichloro-phenoxy)-4-[5-(2-morpholin-4-yl-ethyl)-imidazol-1-ylmethyl]-benzonitrile
4-[hydroxy-(3-methyl-3H-imidazol-4-yl)-methyl]-2-(naphthalen-2yloxy)-benzonitrile
4-[amino-(3-methyl-3H-imidazol-4-yl)-methyl]-2-(naphthalen-2-yloxy)-benzonitrile
4-[1-hydroxy-1-(3-methyl-3H-imidazol-4-yl)-ethyl]-2-(naphthalen-2-yloxy)-benzonitrile
4-[1-amino-1-(3-methyl-3H-imidazol-4-yl)-ethyl]-2-(naphthalen-2-yloxy)-benzonitrile hydrochloride
3-{2-cyano-5-[1-amino-1-(3-methyl-3H-imidazol-4-yl)-ethyl]-pheynoxy}-N-ethyl-N-phenyl-benzamide
3-{2-cyano-5-[1-hydroxy-1-(3-methyl-3H-imidazol-4-yl)-ethyl]-phenoxy}-N-ethyl-N-phenyl-benzamide
4-[1-hydroxy-1-(3-methyl-3H-imidazol-4-yl)-ethyl]-2-(3-phenylamino-phenoxy)-benzonitrile
4-[1-hydroxy-1-(3-methyl-3H-imidazol-4-yl)-ethyl]-2-(3-phenoxy-phenoxy)-benzonitrile 2-(3-benzoyl-phenoxy)-4-[1-hydroxy-1-(3-methyl-3H-imidazol-4-yl)-ethyl]-benzonitrile
2-(3-tert-butyl-phenoxy)-4-[1-hydroxy-1-(3-methyl-3H-imidazol-4-yl)-ethyl]-benzonitrile
2-(3-diethylamino-phenoxy)-4-[1-hydroxy-1-(3-methyl-3H-imidazol-4-yl)-ethyl]-benzonitrile
2-(5-chloro-2-oxo-2H-[1,2']bipyridinyl-5'-ylmethoxy)-4-imidazol-1-ylmethyl-benzonitrile
4-Imidazol-1-ylmethyl-2-[2-(2-oxo-2H-pyridin-1-yl)-phenoxy]-benzonitrile
4-Imidazol-1-ylmethyl-2-[3-(2-oxo-2H-pyridin-1-yl)-phenoxy]-benzonitrile
4-Imidazol-1-ylmethyl-2-[4-(2-oxo-2H-pyridin-1-yl)-phenoxy]-benzonitrile or the pharmaceutically acceptable salts thereof.

The preferred compounds of the instant invention are:

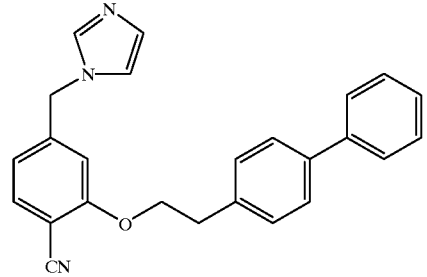

2-(Biphenyl-4-ylmethoxy)-4-imidazol-1-ylmethyl-benzonitrile

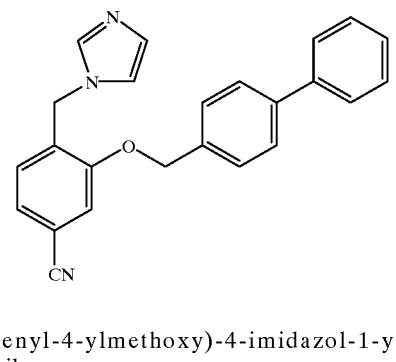

3-(Biphenyl-4-ylmethoxy)-4-imidazol-1-ylmethyl-benzonitrile

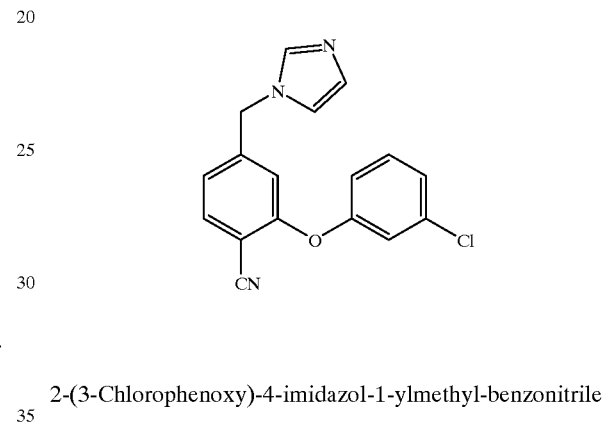

2-(3-Chlorophenoxy)-4-imidazol-1-ylmethyl-benzonitrile 3-(Biphenyl-3-ylmethoxy)-4-imidazol-1-ylmethyl-benzonitrile

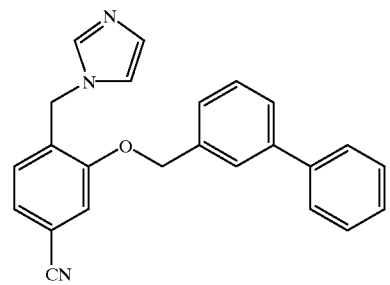

4-Imidazol-1-ylmethyl-2-(naphthalen-2-yloxy)-benzonitrile

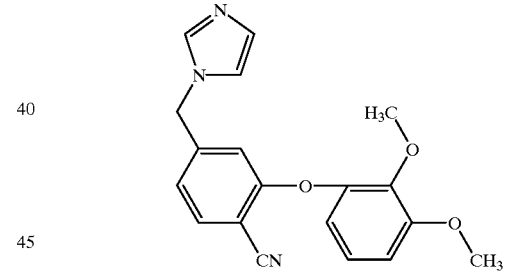

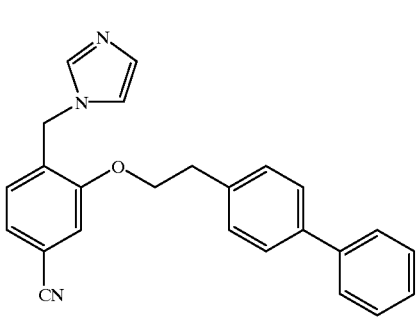

3-(Biphenyl-4-yl-2-ethoxy)-4-imidazol-1-ylmethylbenzonitrile.

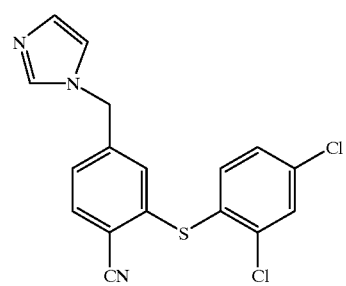

2-(2,4-Dichlorophenylsulfanyl)-4-imidazol-1-ylmethyl-benzonitrile

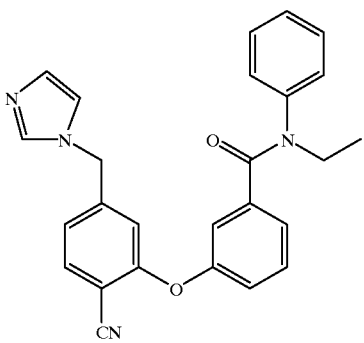

3-(2-Cyano-5-imidazol-1-ylmethyl-phenoxy)-N-ethyl-N-phenyl-benzamide

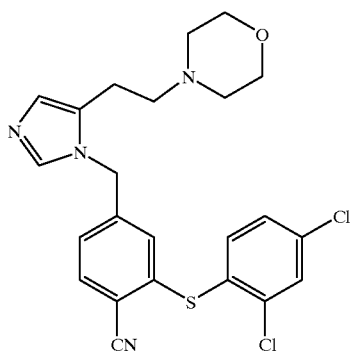

2-(2,4-dichloro-phenylsulfanyl)-4-[5-(2-morpholin-4-yl-ethyl)-imidazol-1-ylmethyl]-benzonitrile

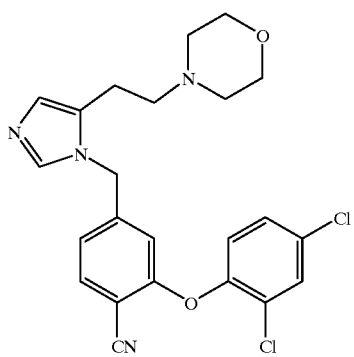

2-(2,4-dichloro-phenoxy)-4-[5-(2-morpholin-4-yl-ethyl)-imidazol-1-ylmethyl]-benzonitrile

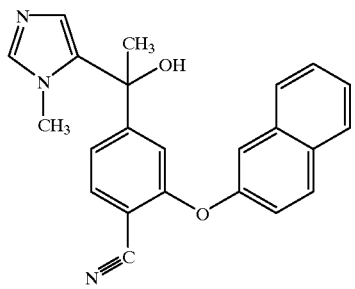

4-[1-hydroxy-1-(3-methyl-3H-imidazol-4-yl)-ethyl]-2-(naphthalen-2-yloxy)-benzonitrile

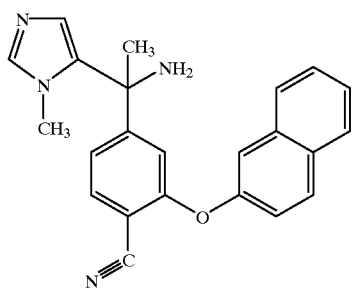

4-[1-amino-1-(3-methyl-3H-imidazol-4-yl)-ethyl]-2-(naphthalen-2-yloxy)-benzonitrile or a pharmaceutically acceptable salt thereof.

The compounds of the present invention may have asymmetric centers and occur as racemates, racemic mixtures, and as individual diastereomers, with all possible isomers, including optical isomers, being included in the present invention. When any variable, substituent or term (e.g. aryl, heterocycle, $R^{1a}$, $R^2$, n, p, etc.) occurs more than one time in a formula or generic structure, its definition at each occurrence is independent of the definition at every other occurrence. Also, combinations of substituents/or variables are permissible only if such combinations result in stable compounds.

As used herein, "alkyl" is intended to include both branched and straight-chain saturated aliphatic hydrocarbon groups having 1 to 6 carbon atoms, unless otherwise specified; "alkoxy" represents an alkyl group having 1 to 4 carbon atoms, unless otherwise indicated, attached through an oxygen bridge. "Halogen" or "halo" as used herein means fluoro, chloro, bromo and iodo.

As used herein, "aryl" is intended to mean any stable monocyclic, bicyclic or tricyclic carbon ring of up to 7 members in each ring, wherein at least one ring is aromatic. Examples of such aryl elements include phenyl, naphthyl, tetrahydronaphthyl, indanyl, indanonyl, biphenyl, tetralinyl, tetralonyl, fluorenonyl, phenanthryl, anthryl or acenaphthyl.

As used herein, "aralkyl" is intended to mean an aryl moiety, as defined above, attached through a $C_1$–$C_6$ alkyl linker, where alkyl is defined above. Examples of aralkyls inlcude, but are not limited to, benzyl, naphthylmethyl and phenylpropyl.

As used herein, "heteroaralkyl" is intended to mean a heteroaryl moiety, as defined below, attached through a $C_1$–$C_6$ alkyl linker, where alkyl is defined above. Examples of heteroaralkyls include, but are not limited to, 2-pyridylmethyl, 2-imidazolylethyl, 2-quinolinylmethyl, 2-imidazolylmethyl and the like.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, benzopyrazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperdinyl, 2-oxopyrrolidinyl, 2-oxopyridyl, 2-oxoquinolinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolidinyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein, the terms "substituted $C_1$–$C_6$ alkyl" and "substituted $C_1$–$C_6$ alkoxy" are intended to include the branch or straight-chain alkyl group of the specified number of carbon atoms, wherein the carbon atoms may be substituted with F, Cl, Br, $CF_3$, $N_3$, $NO_2$, $NH_2$, oxo, —OH, —O($C_1$–$C_6$ alkyl), S(O)0-2, ($C_1$–$C_6$ alkyl)S(O)$_{0-2}$—, ($C_1$–$C_6$ alkyl)S(O)$_{0-2}$($C_1$–$C_6$ alkyl)—, $C_3$–$C_{10}$ cycloalkyl, $C_2$–$C_6$ alkenyl, $C_2$–$C_6$ alkynyl, —C(O)NH, ($C_1$–$C_6$ alkyl) C(O)NH—, $H_2$N—C(NH)—, ($C_1$–$C_6$ alkyl)C(O)—, —O($C_1$–$C_6$ alkyl)$CF_3$, ($C_1$–$C_6$ alkyl)OC(O)—, ($C_1$–$C_6$ alkyl)O($C_1$–$C_6$ alkyl)—, ($C_1$–$C_6$ alkyl)C(O)$_2$($C_1$–$C_6$ alkyl)—, ($C_1$–$C_6$ alkyl)OC(O)NH—, aryl, benzyl, heterocycle, aralkyl, heteroaralkyl, halo-aryl, halo-benzyl, halo-heterocycle, cyano-aryl, cyano-benzyl and cyano-heterocycle.

As used herein, the terms "substituted aryl", "substituted heteroaryl", "substituted aralkyl" and "substituted heteroaralkyl" are intended to include the cyclic group containing from 1 to 3 substitutents in addition to the point of attachment to the rest of the compound. Such substitutents are preferably selected from the group which includes but is not limited to F, Cl, Br, $CF_3$, $NH_2$, N($C_1$–$C_6$ alkyl)$_2$, $NO_2$, CN, $N_3$, $C_1$–$C_{20}$ alkyl, $C_1$–$C_6$ alkoxy, —OH, —O($C_1$–$C_6$ alkyl), S(O)$_{0-2}$, ($C_1$–$C_6$ alkyl)S(O)$_{0-2}$—, ($C_1$–$C_6$ alkyl)S(O)$_{0-2}$($C_1$–$C_6$ alkyl)—, ($C_1$–$C_6$ alkyl)C(O)NH—, $H_2$N—C(NH)—, ($C_1$–$C_6$ alkyl)C(O)—, ($C_1$–$C_6$ alkyl)OC(O)—, ($C_1$–$C_6$ alkyl)O($C_1$–$C_6$ alkyl)—, ($C_1$–$C_6$ alkyl)C(O)$_2$($C_1$–$C_6$ alkyl)—, ($C_1$–$C_6$ alkyl)OC(O)NH—, aryl, aralkyl, heteroaryl, heteroaralkyl, halo-aryl, halo-aralkyl, halo-heterocycle, halo-heteroaralkyl, cyano-aryl, cyano-aralkyl, cyano-heterocycle and cyano-heteroaralkyl.

Examples of "spiro $C_1$–$C_6$ cycloalkyl" include:

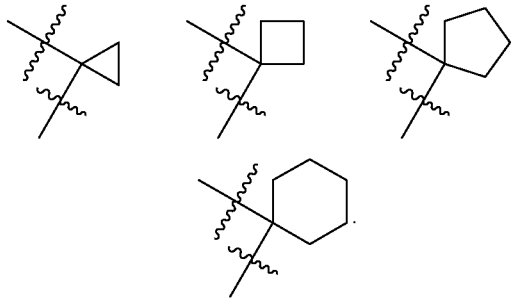

Lines drawn into the ring systems from substituents (such as from $R^2$, $R^3$, $R^4$ etc.) indicate that the indicated bond may be attached to any of the substitutable ring carbon atoms or heteroatom.

Preferably, $R^{1a}$ and $R^{1b}$ are independently selected from: hydrogen, unsubstituted or substituted aryl or unsubstituted or substituted $C_1$–$C_6$ alkyl.

Preferably, $R^{1c}$ is selected from hydrogen, unsubstituted or substituted aryl, unsubstituted or substituted heterocycle, —$OR^8$, —N($R^8$)$_2$ and unsubstituted or substituted $C_1$–$C_6$ alkyl.

Preferably, $R^2$ is H, CN or halo. Most preferably, $R^2$ is CN.

Preferably, $R^3$ is selected from hydrogen, halo, CN, $NO_2$, and unsubstituted or substituted $C_1$–$C_6$ alkyl.

Preferably, $R^4$ and $R^5$ are independently selected from hydrogen, halo, unsubstituted or substituted $C_1$–$C_6$ alkyl, unsubstituted or substituted aryl, unsubstituted or substituted heterocycle, $N_3$, —C(O)$R^8$, —O($C_1$–$C_6$ alkyl)$OR^8$, and —($C_1$–$C_6$ alkyl)$OR^8$.

Preferably, $R^6$ is selected from: hydrogen, F, Cl, Br, CN, $NO_2$, $R^8$OC(O)—, $N_3$, and $C_1$–$C_6$ alkyl.

Preferably, $R^{13}$ is selected from hydrogen, unsubstituted or substituted $C_1$–$C_6$ alkyl, unsubstituted or substituted aryl, —($C_1$–$C_6$ alkyl)$OR^8$, —($C_1$–$C_6$ alkyl)OC(O)($C_1$–$C_6$ alkyl), —($C_1$–$C_6$ alkyl)N($R^8$)$_2$, and —($C_1$–$C_6$ alkyl)NHC(O) ($C_1$–$C_6$ alkyl)$R^8$. More preferably, $R^{13}$ is substituted $C_1$–$C_6$ alkyl, unsubstituted or substituted aryl, —($C_1$–$C_6$ alkyl) $OR^8$, —($C_1$–$C_6$ alkyl)OC(O)($C_1$–$C_6$ alkyl), —($C_1$–$C_6$ alkyl) N($R^8$)$_2$, and —($C_1$–$C_6$ alkyl)NHC(O)($C_1$–$C_6$ alkyl)$R^8$.

Preferably, $A^1$ and $A^2$ are independently selected from: a bond, O and S(O)$_q$. More preferably, $A^1$ is a bond and $A^2$ is selected from O and S(O)$_q$.

Preferably, $A^3$ is selected from a bond, O, —$NR^8$, C(O), —S(O)$_q$, —C(O)N($R^8$), —N($R^8$)C(O), —S(O)$_q$NH, —NHS (O)$_q$, or —NHC(O)NH.

Preferably $A^4$ is selected from a bond, $C=CH_2$, or spiro $C_3-C_6$ cycloalkyl. Most preferably, $A^4$ is a bond.

Preferably, W is a heterocycle, selected from pyrrolidinyl, imidazolyl, imidazolinyl, pyridinyl, thiazolyl, pyridonyl, 2-oxopiperidinyl, oxazolyl, indolyl, quinolinyl, isoquinolinyl, triazolyl and thienyl. Most preferably, W is imidazolyl or pyridyl.

Preferably, X is selected from a bond, aryl and heterocycle.

Preferably, Y is selected from an unsubstituted or substituted aryl or an unsubstituted or substituted heterocycle. More preferably, Y is selected from phenyl, furyl, thienyl and pyridyl. Most preferably, Y is phenyl.

Preferably, m, n, p, q, r, s and t are independently 0, 1, or 2.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{1a}$, $R^{1b}$, $R^{13}$, n, p, etc.), at a particular location in a molecule, be independent of its definitions elsewhere in that molecule. Thus, $-C(R^{1a})_2$ represents $-CH_2$, $-CHCH_3$, $-CHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

These reactions may be employed in a linear sequence to provide the compounds of the invention or they may be used to synthesize fragments which are subsequently joined by the alkylation reactions described in the Schemes.

Synopsis of Schemes

Schemes 1 to 9 describe the synthesis of compounds of formulae A and I. The starting materials can be obtained from commercial sources or they can be obtained using standard transformations (e.g. esterification of the hydroxy acid) from commercially available materials.

In Scheme 1, amino-hydroxybenzoates of type II can be converted to the corresponding iodide III by treatment with acidic aqueous $NaNO_2$ followed by the addition of KI. The phenol may then be alkylated by treatment with a base such as NaH or $Cs_2CO_3$ in an organic solvent (for example DMF) followed by the addition of an electrophile to yield IV. Reduction of the ester of IV using, for example, $LiBH_4$ in THF then yields the alcohol V which can in turn be treated with $Zn(CN)_2$ in DMF and a palladium catalyst to give VI. The alcohol of VI can be converted into a leaving group of VII in a number of ways. One such procedure involves reaction of the alcohol with a sulfonyl chloride in the presence of an organic base (e.g. triethylamine) in an organic solvent such as dichloromethane. A second method requires the reaction of the alcohol with $CBr_4$ and a phosphine such as triphenyl phosphine in an organic solvent such as dichloromethane. A third method involves reaction of the alcohol with N-bromosuccinimide and dimethyl sulfide in dichloromethane. The reaction of VII with imidazole in a polar solvent such as DMF then affords compounds of formula IA. In addition, VII upon reaction with 4-iodo-1-tritylimidazole in THF with 1,2-dibromoethane, Zn and $NiCl_2(PPh_3)_2$ and subsequent methanolysis may yield compounds of formula IB.

Scheme 2 shows an alternative route for the conversion of III into VI employing chemical transformations described above.

In Scheme 3, the phenol X can be converted to the corresponding triflate XI using trifluoromethane sulfonic anhydride in an organic solvent such as dichloromethane with an organic base such as triethylamine. The triflate may then be converted to the nitrile XII, the ester reduced to XIII and the alcohol transformed to a leaving group as shown in XIV using previously described reactions. Treatment of XIV as above would then produce compounds of formula IC or ID.

An alternative route for the synthesis of compounds of formula IA and IB is given in Scheme 4. Methylhydroxybenzoic acids of structure XV may be bis alkylated by treatment with a base such as NaH or $Cs_2CO_3$ in an organic solvent (for example DMF) followed by the addition of an electrophile to yield XVI saponification using aqueous hydroxide then affords the acid XVII. Acid XVII is then converted to the primary amide XIX via the acid chloride XVIII (prepared with thionyl chloride in a solvent such as toluene then a reaction with ammonia in, for example, chloroform). Treatment of XIX with thionyl chloride in DMF results in the nitrile XX which can be brominated at the benzylic position using, for example, N-bromosuccinimide and benzoyl peroxide in carbon tetrachloride. Transformations, as before, then yield IA or IB.

An alternative route for the synthesis of compounds of formula IA and IB is shown in Scheme 5 which incorporates the reaction steps described above but alters the order of these transformations to give XXIV which is converted to IA by treatment with a halide or mesylate.

Two routes to compounds containing a diaryl ether linkage as illustrated in XXVII are described in Scheme 6. The bromo fluoride XXV is transformed to the fluoro nitrile with zinc cyanide, then converted to ID in a series of transformations described in previous schemes.

Scheme 7 illustrates yet another route for the synthesis of compounds of formula IA.

Schemes 8 and 9 describe routes for the preparation of compounds XXXIX and XXXX which contain a heteroatom at the benzylic position between W and the phenyl ring of IA.

SCHEME 1
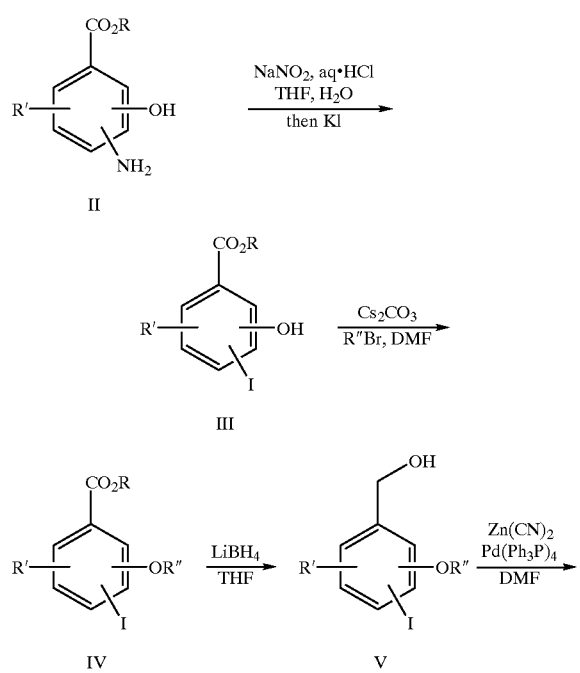
SCHEME 2
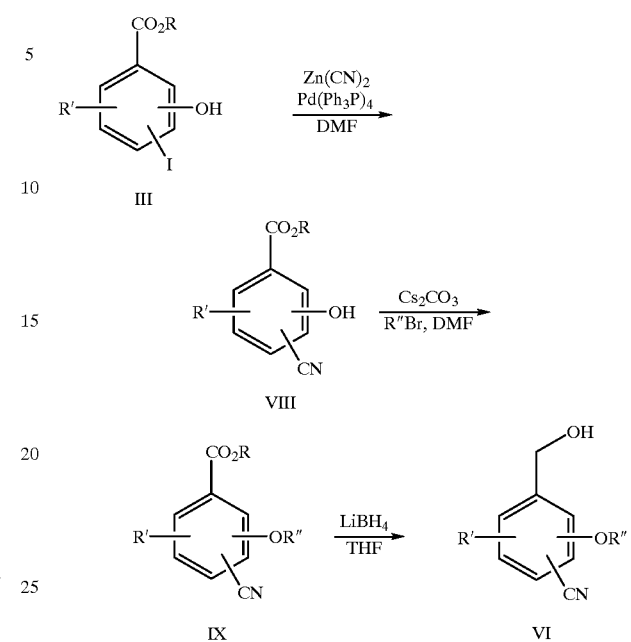
SCHEME 3
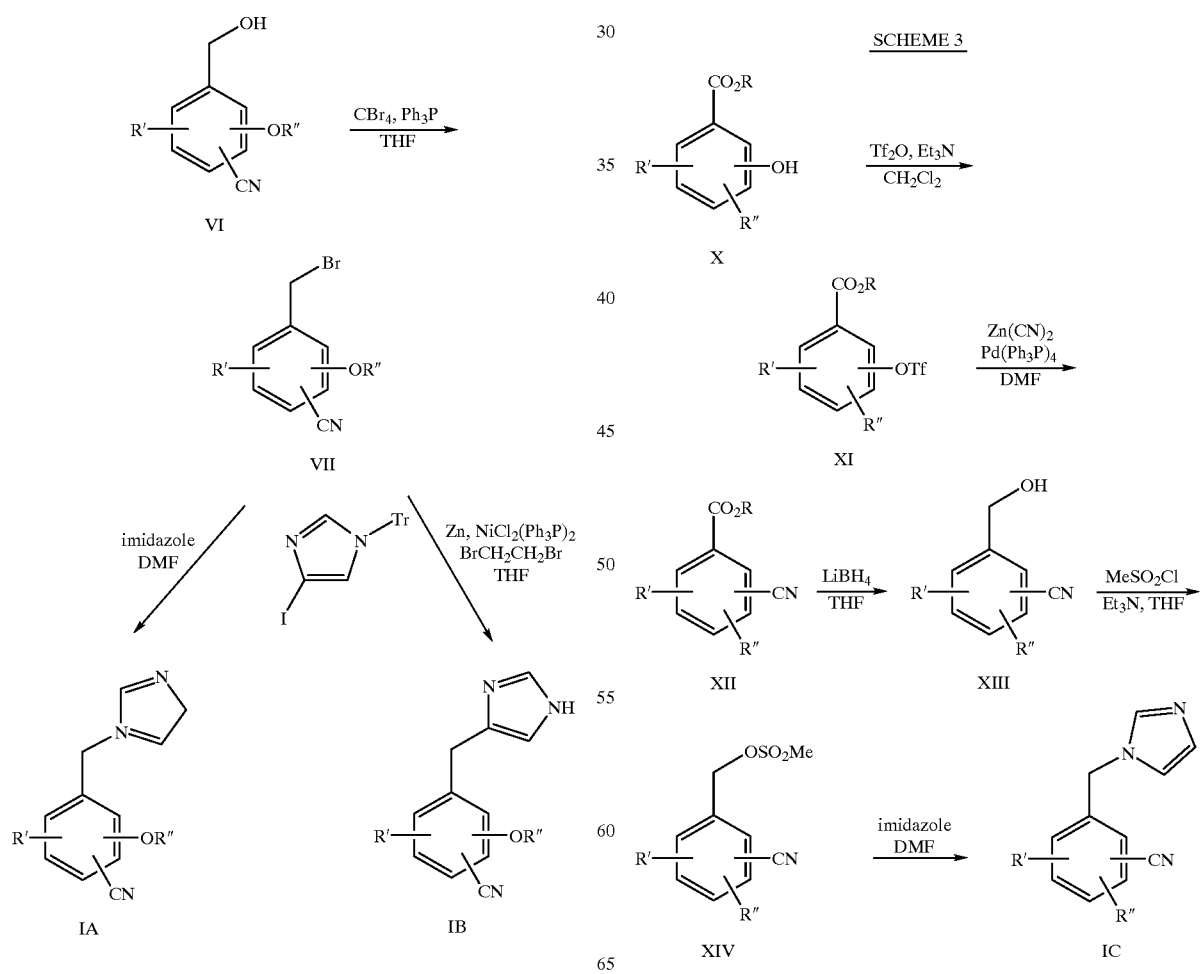

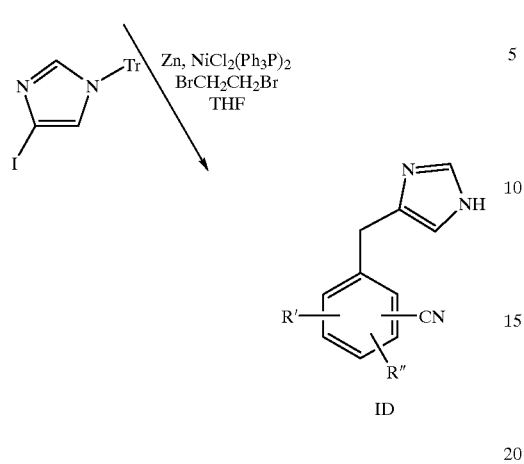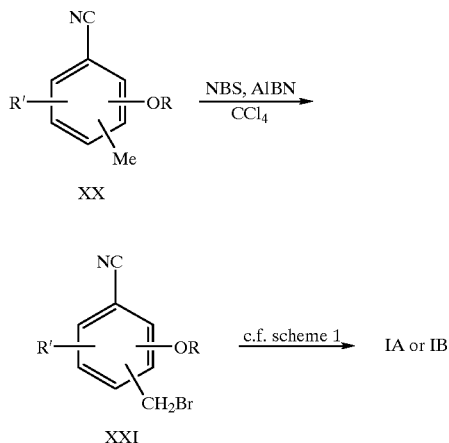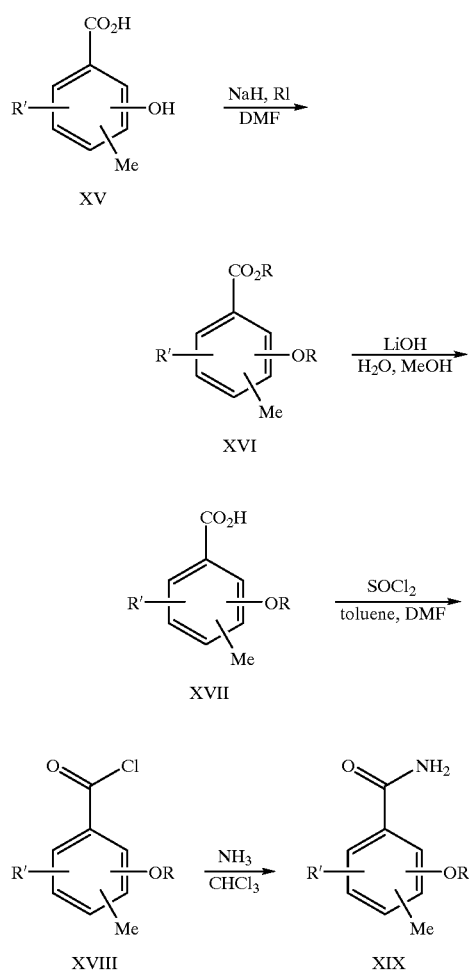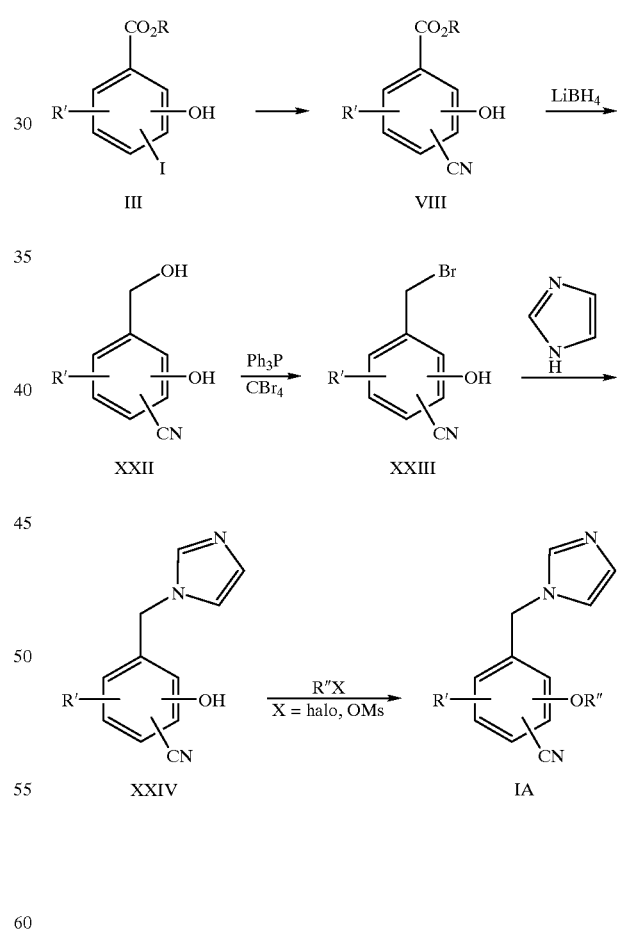

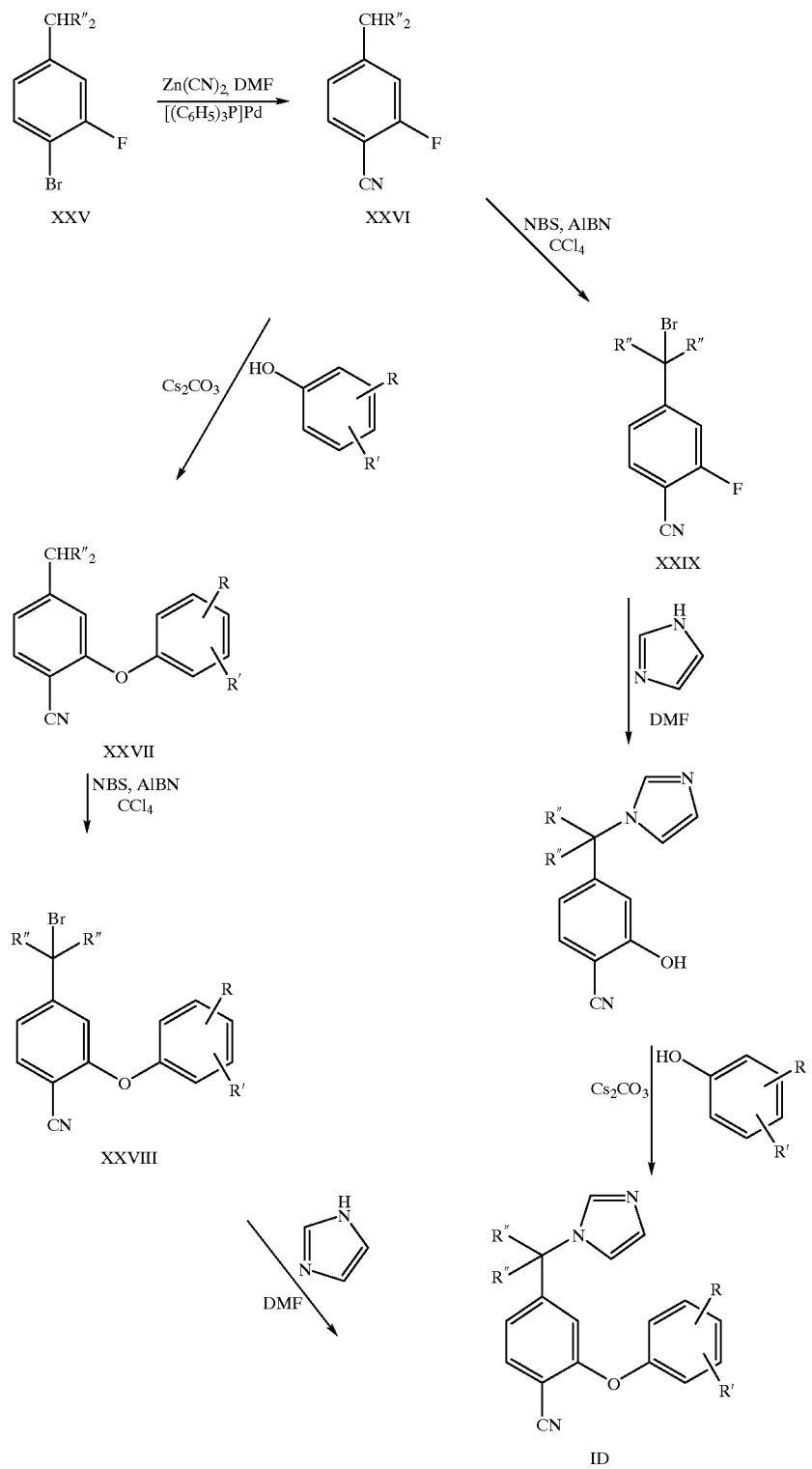

SCHEME 7
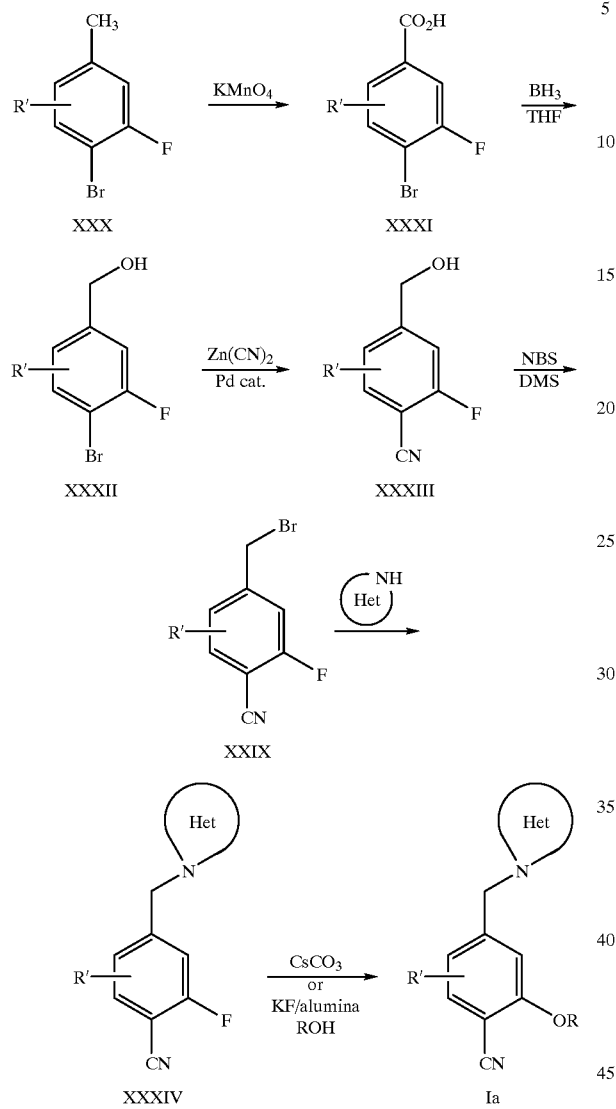
SCHEME 8
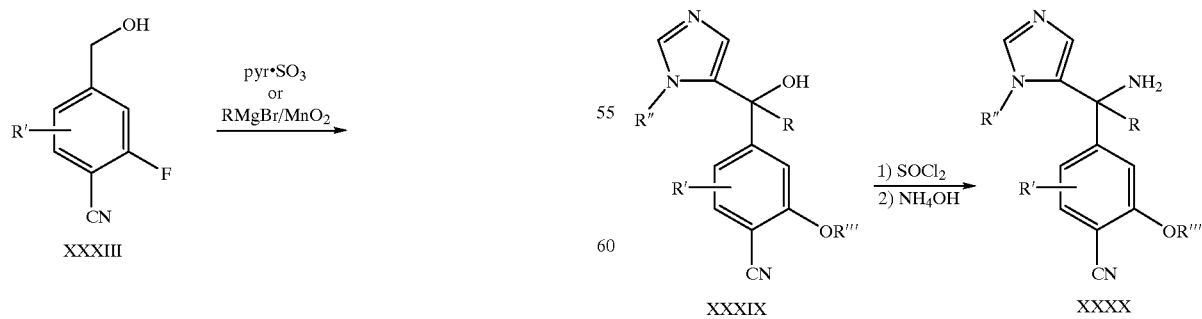
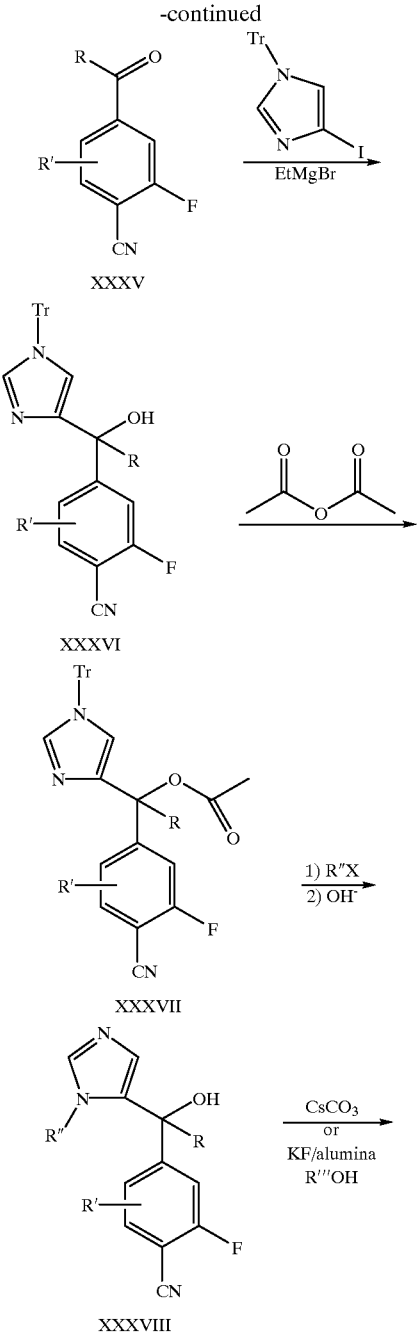

SCHEME 9

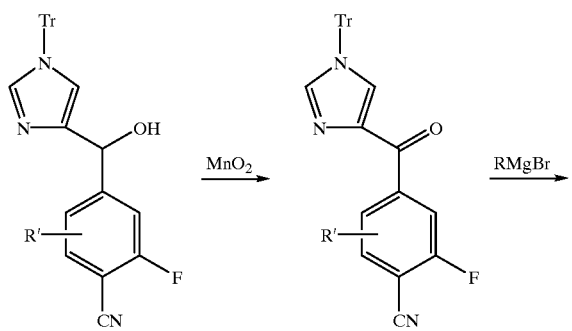

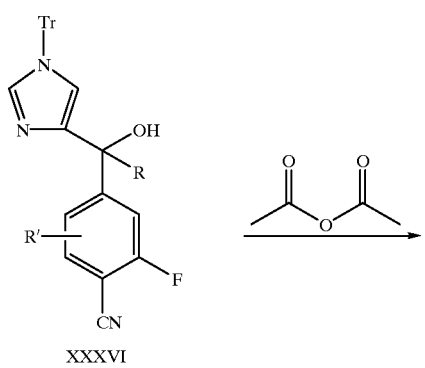

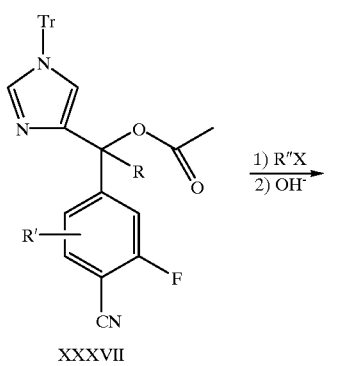

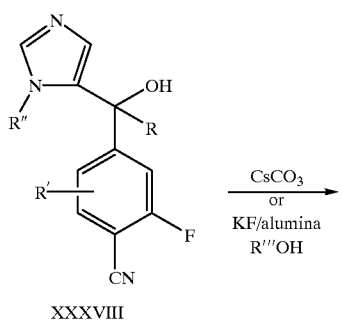

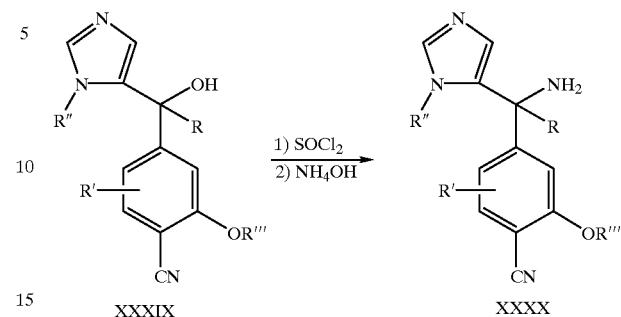

In the above Schemes, it is understood that

R independently represents $R^{1c}$ or its protected precursors thereof;

R' independently represents $R^3$ or its protected precursors thereof;

R" independently represents $R^{13}$ or its protected precursors thereof;

R'" independently represents the following moiety:

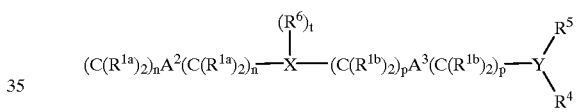

In a preferred embodiment of the instant invention the compounds of this instant invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 29, is at least 100 times greater than the in vitro activity of the same compound against geranylgeranyl-protein transferase-type I in the assay described in Example 30. Preferably, a selective compound exhibits at least 1000 times greater activity against one of the enzymatic activities when comparing geranylgeranyl-protein transferase-type I inhibition and farnesyl-protein transferase inhibition.

In another preferred embodiment of the instant invention the compounds of this instant invention are dual inhibitors of farnesyl-protein transferase and geranylgeranyl-protein transferase type I. Such a dual inhibitor will exhibit certain characteristics when assessed in in vitro assays, which are dependent on the type of assay employed.

In a SEAP assay, such as described in Example 33, it is preferred that the dual inhibitor compound has an in vitro inhibitory activity ($IC_{50}$) that is less than about 12 μM against K4B-Ras dependent activation of MAP kinases in cells. More preferably, the dual inhibitor compound has an in vitro inhibitory activity ($IC_{50}$) against K4B-Ras dependent activation of MAP kinases in cells which is more than about 5 times lower than the inhibitory activity ($IC_{50}$)

against Myr-Ras dependent activation of MAP kinases in cells. Also more preferably, in a SEAP assay, the dual inhibitor compound has an inhibitory activity ($IC_{50}$) that is less than about 10 nM against H-Ras dependent activation of MAP kinases in cells.

In a GGTase plus anion assay, such as described in Example 30, it is preferred that the dual inhibitor compound has an in vitro inhibitory activity ($IC_{50}$) that is less than about 5 μM against transfer of a geranylgeranyl residue to a protein or peptide substrate comprising a $CAAX^G$ motif by geranylgeranyl-protein transferase type I in the presence of a modulating anion. More preferably, the dual inhibitor compound has an in vitro inhibitory activity ($IC_{50}$) that is less than about 1 μM against transfer of a geranylgeranyl residue to a protein or peptide substrate comprising a $CAAX^G$ motif by geranylgeranyl-protein transferase type I in the presence of a modulating anion. Preferably, the dual inhibitor compound has an in vitro inhibitory activity ($IC_{50}$) in the in vitro assay as described in Example 29 that is less than about 1 μM against transfer of a farnesyl residue to a protein or peptide substrate, comprising a $CAAX^F$ motif, by farnesyl-protein transferase. More preferably, the dual inhibitor compound has an in vitro inhibitory activity ($IC_{50}$) that is less than about 100 nM against transfer of a farnesyl residue to a protein or peptide substrate, comprising a $CAAX^F$ motif, by farnesyl-protein transferase. Also preferably, the dual inhibitor compound has an in vitro inhibitory activity ($IC_{50}$) in the in vitro assay as described in Example 32, that is less than about 100 nM against the anchorage independent growth of H-ras-transformed mammalian fibroblasts.

The protein or peptide substrate utilized in the instant assay may incorporate any CAAX motif that is geranylgeranylated by GGTase-I. The term "$CAAX^G$" will refer to such motifs that may be geranylgeranylated by GGTase-I. It is understood that some of the "$CAAX^G$" containing protein or peptide substrates may also be farnesylated by farnesyl-protein transferase. In particular such "$CAAX^G$" motifs include (the corresponding human protein is in parentheses): CVIM (K4B-Ras) (SEQ.ID.NO.: 1), CVLL (mutated H-Ras) (SEQ.ID.NO.: 2), CVVM (N-Ras) (SEQ.ID.NO.: 3), CIIM (K4A-Ras) (SEQ.ID.NO.: 4), CLLL (Rap-IA) (SEQ.ID.NO.: 5), CQLL (Rap-IB) (SEQ.ID.NO.: 6), CSIM (SEQ.ID.NO.: 7), CAIM (SEQ.ID.NO.: 8), CKVL (SEQ.ID.NO.: 9), and CLIM (PFX) (SEQ.ID.NO.: 10). Preferably, the CAAX motif is CVIM.

As used herein, the term "$CAAX^F$" is used to designate a protein or peptide substrate that incorporates four amino acid C-terminus motif that is farnesylated by farnesyl-protein transferase. It is understood that certain of the "$CAAX^F$" containing protein or peptide substrates may also be geranylgeranylated by GGTase-I. In particular such "$CAAX^F$" motifs include (the corresponding human protein is in parentheses): CVLS (H-ras) (SEQ.ID.NO.: 11), CVIM (K4B-Ras) and CVVM (N-Ras).

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, src, abl, lck, fyn) or by other mechanisms.

The compounds of the instant invention inhibit a prenyl-protein transferase and, in particular, the farnesylation of the oncogene protein Ras. The instant compounds may also inhibit tumor angiogenesis, thereby affecting the growth of tumors (J. Rak et al. *Cancer Research*, 55: 4575–4580 (1995)). Such anti-angiogenesis properties of the instant compounds may also be useful in the treatment of certain forms of vision deficit related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

The instant compounds may also be useful as inhibitors of proliferation of vascular smooth muscle cells and therefore useful in the prevention and therapy of arteriosclerosis and diabetic vascular pathologies.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and sus- pending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The injectable suspensions or solutions may be introduced into a patient's blood-stream by local bolus injection. Alternatively, it may be advantageous to administer the suspensions or solution in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

Compounds of Formula A may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention may also be co-administered with other well known therapeutic agents that are selected for their particular usefulness against the condition that is being treated. For example, the compounds of the instant invention may also be co-administered with other well known cancer therapeutic agents that are selected for their particular usefulness against the condition that is being treated. Included in such combinations of therapeutic agents are combinations of the instant prenyl-protein transferase inhibitors and an antineoplastic agent. It is also understood that such a combination of antineoplastic agent and inhibitor of a prenyl-protein transferase may be used in conjunction with other methods of treating cancer and/or tumors, including radiation therapy and surgery.

Examples of an antineoplastic agent include, in general, microtubule-stabilizing agents (such as paclitaxel (also known as Taxol®), docetaxel (also known as Taxotere®), epothilone A, epothilone B, desoxyepothilone A, desoxyepothilone B or their derivatives); microtubule-disruptor agents; alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

The preferred class of antineoplastic agents is the taxanes and the preferred antineoplastic agent is paclitaxel.

Radiation therapy, including x-rays or gamma rays which are delivered from either an externally applied beam or by implantation of tiny radioactive sources, may also be used in combination with the instant inhibitor of a prenyl-protein transferase alone to treat cancer.

Additionally, compounds of the instant invention may also be useful as radiation sensitizers, as described in WO 97/38697, published on Oct. 23, 1997, and herein incorporated by reference.

The instant compounds may also be useful in combination with other inhibitors of parts of the signaling pathway that links cell surface growth factor receptors to nuclear signals initiating cellular proliferation. Thus, the instant compounds may be utilized in combination with farnesyl pyrophosphate competitive inhibitors of the activity of farnesyl-protein transferase or in combination with a compound which has Raf antagonist activity. The instant compounds may also be co-administered with compounds that are selective inhibitors of geranylgeranyl protein transferase. In particular, if the compound of the instant invention is a selective inhibitor of farnesyl-protein transferase, co-administered with a compound(s) that is a selective inhibitor of geranylgeranyl protein transferase may provide the therapeutic effect of administration of a dual inhibitor as described hereinabove, and thus offer certain advantages over administration of only the compound of the instant invention.

In particular, the compounds disclosed in the following patents and publications may be useful as farnesyl pyrophosphate-competitive inhibitor component of the instant composition: U.S. Ser. Nos. 08/254,228 and 08/435,047. Those patents and publications are incorporated herein by reference.

In practicing methods of this invention, which comprise administering, simultaneously or sequentially or in any order, two or more of a protein substrate-competitive inhibitor and a farnesyl pyrophosphate-competitive inhibitor, such administration can be orally or parenterally, including intravenous, intramuscular, intraperitoneal, subcutaneous, rectal and topical routes of administration. It is preferred that such administration be orally. It is more preferred that such administration be orally and simultaneously. When the protein substrate-competitive inhibitor and farnesyl pyrophosphate-competitive inhibitor are administered sequentially, the administration of each can be by the same method or by different methods.

The instant compounds may also be useful in combination with an integrin antagonist for the treatment of cancer, as described in U.S. Ser. No. 09/055,487, filed Apr. 6, 1998, which is incorporated herein by reference.

As used herein the term an integrin antagonist refers to compounds which selectively antagonize, inhibit or counteract binding of a physiological ligand to an integrin(s) that is involved in the regulation of angiogenisis, or in the growth and invasiveness of tumor cells. In particular, the term refers to compounds which selectively antagonize, inhibit or counteract binding of a physiological ligand to the αvβ3 integrin, which selectively antagonize, inhibit or counteract binding of a physiological ligand to the αvβ5 integrin, which antagonize, inhibit or counteract binding of a physiological ligand to both the αvβ3 integrin and the αvβ5 integrin, or which antagonize, inhibit or counteract the activity of the particular integrin(s) expressed on capillary endothelial cells. The term also refers to antagonists of the α1β1, α2β1, α5β1, α6β1 and α6β4 integrins. The term also refers to antagonists of any combination of αvβ3 integrin, αvβ5 integrin, α1β1, α2β1, α5β1, α6β1 and α6β4 integrins. The instant compounds may also be useful with other agents that inhibit angiogenisis and thereby inhibit the growth and invasiveness of tumor cells, including, but not limited to angiostatin and endostatin.

Similarly, the instant compounds may be useful in combination with agents that are effective in the treatment and prevention of NF-1, restenosis, polycystic kidney disease, infections of hepatitis delta and related viruses and fungal infections.

If formulated as a fixed dose, such combination products employ the combinations of this invention within the dosage range described below and the other pharmaceutically active agent(s) within its approved dosage range. Combinations of the instant invention may alternatively be used sequentially with known pharmaceutically acceptable agent(s) when a multiple combination formulation is inappropriate.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well-known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The present invention also encompasses a phanaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

Preparation of 3-(Biphenyl-4-ylmethoxy)-4-imidazol-1-ylmethyl-benzonitrile

Step A: Preparation of Phenyl 2-hydroxy-4-iodobenzoate

A solution of $NaNO_2$ (1.33 g, 19.3 mmol) in 10 mL water was added to a solution of phenyl-4-amino-2-hydroxybenzoate (4.02 g, 17.6 mmol) in 3N HCl (35 mL) and THF (10 mL) at 0° C. The resulting yellow solution was stirred for 30 minutes then KI (8.74 g, 52.7 mmol) in water (13 mL) was added. After 10 minutes, the dark brown/red slurry was poured into EtOAc, washed twice with water then with aqueous sodium bisulfite and brine. The dried ($MgSO_4$) solution was filtered and concentrated to give a dark oil. Column chromatography (silica gel; hexane:EtOAc 15:1) gave the title compound as a white solid which contained approximately 15% of an unidentified impurity. This material was used as such in the next step.

Step B: Preparation of Phenyl 4-iodo-2-(Biphenyl-4-ylmethoxy)benzoate

To a solution of a phenol, as described in Step A, in 10 mL of dimethyl formamide (DMF) was added 4-phenylbenzyliodide (292 mg, 0.99 mmol) and $Cs_2CO_3$ (442 mg, 1.35 mmol) and the suspension was stirred for 16 hr. After this time, the reaction mixture was diluted with EtOAc, extracted with water (3×), washed with brine, dried ($MgSO_4$) and concentrated in vacuo. The residue was purified by flash chromatography ($SiO_2$; hexane:EtOAc 20:1) to provide an oil which crystallized from ether:hexane 1:10 to give the title compound as a white solid.

$^1$H NMR ($CDCl_3$) d 5.23 (2H, s), 7.17 (2H, m), 7.25 (1H, m), 7.3–7.6 (13H, m), 7.75 (1H, d).

Step C: Preparation of 4-Iodo-2-(biphenyl-4-ylmethoxy) benzylalcohol

To a solution of an ester, as described in Step B, in 5 mL of THF was added lithium borohydride (28 mg, 1.27 mmol) and heated at reflux for 30 minutes. After this time, the reaction mixture was poured into EtOAc and extracted with 1N HCl, then water, and then brine. The organic layer was separated, dried ($MgSO_4$) and evaporated in vacuo to afford the title compound as a white solid:

$^1$H NMR($CDCl_3$) d 2.17 (1H, t), 4.70 (2H, d), 5.12 (2H, s), 7.07 (1H, d), 7.3–7.7 (11H, m).

Step D: Preparation of 4-Cyano-2-(biphenyl-4-ylmethoxy) benzylalcohol

A solution of an iodide, as described in Step C, and $Zn(CN)_2$ (49 mg, 0.42 mmol) in DMF (5 mL) was degassed with argon for 15 minutes. $Pd(Ph_3P)_4$ (35 mg, 0.03 mmol) was added and the mixture heated to 80° C. for 16 hr. The mixture was poured into water and extracted with EtOAc (2×). The organic layers were washed with 1N HCl, water and then brine. They were then dried ($MgSO_4$) and the solvent removed. Chromatography of the residue (silica gel;

hexane:EtOAc 2:1) afforded the title compound as a white solid. $^1$H NMR(CDCl$_3$) d 2.18 (1H, t), 4.81 (2H, d), 5.17 (2H, s), 7.19 (1H, d), 7.3–7.65 (11H, m).

Step E: Preparation of Methanesulfonic Acid 2-(Biphenyl-4-ylmethoxy)-4-cyanobenzyl Ester A solution of an alcohol, as described in Step D, in dichloromethane (4 mL) at room temperature, was treated sequentially with Et$_3$N (81 μL, 0.59 mmol) and methanesulfonyl chloride (32 μL, 0.41 mmol). After 1 hr, a further Et$_3$N (81 μL, 0.59 mmol) and methanesulfonyl chloride (32 μL, 0.41 mmol) was added and stirred for another hour. The solution was poured into water, extracted with EtOAc, washed with brine, dried (MgSO$_4$) and evaporated to give a solid. Column chromatography (silica gel; hexane:EtOAc 2:1) gave the title compound as a solid. Rf (silica): 0.37 (hexane:EtOAc 2:1).

$^1$H NMR(CDCl$_3$) d 2.95 (3H, s), 5.18 (2H, s), 5.35 (2H, s), 7.2–7.7 (12H, m).

Step F: Preparation of 3-(Biphenyl-4-ylmethoxy)-4-imidazol-1-ylmethyl-benzonitrile A solution of a mesylate, as described in Step E and imidazole (45 mg, 0.66 mmol) in DMF (1.5 mL) was stirred at room temperature for 16 hr. The mixture was poured into a saturate NaHCO$_3$ solution, extracted with EtOAc, washed with water and then brine, dried (MgSO$_4$) and evaporated to give a solid. Column chromatography (silica gel; 2% MeOH in CHCl$_3$) gave an oil which crystallized from ether to afford the title compound. $^1$H NMR(CDCl$_3$) d 5.16 (2H, s), 5.20 (2H, s), 6.89 (1H, t), 7.00 (1H, d), 7.09 (1H, s), 7.24 (2H, m), 7.35–7.5 (5H, m), 7.53 (1H, s), 7.6–7.68 (4H, m). Analysis calculated for C$_{24}$H$_{19}$N$_3$O: C, 78.88; H, 5.24; N, 11.50; Found: C, 78.67; H, 5.54; N, 11.31.

Example 2

Preparation of 3-(Biphenyl-4-yl-2-ethoxy)-4-imidazol-1-ylmethylbenzonitrile Hydrochloride Step A: Preparation of Phenyl 4-Cyano-2-hydroxybenzoate A solution of phenyl 2-hydroxy-4-iodobenzoate, as described in Example 1, Step A, (2.38 g, 7.0 mmol) and Zn(CN)$_2$ (575 mg, 4.9 mmol) in DMF was degassed with argon for 25 minutes. Pd(Ph$_3$P)$_4$ (404 mg, 0.35 mmol) was added and the mixture heated to 80° C. for 16 hr. The mixture was poured into 1N HCl and extracted with EtOAc (2×), washed with water then brine, dried (MgSO$_4$) and the solvent removed. Chromatography of the residue (silica gel; hexane:EtOAc 9:1) afforded the title compound as a white solid.

$^1$H NMR(CDCl$_3$) d 7.18–7.28 (3H, m), 7.35 (2H, m), 7.48 (2H, m), 8.19 (1H, d), 10.67 (1H, s).

Step B: Preparation of Phenyl 4-Cyano-2-(biphenyl-4-yl-2-ethoxy)benzoate

To a solution of a phenol, as described in Step A, in 5 mL of dimethyl formamide (DMF) was added biphenyl-4-ylethyl iodide (170 mg, 0.55 mmol) and Cs$_2$CO$_3$ (246 mg, 0.75 mmol). The suspension was stirred for 16 hr. After this time, the reaction mixture was diluted with EtOAc, extracted with water (3×), washed with brine, dried (MgSO$_4$) and concentrated in vacuo. The residue was purified by flash chromatography (SiO$_2$; hexane:EtOAc 9:1 then 4:1) to provide the title compound.

Rf (silica): 0.22 (hexane:EtOAc 9:1).

Step C: Preparation of 4-Cyano-2-(biphenyl-4-yl-2-ethoxy)benzyl Alcohol

To a solution of an ester, as described in Step B, in 3 mL of THF was added lithium borohydride (9.6 mg, 0.44 mmol) and heated at reflux for 1 hr. After this time, the reaction mixture was poured into EtOAc and extracted with 1N HCl, then water, then brine. The organic layer was separated, dried (MgSO$_4$) and evaporated in vacuo to afford the title compound as an oil. The residue was purified by flash chromatography (SiO$_2$; hexane:EtOAc 2:1) to provide the title compound.

$^1$H NMR(CDCl$_3$) d 2.16 (1H, t), 3.17 (2H, t), 4.25 (2H, t), 4.65 (1H, d), 7.06 (1H, d), 7.24 (1H, dd), 7.3–7.45 (6H, m), 7.55–7.6 (4H, m).

Step D: Preparation of 3-(Biphenyl-4-yl-2-ethoxy)-4-bromomethyl-benzonitrile

A mixture of an alcohol, as described in Step C, carbon tetrabromide (68 mg, 0.205 mmol) and PPh$_3$ (54 mg, 0.205 mmol) in THF (2 mL) was stirred for 16 hr. More carbon tetrabromide (68 mg, 0.205 mmol) and PPh$_3$ (54 mg, 0.205 mmol) were added and stirring continued for 24 hr. The solution was diluted with ether, filtered and the solvent concentrated. Chromatography of the residue (silica gel; hexane:EtOAc 9:1) afforded the title compound. Rf (silica): 0.78 (hexane:EtOAc 2:1).

Step E: Preparation of 3-(Biphenyl-4-yl-2-ethoxy)-4-imidazol-1-ylmethyl-benzonitrile Hydrochloride A solution of a bromide, as described in Step D, and imidazole (26 mg, 0.38 mmol) in DMF (2 mL) was stirred at room temperature for 16 hr. The mixture was poured into saturate NaHCO$_3$ solution, extracted with EtOAc, washed with water then brine, dried (MgSO$_4$) and evaporated to give a solid. Column chromatography (silica gel; hexane:EtOAc 1:1 then 2% MeOH in CHCl$_3$) gave an oil which was treated with 0.5 mL 1N HCl in ether to afford (after removal of the ether) the title compound as a solid.

$^1$H NMR(CD$_3$OD) d 3.18 (2H, t), 4.44 (2H, t), 5.38 (2H, s), 7.2–7.5 (10 H, m), 7.5–7.7 (4H, m), 8.62 (1H, s).

Example 3

Preparation of 3-(Biphenyl-3-ylmethoxy)-4-imidazol-1-ylmethyl-benzonitrile Hydrochloride Following the procedure described in Example 2, Steps A to F, but using biphenyl-3-ylmethyl bromide, as described in Step B, as starting material, the title compound was obtained as a solid.

$^1$H NMR(CD$_3$OD) d 5.27 (2H, s), 5.52 (2H, s), 7.3–7.7 (14H, m), 8.85 (1H, s).

Example 4

Preparation of 2-(Biphenyl-4-ylmethoxy)-4-imidazol-1-ylmethyl-benzonitrile

Step A: Preparation of Methyl 4-Amino-3-hydroxybenzoate

HCl (g) was bubbled through a solution of 4-amino-3-hydroxybenzoic acid (7 g, 54.8 mmol) in MeOH (450 mL) until saturated then the mixture was heated at 70° C. for 16 hr. The mixture was concentrated in vacuo, the residue taken up in EtOAc, washed with saturated NaHCO$_3$ then brine and dried (MgSO$_4$). Removal of the solvent yielded the title compound as a brown solid.

1H NMR(CD$_3$OD) d 3.80 (3H, s), 6.66 (1H, d), 7.32 (1H, dd), 7.37 (1H, dd).

Step B: Preparation of Methyl 3-Hydroxy-4-iodobenzoate

A solution of NaNO$_2$ (15.89 g, 0.092 mol) in water (30 mL) was added to a solution of methyl 4-amino-3-hydroxybenzoate (14.00 g, 0.084 mol) in 3N HCl (120 mL) and THF (20 mL) at 0° C. The resulting dark red solution was stirred for 30 minutes then KI (41.68 g, 2.51 mol) in water (30 mL) was added. After 10 minutes, the dark brown/red slurry was poured into EtOAc, washed twice with water then with aqueous sodium bisulfite and brine. The dried (MgSO$_4$) solution was filtered and concentrated to give a dark oil. Column chromatography (silica gel; hexane:EtOAc 15:1) gave the title compound.
Step C: Preparation of Methyl 4-Cyano-3-hydroxybenzoate A solution of methyl 3-hydroxy-4-iodobenzoate (2.38 g, 7.0 mmol) (as described in Step B) and Zn(CN)$_2$ (0.575 g, 4.9 mmol) in DMF was degassed with argon for 25 minutes. Pd(Ph$_3$P)$_4$ (0.404 g, 0.35 mmol) was added and the mixture heated to 80° C. for 16 hr. The mixture was poured into 1N HCl and extracted with EtOAc (2×), washed with water then brine, dried (MgSO$_4$) and the solvent removed. Chromatography of the residue (silica gel; hexane:EtOAc 9:1) afforded the title compound as a white solid.

$^1$H NMR(CDCl$_3$) d 3.95 (3H, s), 6.54 (1H, br s), 7.60 (1H, d), 7.65 (1H, d), 7.570 (1H, s).

Step D: Preparation of 2-Hydroxy-4-hydroxymethylbenzonitrile

Methyl 4-cyano-3-hydroxybenzoate (as described in Example 4, Step C) (0.50 g, 2.82 mmol) was dissolved in dry THF (30 mL), treated with LiBH$_4$ (2.0M solution in THF) (5.64 mL, 11.28 mmol) and heated at reflux overnight. The reaction mixture was concentrated, then partitioned between EtOAc (50 mL) and 1N HCl (50 mL), the aqueous layer extracted with additional EtOAc (2×50 mL), the organic layers combined, washed with brine, and dried (MgSO$_4$). Filtration and concentration to dryness gave the title compound.

$^1$H NMR (CD$_3$OD) δ 7.45 (1H, d, J=8 Hz), 6.98 (1H, d, J=1 Hz), 6.89 (1H, dd, J=1, 8, Hz), 4.58 (2H, s).

Step E: Preparation of 4-Bromomethyl-2-hydroxy-benzonitrile

2-Hydroxy-4-hydroxymethylbenzonitrile (0.20 g, 1.34 mmol) was dissolved in DMF (5 mL)—CH$_2$Cl$_2$(5 mL) and treated with triphenylphosphine (0.53 g, 2.01 mmol) and carbon tetrabromide (0.67 g, 2.01 mmol) at ambient temperature with stirring. After 2 h the reaction mixture was partitioned between EtOAc (100 mL)—H$_2$O (100 mL), the organic layer separated, dried (MgSO$_4$), and filtered to give the title compound after silica gel chromatography (15% EtOAc/hexane to 25% EtOAc/hexane).

$^1$H NMR (CD$_3$OD) δ 7.45 (1H, d, J=8 Hz), 6.94 (1H, s), 6.90 (1H, d, J=8, Hz), 4.40 (2H, s).

Step F: Preparation of 2-Hydroxy-4-imidazol-1-ylmethyl-benzonitrile

4-Bromomethyl-2-hydroxy-benzonitrile (0.22 g, 1.05 mmol) and imidazole (0.36 g, 5.23 mmol) were dissolved in DMF (10 mL) with stirring at ambient temperature. After stirring for 18 h the reaction mixture was concentrated in vacuo and purified by silica gel chromatography eluting with 2% CH$_3$OH/CH$_2$Cl$_2$ to 5% CH$_3$OH/CH$_2$Cl$_2$ to give the title compound.

$^1$H NMR (DMSO) δ 11.11 (1H, s), 7.74 (1H, s), 7.58 (1H, d, J=8 Hz), 7.17 (1H, s), 6.95 (1H, s), 6.74 (1H, d, J=8, Hz), 6.69 (1H, s), 5.23 (2H, s).

Step G: Preparation of 2-(Biphenyl-4-ylmethoxy)-4-imidazol-1-ylmethyl-benzonitrile Following the procedure described in Example 2, Step E but using 2-hydroxy-4-imidazol-1-ylmethyl-benzonitrile (as described in Step F) and biphenyl-4-ylmethyl iodide as starting materials, the title compound was obtained as a solid.

$^1$H NMR(CD$_3$OD) d 4.89 (2H, s), 5.28 (2H, s), 6.91 (1H, d), 7.06 (3H, m), 7.3–7.55 (5H, m), 7.6–7.66 (5H, m), 7.77 (1H, s). Analysis calculated for C$_{24}$H$_{19}$N$_3$O: C, 78.88; H, 5.24; N, 11.50; Found: C, 78.59; H, 5.31; N, 11.10.

Example 5

Preparation of 2-(Biphenyl-4-yl-2-ethoxy)-4-imidazol-1-ylmethyl-benzonitrile Hydrochloride Following the procedure described in Example 4, Step A to D but using biphenyl-4-ylethyl iodide as the starting material in Step B, and treatment of the final product with 1N HCl in ether, the title compound was obtained as a solid.

$^1$H NMR(CD$_3$OD) d 3.13 (2H, t), 4.28 (2H, t), 4.90 (2H, s), 6.83 (1H, dd), 6.95 (1H, s), 7.00 (1H, t), 7.11 (1H, t), 7.30 (1H, m), 7.35–7.45 (4H, m), 7.5–7.6 (5H, m), 7.76 (1H, s).

Example 6

Preparation of 1-tert-butoxycarbonyl-4-(3-chlorophenyl)-2(S)-[2-(2-cyano-5-imidazol-1-ylmethyl-phenoxy)ethyl]piperazine Step A: Preparation of L-N-tert-butoxycarbonyl Homoserine Lactone To a solution of L-homoserine lactone hydrochloride (10 g, 72.7 mmol) and (Boc)$_2$O (19.0 g, 87.2 mmol) in dichloromethane (200 mL) at 0° C. was added Et$_3$N (12.2 mL, 87.2 mmol) dropwise. The solution was warmed to room temperature and stirred for 16 hr. The mixture was poured into 10% citric acid solution, extracted with EtOAc, washed with saturated NaHCO$_3$ solution, then brine, dried (MgSO$_4$) and evaporated in vacuo. Column chromatography (silica gel; hexane:EtOAc 1:1 then pure EtOAc) afforded the title compound as a white solid. Rf (silica): 0.58 (hexane:EtOAc 1:1).

Step B: Preparation of L-N-tert-butoxycarbonyl Homoserine Lactol

To a solution of a lactone, as described in Step A, in THF (355 mL) at −78° C. was added DIBAL-H (1.0M in THF; 146 mL, 146 mmol) dropwise. The solution was stirred at −78° C. for 1 hr then EtOAc and sodium potassium tartrate solution were added and the resulting mixture stirred vigorously for 30 minutes. After extracting with EtOAc (4×) the combined organic layers were washed with brine and dried over MgSO$_4$. Removal of the solvent yielded an oil which solidified on standing. Column chromatography (silica gel; hexane:EtOAc 2:1 then 1:1) afforded the title compound as a white solid.

Step C: Preparation of 3(S)-(N'-tert-butoxycarbonylamino)-4-(N 3-chlorophenylamino)-butanol To a solution of a lactol, as described in Step B, and 3-chloroaniline (6.25 mL, 59.1 mmol) in dichloroethane (200 mL) at room temperature was added acetic acid (3.07 mL, 53.7 mmol) followed by Na(OAc)$_3$BH (17.1 g, 80.5 mmol) and the mixture stirred for 2 hr. Saturated NaHCO$_3$ solution was added and the mixture extracted with dichloromethane (3×), washed with brine, dried (MgSO$_4$) and concentrated in vacuo. Column chromatography (silica gel; hexane:EtOAc 2:1 then 1:1 then pure EtOAc) afforded the title compound as a white solid.

$^1$H NMR(CDCl$_3$) d 1.45 (9H, s), 1.5 (1H, m), 1.90 (1H, m), 2.96 (1H, br s), 3.11 (1H, m), 3.24 (1H, m), 3.73 (2H, m), 4.05 (2H, m), 4.75 (1H, d), 6.48 (1H, dd), 6.58 (1H, t), 6.67 (1H, dd), 7.07 (1H, t).

Step D: Preparation of 3(S)-(N'-tert-butoxycarbonylamino)-4-(N-3-chlorophenyl-N-chloroacetyl)amino-butanol To a solution of an amine, as described in Step C, in EtOAc (120 mL) and saturated NaHCO$_3$ (120 mL) at 0° C. was added chloroacetyl chloride (3.08 mL, 38.8 mL) dropwise. After 2 hr, the mixture was extracted with EtOAc (3×), washed with brine, dried (MgSO$_4$) and concentrated in vacuo to give the title product as a clear oil which was used as such.

Step E: Preparation of 1-tert-butoxycarbonyl-4-(3-chlorophenyl)-2(S)-(2-hydroxyethyl)-5-oxo-piperazine To a solution of a chloroacetamide, as described in Step D, in DMF (100 mL) at 0° C. was added Cs$_2$CO$_3$ (27.75 g, 85.2 mmol) and the reaction was stirred for 6 hr. The solution was poured into EtOAc and saturated NH$_4$Cl. Extracted with EtOAc (3×), washed with brine, dried and evaporated to give a yellow oil. Column chromatography (silica gel; hexane:EtOAc 2:1 then 1:1 then pure EtOAc) afforded the title compound as a clear oil.

Step F: Preparation of 1-tert-butoxycarbonyl-4-(3-chlorophenyl)-2(S)-[2-(2-cyano-5-methoxycarbonylphenoxy)ethyl]-5-oxo-piperazine To a solution of 250 mg of methyl 4-cyano-3-hydroxybenzoate (1.42 mmol), as described in Example 4, Step C, and PPh$_3$ (465 mg, 1.77 mmol) in THF (10 mL) was added dropwise a solution of the alcohol from Step E above (503 mg, 1.42 mmol) and DEAD (0.28 mL, 1.77 mmol) in THF (5 mL). After stirring for 16 hr, the solution was concentrated in vacuo and the residue taken up in EtOAc. This was then washed with 10% citric acid solution, saturated NaHCO$_3$ solution, brine and dried over MgSO$_4$. Filtration and removal of the solvent afforded an oil. Column chromatography (silica gel; hexane:EtOAc 4:1) afforded the title compound as a clear oil.

Step G: Preparation of 1-tert-butoxycarbonyl-4-(3-chlorophenyl)-2(S)-[2-(2-cyano-5-hydroxymethylphenoxy)ethyl]piperazine Following the procedure described in Example 1, Step C but using an ester, as described in Step F above, as the starting material, the title compound was obtained.

FAB mass spectrum m/z=472.21 (M+H requires 471.19)

Step H: Preparation of 1-tert-butoxycarbonyl-4-(3-chloro-phenyl)-2(S)-[2-(2-cyano-5-imidazol-1-ylmethyl-phenoxy)-ethyl]-5-oxo-piperazine Following the procedure described in Example 2, Steps D and E but using an alcohol, as described in Step G above, as the starting material, the title compound was obtained as a white solid.

FAB mass spectrum m/z=522.19 (M+H requires 522.22). Analysis calculated for C$_{28}$H$_{32}$N$_5$O$_3$Cl.0.15CH$_2$Cl$_2$: C, 63.22; H, 6.09; N, 13.10; Found: C, 63.17; H, 5.88; N, 12.93.

Example 7

Preparation of 2-(3-Chlorophenoxy)-4-imidazol-1-ylmethyl-benzonitrile Hydrochloride Step A: Preparation of 2-(3-chlorophenoxy)-4-methyl-benzonitrile To a solution of 2-fluoro-4-methylbenzonitrile (356mg, 3.96 mmol) and 3-chlorophenol (439 μL, 4.16 mmol) in 10 mL of DMSO was added Cs$_2$CO$_3$ (2.58 g, 7.92 mmol). The solution was heated at 80° C. for 4 h. The solution was diluted with EtOAc and was washed with Sat. NaHCO$_3$ solution, water, and brine. The organics were dried (MgSO$_4$), filtered, and concentrated in vacuo to give the title compound without further purification.

Step B: Preparation of 2-(3-Chlorophenoxy)-4-bromo-ylmethyl-benzonitrile

To a solution of 2-(3-chlorophenoxy)-4-methyl-benzonitrile (640 mg, 2.63 mmol), as described in Step A, NBS (470 mg, 2.63 mmol), and AIBN (13 mg, 0.07 mmol) in 24 mL of CCl$_4$ was refluxed under Ar for 4 h. The solution was filtered through a celite pad and the filtrate was concentrated in vacuo. The residue was purified by silica gel chromatography (0–6% EtOAc/hexane) to give the title compound.

Step C: Preparation of 2-(3-Chlorophenoxy)-4-imidazol-1-ylmethyl-benzonitrile Hydrochloride To a solution of 2-(3-chlorophenoxy)-4-bromo-ylmethyl-benzonitrile (111 mg, 0.34 mmol), as described in Step B, in 10 mL of DMF was added imidazole (117 mg, 1.72 mmol). The reaction was stirred for 18 h at ambient temperature.

The solvent was removed in vacuo, diluted with EtOAc and was washed with saturated NaHCO$_3$ solution, water, and brine. The organics were dried (MgSO4), filtered, and concentrated in vacuo. The residue was purified by silica gel chromatography (1% MeOH/CH$_2$Cl$_2$) and treated with 1N HCl in ether to give the title compound as a HCl salt.

$^1$HNMR (CDCl$_3$, 400 MHz) d 9.04(1H, s), 7.84(1H, d, J=8 Hz), 7.61(2H, d, J=11 Hz), 7.43(1H, t, J=8 Hz), 7.27(2H, t, J=7 Hz), 7.16 (1H, s), 7.05–7.07(2H, m), 5.50(2H, s). FAB MS 310 (M+1) Anal. calculated for C$_{17}$H$_{12}$N$_3$O$_1$Cl$_1$.1.0 HCl 0.85 H$_2$O C, 56.47; H, 4.10; N, 11.62; Found C, 56.85; H, 4.08; N, 11.23.

Example 8

Preparation of 2-(4-Chlorophenyl-2-ethoxy)-4-imidazol-1-ylmethyl-benzonitrile Hydrochloride Step A: Preparation of 2-Hydroxy-4-hydroxymethylbenzonitrile Methyl 4-cyano-3-hydroxybenzoate, as described in Example 4, Step C, (0.50 g, 2.82 mmol) was dissolved in dry THF (30 mL), treated with LiBH$_4$ (2.0M solution in THF) (5.64 mL, 11.28 mmol) and heated at reflux overnight. The reaction mixture was concentrated, then partitioned between EtOAc (50 mL) and 1N HCl (50 mL). Next, the aqueous layer was extracted with additional EtOAc (2×50 mL), the organic layers were combined, washed with brine, and dried (MgSO$_4$). The title compounds was obtained by filtering and concentrating to dryness.

$^1$H NMR (CD$_3$OD) d 7.45 (1H, d, J=8 Hz), 6.98 (1H, d, J=1 Hz), 6.89 (1H, dd, J=1, 8, Hz), 4.58 (2H, s).

Step B: Preparation of 4-Bromomethyl-2-hydroxy-benzonitrile 2-hydroxy-4-hydroxymethylbenzonitrile (0.20 g, 1.34 mmol) was dissolved in DMF (5 mL) and CH$_2$Cl$_2$(5 mL) and then treated with triphenylphosphine (0.53 g, 2.01 mmol) and carbon tetrabromide (0.67 g, 2.01 mmol) at ambient temperature with stirring. After 2 h, the reaction mixture was partitioned between EtOAc (100 mL) and H$_2$O (100 mL), the organic layer were separated, dried (MgSO$_4$), and filtered to give the title compound after silica gel chromatography (15% EtOAc/hexane to 25% EtOAc/hexane).

$^1$H NMR (CD$_3$OD) d 7.45 (1H, d, J=8 Hz), 6.94 (1H, s), 6.90 (1H, d, J=8, Hz), 4.40 (2H, s).

Step C: Preparation of 2-Hydroxy-4-imidazol-1-ylmethyl-benzonitrile 4-bromomethyl-2-hydroxy-benzonitrile (0.22 g, 1.05 mmol) and imidazole (0.36 g, 5.23 mmol) were dissolved in DMF (10 mL) with stirring at ambient temperature. After stirring for 18 h, the reaction mixture was concentrated in vacuo and purified by silica gel chromatography eluting with 2% CH$_3$OH/CH$_2$Cl$_2$ to 5% CH$_3$OH/CH$_2$Cl$_2$ to give the title compound.

$^1$H NMR (DMSO) d 11.11 (1H, s), 7.74 (1H, s), 7.58 (1H, d, J=8 Hz), 7.17 (1H, s), 6.95 (1H, S), 6.74 (1H, d, J=8, Hz), 6.69 (1H, s), 5.23 (2H, s).

Step D: Preparation of 2-(4-Chlorophenyl-2-ethoxy)-4-imidazol-1-ylmethyl-benzonitrile Hydrochloride 4-chlorophenethyl alcohol (0.11 g, 0.67 mmol) and tri-ethylamine (0.37 mL, 2.68 mmol) were dissolved in CH$_2$Cl$_2$ (5 mL) at 0° C. Then it was treated with methanesulfonyl chloride (0.207 mL, 2.68 mmol), with stirring and warming to ambient temperature, until the indicated loss of starting material. The reaction mixture was concentrated in vacuo, then dissolved in DMF (1 mL) and added to a mixture of 2-hydroxy-4-imidazol-1-ylmethyl-benzonitrile (0.10 g, 0.50 mmol) and cesium carbonate (0.33 g, 1.0 mmol) in DMF (2 mL). The reaction mixture was heated at 30° C. for 18 h, then partitioned between EtOAc and $H_2O$, the aqueous layer washed with EtOAc, the organic layers combined, washed with brine, and dried ($Na_2SO_4$). Filtration and concentration to dryness gave the title compound after silica gel chromatography (0.1 to 0.2% $CH_3OH/NH_4OH$ in $CH_2Cl_2$) and conversion to the hydrochloride salt.

FAB mass spectrum (M+1) 338; Analysis calculated for $C_{19}H_{16}N_3OCl.1.3$ HCl.0.75 $H_2O$: C, 57.23; H,4.75; N, 10.54; Found: C, 57.49; H,4.74; N, 10.14.

Using the procedure described above, but substituting the appropriate heterocycle for imidazole in Step C and the appropriate mesylate or halide in Step D, the following compounds were prepared:

2-(3-chlorophenyl-2-ethoxy)-4-imidazol-1-ylmethyl-benzonitrile hydrochloride

FAB mass spectrum (M+1) 338; Analysis calculated for $C_{19}H_{16}N_3OCl.1.2$ HCl.0.35 $H_2O$: C, 58.83; H,4.65; N, 10.83; Found: C, 58.90; H,4.67; N, 10.50.

2-(2-chlorophenyl-2-ethoxy)-4-imidazol-1-ylmethyl-benzonitrile hydrochloride

FAB mass spectrum (M+1) 338.

2-(phenyl-2-ethoxy)-4-imidazol-1-ylmethyl-benzonitrile hydrochloride

FAB mass spectrum (M+1) 304; Analysis calculated for $C_{19}H_{17}N_3O.1.0$ HCl.0.85 $H_2O$: C, 64.25; H, 5.59; N, 11.83; Found: C, 64.55; H, 5.77; N, 11.44.

2-(3-chlorobenzyloxy)-4-imidazol-1-ylmethyl-benzonitrile hydrochloride

FAB mass spectrum (M+1) 324; Analysis calculated for $C_{18}H_{14}ClN_3O.1.2$ HCl.0.40 $H_2O$: C, 57.69; H, 4.30; N, 11.21; Found: C, 57.66; H, 4.31; N, 11.02.

2-(4-chlorobenzyloxy)-4-imidazol-1-ylmethyl-benzonitrile hydrochloride

FAB mass spectrum (M+1) 324.

2-(2,4-dichlorobenzyloxy)-4-imidazol-1-ylmethyl-benzonitrile

FAB mass spectrum (M+1) 358; Analysis calculated for $C_{18}H_{13}Cl_2N_3O.0.10$ $H_2O$: C, 60.04; H, 3.70; N, 11.67; Found: C, 60.02; H, 3.84; N, 11.78.

2-(benzyloxy)-4-imidazol-1-ylmethyl-benzonitrile

Analysis calculated for $C_{18}H_{15}N_3O.0.45$ $H_2O$: C, 72.68; H, 5.39; N, 14.13; Found: C, 73.03; H, 5.13; N, 13.75.

2-(biphenyl-2-ylmethoxy)-4-imidazol-1-ylmethyl-benzonitrile

FAB mass spectrum (M+1) 366; Analysis calculated for $C_{24}H_{19}N_3O.1.1$ HCl.0.85 $H_2O$: C, 68.49; H, 5.22; N, 9.99; Found: C, 68.46; H, 5.24; N, 9.64.

2-(phenyl-4-butoxy)-4-imidazol-1-ylmethyl-benzonitrile hydrochloride

FAB mass spectrum (M+1) 332; Analysis calculated for $C_{21}H_{21}N_3O.1.4$ HCl: C, 65.94; H, 5.90; N, 10.99; Found: C, 65.94; H, 5.78; N, 10.78.

2-(phenyl-3-propoxy)-4-imidazol-1-ylmethyl-benzonitrile hydrochloride

FAB mass spectrum (M+1) 318; Analysis calculated for $C_{20}H_{19}N_3O.1.1$ HCl: C, 67.19; H, 5.67; N, 11.75; Found: C, 67.20; H, 5.43; N, 11.70.

2-(biphenyl-4-yl-2-ethoxy)-4-(1,2,4-triazol-1-yl)methyl-benzonitrile hydrochloride HR mass spectrum theoretical 381.1710; measured 381.1707.

2-(biphenyl-4-yl-2-ethoxy)-4-(2-methyl-imidazol-1-yl) methyl-benzonitrile hydrochloride HR mass spectrum theoretical 394.1910; measured 394.1914.

2-(biphenyl-4-yl-2-ethoxy)-4-benzimidazol-1-yl)methyl-benzonitrile hydrochloride HR mass spectrum theoretical 430.1920; measured 430.1914.

Example 9

Preparation of 4-Imidazol-1-ylmethyl—(2-naphthalen-2-yloxy)-benzonitrile Hydrochloride Step A: Preparation of 4-Bromo-3-fluorobenzoic Acid 4-Bromo-3-fluorotoluene (40.0 g, 0.212 mol) was heated at 90° C. in $H_2O$ (200 mL) and pyridine (200 mL) with mechanical stirring under Ar. Potassium permanganate ($KMnO_4$) (67 g, 0.424 mol) was added portionwise over 3 h. After 4 h, an HPLC of a filtered sample indicated 50% conversion to the acid. An additional 30 g of $KMnO_4$ was added and heating continued overnight. HPLC indicated 81% conversion. Further $KMnO_4$ was added portionwise with reaction monitoring by HPLC until >95% conversion was obtained. The reaction mixture was filtered through Celite, the filter pad washed with $H_2O$, aq NaOH and EtOH. The filtrate was concentrated to a small volume, then partitioned between 3N NaOH solution and diethyl ether. The aqueous basic layer was separated, cooled in an ice-$H_2O$ bath and acidified slowly with 6N HCl solution to precipitate the white solid product. This was collected by suction filtration and dried at 40° C. in a vacuum oven overnight to give the title compound. mp 190–192° C.

$^1$H NMR ($CDCl_3$) d 7.83 (dd, 1H, J=2, 9 Hz), 7.78 (dd, 1H, J=2, 8 Hz), 7.67–7.71 (m, 1H).

Step B: Preparation of 4-Bromo-3-fluorobenzyl Alcohol

4-Bromo-3-fluorobenzoic acid (40.8 g, 0.187 mol) was dissolved in THF (250 ml) with magnetic stirring under Ar in an ice-$H_2O$ bath. The cloudy solution was treated dropwise with borane-THF complex (1 M) (374 mL, 0.374 mol) over a 1 h period maintaining the internal temperature at <10° C. The reaction mixture was left to warm to ambient temperature overnight, then cooled in an ice $H_2O$ bath and treated dropwise with $H_2O$ (150 mL). The THF was removed on a rotary evaporator, and the residue partitioned between EtOAc and $H_2O$. The aqueous layer was extracted with EtOAc (3×100 mL), the organic layers combined, washed with brine, and dried ($Na_2SO_4$), filtered, and concentrated to give the title compound as an oil which solidified on standing.

$^1$H NMR ($CDCl_3$) d 7.52 (t, 1H, J=8 Hz), 7.16 (d, 1H, J=9 Hz), 7.02 (d, 1H, J=8 Hz), 4.67 (s, 2H), 1.47 (br s, 1H).

Step C: Preparation of 2-Fluoro-4-hydroxymethylbenzonitrile

4-Bromo-3-fluorobenzyl alcohol (20 g, 0.097 mol) was dissolved in DMF (100 mL) and then placed under high vacuum for 15 min. The solution was then purged with Ar for 15 min. While purging continued, zinc cyanide (8 g, 0.068 mol) and the catalyst, $Pd[(PPh_3)]_4$, (5.63 g, 0.0049 mol) were added. The reaction mixture was heated at 95° C. under Ar for 18 h, then cooled to ambient temperature and added to $H_2O$. The mixture was extracted with EtOAc, then washed with 1M HCl, $H_2O$, brine, and dried ($Na_2SO_4$). Filtration and concentration to dryness gave the title compound as a white solid after chromatography (silica gel, hexane: EtOAc, 6.5:3.5.

$^1$H NMR ($CDCl_3$) d 7.61 (t, 1H, J=8 Hz), 7.23–7.29 (m, 2H), 4.80 (d, 2H, J=6 Hz), 1.93 (t, 1H, J=6 Hz).

Step D: Preparation of 4-Bromomethyl-2-fluoro-benzonitrile

N-Bromosuccinimide (6.6 g, 0.037 mol) was dissolved in $CH_2Cl_2$ (150 mL), cooled to 0° C. and treated with dimethylsulfide (3.27 mL, 0.0446 mol). The solution was cooled to −20° C. and then treated dropwise with a solution of 2-fluoro-4-hydroxymethylbenzonitrile (3.74 g, 0.0248 mol)

in CH$_2$Cl$_2$ (30 mL). After the addition, the reaction mixture was stirred at 0° C. for 2 h then left to warm to ambient temperature overnight. The reaction mixture was added to ice/H$_2$O, extracted with EtOAc, the organic layer separated, washed with brine and dried (MgSO$_4$). Filtration and concentration to dryness gave the title compound which was purified chromatography (silica gel, 5–10% EtOAc/hexane.

$^1$H NMR (CDCl$_3$) d 7.61 (dd, 1H, J=8, 8 Hz), 7.26–7.30 (m, 2H), 4.45 (s, 2H).

Step E: Preparation of 2-Fluoro-4-imidazol-1-ylmethyl-benzonitrile

4-Bromomethyl-2-fluoro-benzonitrile (3.44 g, 16.0 mmol) and imidazole (5.47 g, 80.3 mmol) were dissolved in DMF (40 mL) and stirred at ambient temperature for 2 h. The DMF was removed in vacuo and the residue was partitioned between EtOAc (300 mL) and aqueous saturated NaHCO$_3$ solution. The organic layer was separated, washed with NaHCO$_3$ solution, H$_2$O, brine, and dried (MgSO$_4$). Filtration and concentration to dryness gave the title compound after chromatography (silica gel, 1–2% CH$_3$OH/CH$_2$Cl$_2$).

$^1$H NMR (CDCl$_3$) d 7.62 (dd, 1H, J=8.5, 9.5 Hz), 7.57 (s, 1H), 7.16 (s, 1H), 7.00 (d, 1H, J=8.5 Hz), 6.94 (d, 1H, J=9.5 Hz), 6.91 (s, 1H), 5.21 (s, 2H).

Step F: Preparation of 2-(2-Naphthyloxy)-4-imidazol-1-ylmethyl-benzonitrile Hydrochloride 2-Fluoro-4-imidazol-1-ylmethyl-benzonitrile (0.167 g, 0.830 mmol), 2-naphthol (0.143 g, 0.996 mmol) and cesium carbonate (0.54 g, 1.66 mmol) were dissolved in DMF (15 mL) and heated at 55° C. under Ar for 18 h. The reaction mixture was partitioned between EtOAc and 1N NaOH solution. The organic layer was separated, washed with 1N NaOH solution, H$_2$O, brine, and dried (MgSO$_4$). Filtration and concentration to dryness gave the title compound after chromatography (silica gel, 1% CH$_3$OH/CH$_2$Cl$_2$).

FAB mass spectrum (M+1) 326; Analysis calculated for C$_{21}$H$_{15}$N$_3$O.1.0 HCl.0.75 H$_2$O: C, 67.19; H, 4.70; N, 11.20; Found: C, 67.23; H, 4.89; N, 11.14.

Using the procedure described above, but substituting the appropriate heterocycle for imidazole in Step E and the appropriate phenol or thiol in Step F, the following compounds were prepared:

2-(3-cyanophenoxy)-4-imidazol-1-ylmethyl-benzonitrile
   FAB mass spectrum (M+1) 301.
2-(3-bromophenoxy)-4-imidazol-1-ylmethyl-benzonitrile
   FAB mass spectrum (M+1) 353.
2-(biphen-3-yloxy)-4-imidazol-1-ylmethyl-benzonitrile
   FAB mass spectrum (M+1) 352.
2-(biphen-4-yloxy)-4-imidazol-1-ylmethyl-benzonitrile
   FAB mass spectrum (M+1) 352.
2-(3-acetylphenoxy)-4-imidazol-1-ylmethyl-benzonitrile
   FAB mass spectrum (M+1) 318.
2-(2-acetylphenoxy)-4-imidazol-1-ylmethyl-benzonitrile
   FAB mass spectrum (M+1) 318.
2-(3-trifluoromethylphenoxy)-4-imidazol-1-ylmethyl-benzonitrile
   FAB mass spectrum (M+1) 344.
2-(3-methylphenoxy)-4-imidazol-1-ylmethyl-benzonitrile
   FAB mass spectrum (M+1) 290.
2-(2-methylphenoxy)-4-imidazol-1-ylmethyl-benzonitrile
   FAB mass spectrum (M+1) 290.
2-(4-methylphenoxy)-4-imidazol-1-ylmethyl-benzonitrile
   FAB mass spectrum (M+1) 290.
2-(3-methoxyphenoxy)-4-imidazol-1-ylmethyl-benzonitrile
   FAB mass spectrum (M+1) 306.
2-(2-methoxyphenoxy)-4-imidazol-1-ylmethyl-benzonitrile
   FAB mass spectrum (M+1) 306.
2-(4-methoxyphenoxy)-4-imidazol-1-ylmethyl-benzonitrile
   FAB mass spectrum (M+1) 306.
2-(3,5-dimethylphenoxy)-4-imidazol-1-ylmethyl-benzonitrile
   FAB mass spectrum (M+1) 304.
2-(3,4-dimethylphenoxy)-4-imidazol-1-ylmethyl-benzonitrile
   FAB mass spectrum (M+1) 304.
2-(3,5-dimethoxyphenoxy)-4-imidazol-1-ylmethyl-benzonitrile
   FAB mass spectrum (M+1) 336.
2-(1-naphthyloxy)-4-imidazol-1-ylmethyl-benzonitrile
   FAB mass spectrum (M+1) 326.
2-(2 4-dichlorophenoxy)-4-imidazol-1-ylmethyl-benzonitrile
   FAB mass spectrum (M+1) 343.
2-(3-fluorophenoxy)-4-imidazol-1-ylmethyl-benzonitrile
   FAB mass spectrum (M+1) 294.
2-(3-t-butylphenoxy)-4-imidazol-1-ylmethyl-benzonitrile
   FAB mass spectrum (M+1) 332.
2-[3-(N,N-diethylamino)phenoxy]-4-imidazol-1-ylmethyl-benzonitrile
   FAB mass spectrum (M+1) 347.
2-(3-N-propylphenoxy)-4-imidazol-1-ylmethyl-benzonitrile
   FAB mass spectrum (M+1) 318.
2-(2,3-dimethoxyphenoxy)-4-imidazol-1-ylmethyl-benzonitrile
   FAB mass spectrum (M+1) 336.
2-(2,3-dimethylphenoxy)-4-imidazol-1-ylmethyl-benzonitrile
   FAB mass spectrum (M+1) 304.
2-(3,4-dimethoxyphenoxy)-4-imidazol-1-ylmethyl-benzonitrile
   FAB mass spectrum (M+1) 336.
2-(2,5-dimethoxyphenoxy)-4-imidazol-1-ylmethyl-benzonitrile
   FAB mass spectrum (M+1) 336.
2-(3,4-dichlorophenoxy)-4-imidazol-1-ylmethyl-benzonitrile
   FAB mass spectrum (M+1) 343.
2-(2,4-dimethylphenoxy)-4-imidazol-1-ylmethyl-benzonitrile
   FAB mass spectrum (M+1) 304.
2-(4-chloro-2-methylphenoxy)-4-imidazol-1-ylmethyl-benzonitrile
   FAB mass spectrum (M+1) 324.
2-(5-chloro-2-methylphenoxy)-4-imidazol-1-ylmethyl-benzonitrile
   FAB mass spectrum (M+1) 324.
2-(2-chloro-4,5-dimethylphenoxy)-4-imidazol-1-ylmethyl-benzonitrile
   FAB mass spectrum (M+1) 338.
2-(5-hydroxymethyl-2-methoxyphenoxy)-4-imidazol-1-ylmethyl-benzonitrile
   FAB mass spectrum (M+1) 336.
4-imidazol-1-ylmethyl-2-(3-phenylamino-phenoxy)-benzonitrile
   FAB mass spectrum (M+1) 367.
4-imidazol-1-ylmethyl-2-[3-(2-methylphenylamino)-phenoxy]-benzonitrile
   FAB mass spectrum (M+1) 81.
4-imidazol-1-ylmethyl-2-(3-phenoxy-phenoxy)-benzonitrile
   FAB mass spectrum (M+1) 368.
2-(2-benzoyl-phenoxy)-4-imidazol-1-ylmethyl-benzonitrile
   FAB mass spectrum (M+1) 380.
1-(5-chloro-2-methoxy-phenyl)-3-[3-(2-cyano-5-imidazol-1-ylmethyl-phenoxy)-phenyl]-urea FAB mass spectrum (M+1) 474.
1-(2,5-dimethoxy-phenyl)-3-[3-(2-cyano-5-imidazol-1-ylmethyl-phenoxy)-phenyl]-urea
  FAB mass spectrum (M+1) 470.
2-(3-benzyloxy-phenoxy)-4-imidazol-1-ylmethyl-benzonitrile
  FAB mass spectrum (M+1) 382.
2-(4-benzyloxy-phenoxy)-4-imidazol-1-ylmethyl-benzonitrile
  FAB mass spectrum (M+1) 382.
2-(2-benzyl-phenoxy)-4-imidazol-1-ylmethyl-benzonitrile
  FAB mass spectrum (M+1) 366.
2-(3-ethynyl-phenoxy)-4-imidazol-1-ylmethyl-benzonitrile
  FAB mass spectrum (M+1) 300.
2-(4-acetyl-3-methyl-phenoxy)-4-imidazol-1-ylmethyl-benzonitrile
  FAB mass spectrum (M+1) 332.
4-imidazol-1-ylmethyl-2-(1H-indazol-6-yloxy)-benzonitrile
  FAB mass spectrum (M+1) 315.
4-imidazol-1-ylmethyl-2-(5,6,7,8-tetrahydro-naphthalen-1-yloxy)-benzonitrile
  FAB mass spectrum (M+1) 330.
4-imidazol-1-ylmethyl-2-(8-oxo-5,6,7,8-tetrahydro-naphthalen-1-yloxy)-benzonitrile
  FAB mass spectrum (M+1) 344.
4-imidazol-1-ylmethyl-2-(1H-indol-7-yloxy)-benzonitrile
  FAB mass spectrum (M+1) 315.
4-imidazol-1-ylmethyl-2-(3-oxo-indan-4-yloxy)-benzonitrile
  FAB mass spectrum (M+1) 330.
4-imidazol-1-ylmethyl-2-(1H-indol-4-yloxy)-benzonitrile
  FAB mass spectrum (M+1) 315.
2-[3-(2-hydroxy-ethoxy)-phenoxy]-4-imidazol-1-ylmethyl-benzonitrile
  FAB mass spectrum (M+1) 336.
4-imidazol-1-ylmethyl-2-(4-imidazol-1-yl-phenoxy)-benzonitrile
  FAB mass spectrum (M+1) 342.
4'-(2-cyano-5-imidazol-1-ylmethyl-phenoxy)-biphenyl-4-carbonitrile
  FAB mass spectrum (M+1) 377.
N-[3-(2-Cyano-5-imidazol-1-ylmethyl-phenoxy)-phenyl]-acetamide
  FAB mass spectrum (M+1) 333.
4-imidazol-1-ylmethyl-2-(9-oxo-9H-fluoren-4-yloxy)-benzonitrile
  FAB mass spectrum (M+1) 378.
2-(5-cyano-2-imidazol-1-ylmethyl-phenoxy)-N-phenyl-benzamide
  FAB mass spectrum (M+1) 395.
2-(5-chloro-pyridin-3-yloxy)-4-imidazol-1-ylmethyl-benzonitrile
  FAB mass spectrum (M+1) 311.
N-[3-(2-Cyano-5-imidazol-1-ylmethyl-phenoxy)-phenyl]-benzenesulfonamide
  FAB mass spectrum (M+1) 431.
4-imidazol-1-ylmethyl-2-(indan-5-yloxy)-benzonitrile
  FAB mass spectrum (M+1) 316.
2-(9H-carbazol-2-yloxy)-4-imidazol-1-ylmethyl-benzonitrile
  FAB mass spectrum (M+1) 365.
4-imidazol-1-ylmethyl-2-(5,6,7,8-tetrahydro-naphthalen-2-yloxy)-benzonitrile
  FAB mass spectrum (M+1) 330.
4-imidazol-1-ylmethyl-2-(2-methoxy-4-propenyl-phenoxy)-benzonitrile
  FAB mass spectrum (M+1) 346.
4-imidazol-1-ylmethyl-2-[4-(3-oxo-butyl)-phenoxy]-benzonitrile
  FAB mass spectrum (M+1) 346.
2-(3-chlorophenoxy)-5-imidazol-1-ylmethyl-benzonitrile hydrochloride
  FAB mass spectrum (M+1) 310.
2-(4-chlorophenoxy)-4-imidazol-1-ylmethyl-benzonitrile hydrochloride
  FAB mass spectrum (M+1) 310.
2-(3,5-dichlorophenoxy)-4-imidazol-1-ylmethyl-benzonitrile hydrochloride
  FAB mass spectrum (M+1) 344.
2-(pyridin-3-yloxy)-4-imidazol-1-ylmethyl-benzonitrile dihydrochloride
  FAB mass spectrum (M+1) 277.
2-(2-chlorophenoxy)-4-imidazol-1-ylmethyl-benzonitrile hydrochloride
  FAB mass spectrum (M+1) 310.
2-(3-chlorophenoxy)-5-(4-phenyl-imidazol-1-ylmethyl)-benzonitrile hydrochloride
  FAB mass spectrum (M+1) 386.
2-(biphen-2-yloxy)-4-imidazol-1-ylmethyl-benzonitrile hydrochloride
  Analysis calculated for $C_{23}H_{17}N_3O.1.0$ HCl.0.75 $H_2O$: C, 68.82; H, 4.90; N, 10.47; Found: C, 68.80; H, 4.91; N, 10.30.
2-(phenoxy)-4-imidazol-1-ylmethyl-benzonitrile hydrochloride
  Analysis calculated for $C_{17}H_{13}N_3O.1.0$ HCl.0.35 $H_2O$: C, 64.19; H, 4.66; N, 13.21; Found: C, 64.33; H, 4.78; N, 12.84.

Example 10

Preparation of 2-(2-Chloro-4-methoxyphenoxy)-4-imidazol-1-ylmethyl-benzonitrile Hydrochloride Step A: Preparation of 2-(2-Chloro-4-methoxyphenoxy)-4-imidazol-1-ylmethyl-benzonitrile Hydrochloride 2-Fluoro-4-imidazol-1-ylmethyl-benzonitrile, as described in Example 9, Step E, (0.118 g, 0.586 mmol), 2-chloro-4-methoxyphenol (0.112 g, 0.703 mmol), KF on alumina (40% by weight) (0.112 g, 0.703 mmol) and 18-crown-6 (0.11 g, 10% by weight of phenol) were dissolved in $CH_3CN$ (5 mL) and heated at reflux under Ar for 18 h. The reaction mixture was filtered, dissolved in $CH_3OH$ and purified by RP HPLC on a Waters Prep Pak column eluting with a 0.1% TFA/$H_2O$: 0.1% TFA/$CH_3CN$ gradient (95:5 to 5:95) to give the title compound after conversion to the hydrochloride salt.

FAB mass spectrum (M+1) 340; Analysis calculated for $C_{18}H_{14}ClN_3O_2.1.0$ HCl.0.15 $CH_2Cl_2$: C, 56.04; H, 3.96; N, 10.80; Found: C, 56.25; H, 3.90; N, 10.42.

Using the procedure described above, but substituting the appropriate heterocycle for imidazole (Example 9, Step E) and the appropriate phenol or thiol in Step A, the following compounds were prepared:
2-(2-chlorophenylsulfanyl)-4-imidazol-1-ylmethyl-benzonitrile hydrochloride
  FAB mass spectrum (M+1) 326.
4-imidazol-1-ylmethyl-2-(naphthalen-2-ylsulfanyl)-benzonitrile
  FAB mass spectrum (M+1) 342.
2-(2,4-dichlorophenylsulfanyl)-4-imidazol-1-ylmethyl-benzonitrile hydrochloride
  FAB mass spectrum (M+1) 360.
Oxidation of this Compound Provided the Sulfoxide:
2-(2,4-dichloro-benzenesulfinyl)-4-imidazol-1-ylmethyl-benzonitrile
  FAB mass spectrum (M+1) 376.
and the sulfone:

2-(2,4-dichloro-benzenesulfonyl)-4-imidazol-1-ylmethyl-benzonitrile
FAB mass spectrum (M+1) 392.
2-(2-methyl-pyridin-3-yloxy)-4-imidazol-1-ylmethyl-benzonitrile
FAB mass spectrum (M+1) 291.
2-(2,4-dimethyl-pyridin-3-yloxy)-4-imidazol-1-ylmethyl-benzonitrile
FAB mass spectrum (M+1) 305.
2-(4-chloro-2-methoxyphenoxy)-4-imidazol-1-ylmethyl-benzonitrile hydrochloride
FAB mass spectrum (M+1) 340.
2-(2-chlorophenoxy)-4-(5-methyl-imidazol-1-ylmethyl)-benzonitrile
FAB mass spectrum (M+1) 324.
2-(2-chlorophenoxy)-4-(4-methyl-imidazol-1-ylmethyl)-benzonitrile hydrochloride
FAB mass spectrum (M+1) 324.
2-(3-chloro-5-trifluoromethyl-pyridin-2-yloxy)-4-imidazol-1-ylmethyl-benzonitrile
FAB mass spectrum (M+1) 471.
2-(2-acetylphenoxy)-4-imidazol-1-ylmethl-benzonitrile hydrochloride
FAB mass spectrum (M+1) 318.
2-(2,4-dichlorophenoxy)-4-(2-methyl-imidazol-1-ylmethyl)-benzonitrile hydrochloride
FAB mass spectrum (M+1) 358.
N-[3-(2-cyano-5-imidazol-1-ylmethyl-phenoxy)-phenyl]-benzamide
Analysis calculated for $C_{24}H_{18}N_4O_2.0.1$ EtOAc: C, 72.67; H, 4.70; N, 13.90; Found: C, 72.70; H, 4.70; N, 13.50.
2-[3-(2-cyano-5-imidazol-1-ylmethyl-phenoxy)-phenyl]-N-phenyl-acetamide
Analysis calculated for $C_{25}H_{20}N_4O_2.0.95 H_2O$: C, 70.55; H, 5.19; N, 13.17; Found: C, 70.52; H, 5.03; N, 12.92.
4-imidazol-1-ylmethyl-2-(quinolin-6-yloxy)-benzonitrile
FAB mass spectrum (M+1) 327.
4-imidazol-1-ylmethyl-2-(2-oxo-1,2-dihydro-quinolin-6-yloxy)-benzonitrile
FAB mass spectrum (M+1) 343.
N-[3-(2-cyano-5-imidazol-1-ylmethyl-phenoxy)-phenyl]-2-phenyl-acetamide
FAB mass spectrum (M+1) 409.
5-(2-cyano-5-imidazol-1-ylmethyl-phenoxy)-N-cyclohexyl-nicotinamide
FAB mass spectrum (M+1) 402.
N-(3-chloro-phenyl)-5-(2-cyano-5-imidazol-1-ylmethyl-phenoxy)-nicotinamide
FAB mass spectrum (M+1) 430.
3-(2-cyano-5-imidazol-1-ylmethyl-phenoxy)-N-ethyl-N-phenyl-benzamide
FAB mass spectrum (M+1) 423.
3-(2-cyano-5-imidazol-1-ylmethyl-phenoxy)-N-cyclopropylmethyl-N-phenyl-benzamide
FAB mass spectrum (M+1) 449.
2-(2,3-dimethoxyphenoxy)-4-(2,4-dimethyl-imidazol-1-ylmethyl)-benzonitrile hydrochloride
FAB mass spectrum (M+1) 364.
4-(2-methyl-imidazol-1-ylmethyl)-2-(naphthalen-2-yloxy)-benzonitrile
FAB mass spectrum (M+1) 340.

Example 11

Preparation of 3-(2-Cyano-5-imidazol-1-ylmethyl-phenoxy)-N-ethyl-N-phenyl-benzamide Trifluroacetate To a solution of 3-(2-cyano-5-imidazol-1-ylmethyl-phenoxy)-N-phenyl-benzamide (0.075 g, 0.19 mmol) in DMF (5.0 ml) was added NaH (0.016 g, 60% disp., 0.38 mmol). The solution was stirred for 10 min. and iodoethane (0.060 mL, 0.76 mmol) was added and the stirring continued for 18 hr. The DMF was removed in vacuo and the residue was partitioned with EtOAc and saturated $NaHCO_3$. The EtOAc layer was washed with $H_2O$, brine, and dried ($MgSO_4$). Filtration and concentration in vacuo gave the title compound after purification on preparative HPLC. FAB mass spectrum m/e 423 (M+1).

Analysis calculated for $C_{26}H_{22}N_4O_2.1.35$ TFA.0.25 $H_2O$: C, 59.33; H, 4.14; N, 9.65; Found: C, 59.33; H, 4.11; N, 9.73.

Using the procedure described above the following compound was prepared:
3-(2-cyano-5-imidazol-1-ylmethyl-phenoxy)-N-cyclopropylmethyl-N-phenyl-benzamide
FAB mass spectrum m/e 449 (M+1).

Example 12

Preparation of 4-(1-Imidazol-1-yl-1-methyl-ethyl)-2-(naphthalen-2-yloxy)-benzonitrile Hydrochloride
Step A: Preparation of 4-(1-Midazol-1-yl-1-methyl-ethyl)-2-(naphthalen-2-yloxy)-benzonitrile Hydrochloride 4-Imidazol-1-ylmethyl-2-(naphthalen-2-yloxy)-benzonitrile hydrochloride (126 mg, 0.348 mmol) was dissolved in dry THF (2 mL) and cooled to −78° C. under argon. Lithium bis(trimethylsilyl)amide (1.31 mL, 1.31 mmol) was added dropwise over 5 min and stirred for 15 min. Methyl iodide (0.086 mL, 1.39 mmol) was added and the mixture stirred at −78° C. for 4 h. The reaction was quenched with sat. $NaHCO_3$ solution (1 mL), warmed to RT, diluted with sat. $NaHCO_3$ solution and extracted with $CH_2Cl_2$ (3×). The combined organic layers were dried ($Na_2SO_4$), concentrated, and purified using $SiO_2$ chromatography (0.5–1.0% MeOH|$CH_2Cl_2$). The oil was dissolved in $CH_2Cl_2$ and treated with 1N HCl ethereal solution to give the title compound.

Example 13

Preparation of 1-[4-iodo-3-(Naphthalen-2-yloxy)-benzyl]-1H-imidazole
Step A: Preparation of 4-Iodo-3-(naphthalen-2-yloxy)-benzoic Acid Methyl Ester A mixture of 3-hydroxy-4-iodo-benzoic acid acid methyl ester (0.505 g, 1.82 mmol), cupric acetate (0.330 g, 1.82 mmol), 2-naphthylboronic acid (0.625 g, 3.63 mmol) and powdered 4A molecular sieves (0.3 g) in $CH_2Cl_2$ (21 mL) was treated with triethylamine (1.27 mL, 9.08 mmol) and stirred at ambient temperature for 18 hr. The reaction mixture was filtered through celite, concentrated to dryness and chromatographed ($SiO_2$, 5–40% EtOAc: hexane) to give the title compound. FAB mass spectrum (M+1) 405.
Step B: Preparation of [4-Iodo-3-(naphthalen-2-yloxy)-phenyl]-methanol 4-Iodo-3-(naphthalen-2-yloxy)-benzoic acid methyl ester (0.10 g, 0.25 mmol) dissolved in THF (2 mL) was treated with $LiBH_4$ (2 M solution in THF) (0.247 mL, 0.495 mmol) and heated at reflux for 1.5 hr. The reaction mixture was cooled, added to $H_2O$ (50 mL)- concd HCl (4.3 mL), and extracted with EtOAc (3×30 mL). The organics were combined, washed with $H_2O$, aq saturated $NaHCO_3$ solution, brine, and dried ($Na_2SO_4$). Filtration and concentration to dryness gave the title compound which was used without purification.
Step C: Preparation of [4-Iodo-3-(naphthalen-2-yloxy)-phenyl]-methyl Bromide To a solution of [4-iodo-3-(naphthalen-2-yloxy)-phenyl]-methanol (0.085 g, 0.226 mmol) in $CH_2Cl_2$ (2 mL) at −15° C. was added a cold (0° C.) solution of N-bromosuccinimide (0.120 g, 0.68 mmol) in dimethyl sulfide (0.060 mL, 0.814 mmol) with stirring. The reaction mixture was allowed to warm to ambient temperature overnight, concentrated to dryness, and chromatographed ($SiO_2$, 10% EtOAc:hexane) to give the title compound which was used without purification.

Step D: Preparation of 1-[4-Iodo-3-(naphthalen-2-yloxy)-benzyl]-1H-imidazole

[4-Iodo-3-(naphthalen-2-yloxy)-phenyl]-methyl bromide (0.226 mmol) and imidazole (0.10 g) were dissolved in DMF (2 mL) and stirred at ambient temperature for 18 hr. The reaction mixture was purified by RP LC on a Vydac column eluting with a gradient of 0.1% $TFA/H_2O$: 0.1% $TFA/CH_3CN$ (95/5:5/95) to give the title compound.

FAB mass spectrum (M+1) 427. Analysis calculated for $C_{20}H_{15}IN_2O \cdot 0.35$ $Et_2O \cdot 0.25$ HCl: C, 55.71; H, 4.10; N, 6.07; Found; C, 55.70; H, 4.07; N, 5.70.

Example 14

Preparation of Acetic Acid 3-[3-(2-chloro-phenoxy)-4-cyano-benzyl]-3H-imidazol-4-ylmethyl Ester Hydrochloride Step A: Preparation of 1-Triphenylmethyl-4-(hydroxymethyl)-imidazole To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the title product as a white.

Step B: Preparation of 1-Triphenylmethyl-4-(acetoxymethyl)imidazole

1-Triphenylmethyl-4-(hydroxymethyl)-imidazole (260 mmol) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. $NaHCO_3$, and brine, then dried ($Na_2SO_4$), filtered, and concentrated in vacuo to provide the title product as a white powder which was sufficiently pure for use in the next reaction.

Step C: Preparation of 1-(4-Cyano-3-fluorobenzyl)-5-(acetoxymethyl)-imidazole Hydrobromide A solution of 1-triphenylmethyl-4-(acetoxymethyl)imidazole (36.72 g, 96.14 mmol) and 4-bromomethyl-2-fluoro-benzonitrile, as described in Example 9, Step D), (20.67 g, 96.14 mmol) in 250 mL of EtOAc was stirred at 60° C. for 20 hours, during which a white precipitate formed. The reaction was cooled to room temperature and filtered to provide the solid imidazolium bromide salt. The filtrate was concentrated in vacuo to a volume of 100 mL, reheated at 60° C. for two hours, cooled to room temperature, and filtered again. The filtrate was concentrated in vacuo to a volume 40 mL, reheated at 60° C. for another two hours, cooled to room temperature, and concentrated in vacuo to provide a pale yellow solid. All of the solid material was combined, dissolved in 300 mL of methanol, and warmed to 60° C. After two hours, the solution was reconcentrated in vacuo to provide a white solid which was triturated with hexane to remove soluble materials. Removal of residual solvents in vacuo provided the title product hydrobromide as a white solid.

Step D: Preparation of Acetic Acid 3-[3-(2-Chloro-phenoxy)-4-cyano-benzyl]-3H-imidazol-4-ylmethyl Ester Hydrochloride To a solution of 1-(4-cyano-3-fluorobenzyl)-5-(acetoxymethyl)-imidazole hydrobromide (0.29 g, 1.06 mmol) in DMF (7.0 mL) was added 2-chlorophenol (0.132 mL, 1.27 mmol) and cesium carbonate (0.691 g, 2.12 mmol). The mixture was heated to 55° C. and stirred for 18 hr. The DMF was removed in vacuo and the residue was partitioned with EtOAc and saturated $NaHCO_3$ solution. The EtOAc layer was washed with $H_2O$, brine, and dried ($MgSO_4$). Filtration and concentration to dryness gave the title compound after chromatography ($SiO_2$, $CH_2Cl_2:CH_3OH$: $NH_4OH/98:2:0.2$) and conversion to the hydrochloride salt.

FAB mass spectrum m/e 382 (M+1). Analysis calculated for C20H16ClN3O3.1.4 HCl: Found: C, 55.50; H, 4.05; N, 9.71. C, 55.55; H, 4.07; N, 9.41.

Example 15

Preparation of 2-(2-Chloro-phenoxy)-4-(5-hydroxymethyl-imidazol-1-ylmethyl)-benzonitrile Hydrochloride To a solution of acetic acid 3-[3-(2-chloro-phenoxy)-4-cyano-benzyl]-3H-imidazol-4-ylmethyl ester hydrochloride (as described in Example 14)(0.112 g, 0.268 mmol) in THF (2.0 mL) was added 1M NaOH (0.536 mL). After 3.5 hr. the reaction was partitioned between EtOAc and saturated $NaHCO_3$ solution. The EtOAc layer was washed with $H_2O$, brine, and dried ($MgSO_4$). Filtration and concentration in vacuo gave the title compound after conversion to the hydrochloride salt.

FAB mass spectrum m/e 340 (M+1). Analysis calculated for $C_{18}H_{14}ClN_3O_2 \cdot 1.0$ HCl$\cdot 0.2$ EtOAc: C, 57.33; H, 4.25; N, 10.67. Found: C, 57.68; H, 3.83; N, 10.65.

Example 16

Preparation of 4-(5-Aminomethyl-imidazol-1-ylmethyl)-2-(2-chloro-phenoxy)-benzonitrile Ditrifluroacetate Step A: Preparation of 4-(5-Azidomethyl-imidazol-1-ylmethyl)-2-(2-chloro-phenoxy)-benzonitrile To a solution of 2-(2-chloro-phenoxy)-4-(5-hydroxymethyl-imidazol-1-ylmethyl)-benzonitrile hydrochloride, as described in Example 15, (0.07 g, 0.186 mmol) in $CH_2Cl_2$ (4.0 mL), and triethylamine (0.078 mL, 0.558 mmol) at 0° C. was added methanesulfonyl chloride (0.016 mL, 0.205 mmol). The cooling bath was removed and the mixture was stirred for 1 hr. To this solution was added sodium azide (0.018 g, 0.277 mmol) in DMF (1.0 mL). After 1 hr. the reaction mixture was partitioned between EtOAc and saturated $NaHCO_3$ solution. The EtOAc layer was washed with $H_2O$, brine, and dried ($MgSO_4$). Filtration and concentration in vacuo gave the title product which was used in the next step without further purification.

Step B: Preparation of 4-(5-Aminomethyl-imidazol-1-ylmethyl)-2-(2-chloro-phenoxy)-benzonitrile Ditrifluroacetate To a solution of 4-(5-azidomethyl-imidazol-1-ylmethyl)-2-(2-chloro-phenoxy)-benzonitrile (0.05 g, 0.137 mmol) in $CH_3OH$ (5.0 mL) under argon was added 10% Pd/C (0.020 g). The mixture was placed under 1 atmosphere of hydrogen and stirred for 18 hr. The mixture was filtered and the $CH_3OH$ was removed in vacuo to give the title compound after purification by preparative HPLC.

FAB mass spectrum m/e 339 (M+1). Analysis calculated for $C_{18}H_{15}ClN_4O.2.2$ HCl.0.1 $H_2O$: C, 45.49; H, 2.97; N, 9.47. Found: C, 45.43; H, 2.92; N, 9.50.

Example 17

Preparation of N-{3-[4-Cyano-3-(2,3-dimethoxy-phenoxy)-benzyl]-3H-imidazol-4-ylmethyl}-2-cyclohexyl-acetamide Hydrochloride Step A: Preparation of 1-(4-Cyano-3-fluorobenzyl)-5-(hydroxymethyl)imidazole To a solution of 1-(4-cyano-3-fluorobenzyl)-5-(acetoxymethyl)imidazole hydrobromide (as described in Example 14, Step C) (31.87 g, 89.77 mmol) in 300 mL of 2:1 THF/water at 0° C. was added lithium hydroxide monohydrate (7.53 g, 179 mmol). After two hours, the reaction was concentrated in vacuo to a 100 mL volume, stored at 0° C. for 30 minutes, then filtered and washed with 700 mL of cold water to provide a brown solid. This material was dried in vacuo over $P_2O_5$ to provide the titled product as a pale brown powder which was sufficiently pure for use in the next step without further purification.

Step B: Preparation of 4-(5-Aminomethyl-imidazol-1-ylmethyl)-2-fluoro-benzonitrile Dihydrochloride Following the procedures described in Example 16 but starting with 1-(4-cyano-3-fluorobenzyl)-5-(hydroxymethyl)imidazole (1.1 g, 4.85 mmol) the title compound was prepared.

Step C: Preparation of N-[3-(4-Cyano-3-fluoro-benzyl)-3H-imidazol-ylmethyl]-2-cyclohexyl-acetamide To a solution of 4-(5-aminomethyl-imidazol-1-ylmethyl)-2-fluoro-benzonitrile dihydrochloride (0.17 g, 0.651 mmol) in DMF (5.0 mL) was added cyclohexylacetic acid (0.11 g, 0.782 mmol), BOP reagent (0.433 g, 0.977 mmol), and NMM (0.28 mL, 2.6 mmol). The mixture was stirred for 18 hr. The DMF was removed in vacuo and the residue was partitioned with EtOAc and saturated $NaHCO_3$ solution. The EtOAc layer was washed with $H_2O$, brine, and dried ($MgSO_4$). Filtration and concentration in vacuo gave the title compound after chromatography (silica gel, $CH_2Cl_2:CH_3OH:NH_4OH/97:3:0.3$).

Step D: Preparation of N-{3-[4-Cyano-3-(2,3-dimethoxy-phenoxy)-benzyl]-3H-imidazol-4-ylmethyl}-2-cyclohexyl-acetamide Hydrochloride To a solution of N-[3-(4-cyano-3-fluoro-benzyl)-3H-imidazol-ylmethyl]-2-cyclohexyl-acetamide (0.16 g, 0.451 mmol) in acetonitrile (7.0 mL) was added 2,3-dimethoxyphenol (0.065 mL, 0.497 mmol), $KF/Al_2O_3$ (0.2 g), and 18-crown-6 (0.032 g). The mixture was refluxed for 20 hr. The acetonitrile was removed in vacuo and the residue was partitioned with EtOAc and saturated $NaHCO_3$. The ethyl acetate layer was washed with H2O, brine, and dried ($MgSO_4$). Removal of the ethyl acetate in vacuo gave the title compound after chromatography (silica gel, $CH_2Cl_2:CH_3OH:NH_4OH/98:2:0$ and conversion to the hydrochloride salt. FAB mass spectrum m/e 489 (M+1).

Example 18

Preparation of 2-(3-Chloro-phenoxy)-4-[(4-chloro-phenyl)-imidazol-1-yl-methyl]-benzonitrile Trifluoroacetate Step A: Preparation of 4-Bromo-3-fluorobenzaldehyde To a well-stirred mixture of 4-bromo-3-fluorobenzyl alcohol (as described in Example 9, Step B) (10.25 g, 0.05 mol), TEMPO (0.781 g, 0.005 mol) and tetrabutylammonium fluoride (1.39 g, 0.005 mol) in $CH_2Cl_2$ (200 mL) and a solution of 0.5M $NaHCO_3$/0.05M $K_2CO_3$ (200 mL) was added N-chlorosuccinimide (9.35 g, 0.07 mol). After 6 hrs, the layers were separated, the aqueous layer back-washed with $CH_2Cl_2$ (2×50 mL), the organics combined and dried ($Na_2SO_4$). The solution was filtered, concentrated to half its volume, then chromatographed (silica gel, $CH_2Cl_2$) to give the title compound.

$^1H$ NMR ($CDCl_3$) δ 9.96 (s, 1H), 7.78 (dd, 1H, J=2, 8 Hz), 7.62 (dd, 1H, J=2, 8 Hz), 7.56 (dd, 1H, J=2, 8 Hz).

Step B: Preparation of (4-Bromo-3-fluoro-phenyl)-(4-chloro-phenyl)-methanol

To a solution of 4-bromo-3-fluorobenzaldehyde (1.6 g, 7.88 mmol) in diethylether (20 mL) at 0° C. was added 4-chlorophenyl-magnesiumbromide (1Mether, 9.46 mL, 9.46 mmol) dropwise via syringe. The cooling bath was removed and after the mixture was stirred for 18 hr it was cooled to 0° C. and saturated $NH_4Cl$ solution (20 mL) was added to quench the reaction. The reaction mixture was partitioned between EtOAc and saturated $NaHCO_3$ solution. The EtOAc layer was washed with $H_2O$, brine, and dried ($MgSO_4$). Filtration and concentration in vacuo gave the title compound as a solid after chromatography (silica gel, hexane:EtOAc/85:15).

Step C: Preparation of (4-Cyano-3-fluoro-phenyl)-(4-chloro-phenyl)-methanol

Following the procedure described in Example 9, Step C, but starting with (4-bromo-3-fluoro-phenyl)-(4-chloro-phenyl)-methanol (2.2 g, 6.97 mmol), the title compound was obtained as a solid.

Step D: Preparation of 4-[(4-Chloro-phenyl)-imidazol-1-yl-methyl]-2-fluoro-benzonitrile To a solution of (4-cyano-3-fluoro-phenyl)—(4-chloro-phenyl)-methanol (2.2 g, 8.79 mmol) in acetonitrile (30 mL) was added CDI (4.28 g, 8.79 mmol) and imidazole hydrochloride (2.75 g, 8.79 mmol) and the mixture was heated at reflux for 3 hr. The acetonitrile was removed in uacuo and the residue was partitioned with EtOAc and saturated $NaHCO_3$ solution. The EtOAc layer was washed with $H_2O$, brine, and dried ($MgSO_4$). Filtration and concentration in vacuo gave the title compound.

Step E: Preparation of 2-(3-Chloro-phenoxy)-4-[(4-chloro-phenyl)-imidazol-1-yl-methyl]-benzonitrile Trifluoroacetate Following the procedure described in Example 11, Step A, but starting with 4-[(4-chloro-phenyl)-imidazol-1-yl-methyl]-2-fluoro-benzonitrile, as described in Step D, (0.06 g, 0.193 mmol) and 3-chlorophenol (0.022 mL, 0.212 mmol), the the title compound was obtained after purification by preparative HPLC.

FAB mass spectrum m/e 420 (M+1). Analysis calculated for $C_{23}H_{15}Cl_2N_3O.1.90$ TFA.0.40 $H_2O$: C, 49.98; H, 2.77; N, 6.52. Found: C, 49.98; H, 2.72; N, 6.36.

Example 19

Preparation of 2-(3-Chloro-phenoxy)-4-[1-(4-chloro-phenyl)-2-hydroxy-1-imidazol-1-yl-ethyl]-benzonitrile Hydrochloride To a solution of 2-(3-chloro-phenoxy)-4-[(4-chloro-phenyl)-imidazol-1-yl-methyl]-benzonitrile trifluoroacetate (0.065 g, 0.122 mmol) in acetonitrile (5 mL) was added 1M KOH (0.5 mL) (pH=9–10) and 37% aqueous formaldehyde (0.14 mL) After stirring for 18 hr the mixture was adjusted to pH=3 with acetic acid, diluted with $CH_3OH$ (3 mL) and purified on prep HPLC. The TFA salt was converted to the HCl salt to obtain the title compound.

FAB mass spectrum m/e 450 (M+1). Analysis calculated for $C_{24}H_{17}Cl_2N_3O_2$.0.4 $CH_2Cl_2$.0.3 $H_2O$: C, 57.13; H, 3.75; N, 8.06. Found: C, 57.13; H, 3.82; N, 7.67.

Example 20

Preparation of 2-(3-Chloro-phenoxy)-4-[(4-chloro-phenyl)-hydroxy-(3H-imidazol-4-yl)-methyl]-benzonitrile Step A: Preparation of (4-Bromo-3-fluoro-phenyl)-(4-chlorophenyl)-methanol 4-Bromo-3-fluorobenzaldehyde (as described in Example 18, Step A) (3.61 g, 17.7 mmol) was dissolved in anhydrous diethyl ether (40 mL). To this solution was added a 1.0M solution of 4-chlorophenyl-magnesium bromide (21.3 mL, 21.3 mmol). After stirring at ambient temperature for 4 hr the reaction was quenched with satd. $NH_4Cl$ and extracted with $Et_2O$. The organic layer was washed with satd $NaHCO_3$ solution, water, brine, dried ($MgSO_4$), concentrated and purified by chromatography ($SiO_2$, 10% EtOAc/hexane) to give the title compound.

Step B: Preparation of (4-Bromo-3-fluoro-phenyl)-(4-chloro-phenyl)-methanone (4-Bromo-3-fluoro-phenyl)-(4-chloro-phenyl)-methanol (2.26 g, 7.16 mmol) and $MnO_2$ (6.22 g, 70.1 mmol) was stirred in $CH_2Cl_2$ (40 mL) for 40 hr. The solution was filtered through a celite pad and concentrated to give the title compound.

Step C: Preparation of (4-Bromo-3-fluoro-phenyl)-(4-chloro-phenyl)-(1-trityl-1H-imidazol-4-yl)-methanol 4-Iodo-1-trityl-1H-imidazole (1.39 g, 3.18 mmol) was dissolved in anhydrous $CH_2Cl_2$ (10 mL). To this solution was added a 3.0M solution of ethylmagnesium bromide (1.11 mL, 3.34 mmol) and stirred under Ar. After 3 hr, a solution of (4-bromo-3-fluoro-phenyl)-(4-chloro-phenyl)-methanone (1.00 g, 3.18 mmol) dissolved in $CH_2Cl_2$ (5 mL) was added dropwise and the resulting solution was stirred overnight. The reaction was quenched with satd. $NH_4Cl$ solution, diluted with satd. $NaHCO_3$ solution to pH=8.5, and extracted with $CH_2C_2$ (3×). The combined organic layers were dried ($MgSO_4$), concentrated and purified using $SiO_2$ chromatography (10–20% EtOAc/Hexane) to yield the title compound.

Step D: Preparation of 4-[(4-Chloro-phenyl)-hydroxy-(1-trityl-1H-imidazol-4-yl)-methyl]-benzonitrile (4-Bromo-3-fluoro-phenyl)-(4-chloro-phenyl)-(1-trityl-1H-imidazol-4-yl)-methanol (0.360 g, 0.578 mmol) and $Zn(CN)_2$ (0.045 g, 0.405 mmol) was stirred in anhydrous DMF (8 mL). The solution was purged with Ar for 10 min, degassed under high vacuum for 5 min, then tetrakis (triphenylphosphine)palladium(0) (0.067 mg, 0.057 mmol) was added and the mixture stirred overnight at 80° C. under Ar. Subsequent additions of $Zn(CN)_2$ and tetrakis (triphenylphosphine)palladium(0) were added to drive the reaction to completion. The reaction was diluted with EtOAc and extracted with satd. $NaHCO_3$ solution, water and brine, dried ($MgSO_4$), concentrated and purified using $SiO_2$ chromatography (0.5% MeOH/$CH_2Cl_2$) to yield the title compound.

Step E: Preparation of 2-(3-Chloro-phenoxy)-4-[(4-chloro-phenyl)-hydroxy-(1-trityl-1H-imidazol-4-yl)-methyl]-benzonitrile 4-[(4-Chloro-phenyl)-hydroxy-(1-trityl-1H-imidazol-4-yl)-methyl]-2-fluoro-benzonitrile (0.337 g, 0.591 mmol), 3-chlorophenol (0.074 mL, 0.709 mmol), 40% KF on alumina (0.182 g), and 18-Crown-6 ether (0.018 g, 0.068 mmol) were refluxed in $CH_3CN$ for 40 hr under Ar. The reaction mixture was concentrated in vacuo, diluted with EtOAc, washed with satd. $NaHCO_3$ solution, water, brine and dried ($MgSO_4$). Filtration and concentration gave the title compound.

Step F: Preparation of 2-(3-Chloro-phenoxy)-4-[(4-chloro-phenyl)-hydroxy-(3H-imidazol-4-yl)-methyl]-benzonitrile 2-(3-Chloro-phenoxy)-4-[(4-chloro-phenyl)-hydroxy-(1-trityl-1H-imidazol-4-yl)-methyl]-benzonitrile (0.269 g, 0.396 mmol), trifluoroacetic acid (5 mL), triethylsilane (0.050 mL, 3.17 mmol) was stirred in $CH_2Cl_2$ (5 mL) under Ar for 2 hr. The reaction mixture was concentrated in vacuo, diluted with EtOAc, washed with satd. $NaHCO_3$ solution, water, brine, dried ($MgSO_4$), concentrated and purified using $SiO_2$ chromatography (1–1.5% MeOH/$CH_2Cl_2$ w $NH_4OH$) to give the title compound. FAB MS (M+1)=436;

Analysis calculated for $C_{23}H_{15}Cl_2N_3O_2$.0.35 $H_2O$: C, 62.41; H, 3.58; N, 9.49. Found: C, 62.38; H, 3.68; N, 9.28.

Example 21

Preparation of 2-(2,4-Dichloro-phenylsulfanyl)-4-[5-(2-morpholin-4-yl-ethyl)-imidazol-1-ylmethyl]-benzonitrile Step A: Preparation of {2-[3-(4-Cyano-3-fluoro-benzyl)-3H-imidazol-4-yl]-ethyl}-carbamic Acid Tert-butyl Ester To a solution of $N^T$-pivaloyloxymethyl-$N^\alpha$-phthaloylhistamine (J. C. Emmett, F. H. Holloway, and J. L. Turner, *J. Chem. Soc., Perkin Trans.* 1, 1341, (1979)) (4.59 g, 0.0124 mmol) in acetonitrile (40 mL) was added 2-fluoro-4-imidazol-1-ylmethyl-benzonitrile (as described in Example 9, Step D) (2.8 g, 0.013 mmol) and the mixture was heated to reflux for 18 hr. A white solid precipitate formed which after cooling to 0° C. was collected by filtration to obtain the quaternary salt. This intermediate was dissolved in EtOH (100 mL), hydrazine (1.46 mL, 0.046 mmol) was added, and the mixture was heated at reflux for 4 hr. A white precipitate was observed and the reaction was cooled to 25° C. Dimethylphthalate (11.4 mL, 0.0699 mmol) was added and the mixture was again refluxed for 18 hr. After cooling to 25° C. the precipitate was removed by filtration and washed with EtOAc. The filtrate was evaporated in vacuo and the residue was dissolved in THF (125 mL) and $H_2O$ (25 mL). To this solution was added solid $Na_2CO_3$ (4.0 g, 0.0377 mmol) and $BOC_2O$ (4.47 g, 0.020 mmol) and the reaction was stirred for 18 hr. The THF was removed in vacuo and the mixture was partitioned with EtOAc and saturated $NaHCO_3$. The EtOAc layer was washed with brine, dried with $MgSO_4$, and evaporated in vacuo to obtain the title product after chromatography (silica gel, $CH_2Cl_2$:MeOH:$NH_4OH$/97:3:0.3.

Step B: Preparation of 4-[5-(2-Amino-ethyl)-imidazol-1-ylmethyl]-2-fluoro-benzonitrile Dihydrochloride A solution of {2-[3-(4-cyano-3-fluoro-benzyl)-3H-imidazol-4-yl]-ethyl}-carbamic acid tert-butyl ester (1.0 g, 0.0029 mmol) in EtOAc (30 mL) was cooled to −20° C. and saturated with HCl gas. The cooling bath was removed and the reaction was stirred for 2 hr. The solvent was removed in vacuo to obtain the title compound which was used without further purification.

Step C: Preparation of 2-Fluoro-4-[5-(2-morpholin-4-yl-ethyl)-imidazol-1-ylmethyl]-benzonitrile To a solution of 4-[5-(2-amino-ethyl)-imidazol-1-ylmethyl]-2-fluoro-benzonitrile dihydrochloride (0.92 g, 0.0029 mmol) in acetonitrile (150 mL) and triethylamine (3.2 mL) was added 2-bromoethyl ether (0.839 mL, 0.0067 mmol) and the mixture was refluxed for 48 hr. The solvents were removed in uacuo and the residue was dissolved in EtOAc which was washed twice with 1M HCl (100 mL). The HCl layers were combined and adjusted to pH=9 with solid $Na_2CO_3$ and extraxcted 3 times with EtOAc. The EtOAc layers were combined and dried with brine and $MgSO4$. Removal of the EtOAc in vacuo yielded the title compound which was used as is in the next step.

Step D: Preparation of 2-(2,4-Dichloro-phenylsulfanyl)-4-[5-(2-morpholin-4-yl-ethyl)-imidazol-1-ylmethyl]-benzonitrile Following the procedure described in Example 11, Step A, the title compound was prepared using 2-fluoro-4-[5-(2-morpholin-4-yl-ethyl)-imidazol-1-ylmethyl]-benzonitrile (0.15 g, 0.477 mmol) and 2,4-dichlorothiophenol (0.086 g, 0.477 mmol).

FAB mass spectrum m/e 473 (M+1). Analysis calculated for $C_{23}H_{22}Cl_2N_4OS.0.85$ TFA.0.3 $H_2O$: C, 51.52; H, 4.11; N, 9.73. Found: C, 51.51; H, 4.29; N, 9.36.

Following the above methods, the following compound was prepared:

2-(2,4-dichloro-phenoxy)-4-[5-(2-morpholin-4-yl-ethyl)-imidazol-1-ylmethyl]-benzonitrile FAB mass spectrum m/e 457 (M+1). Analysis calculated for $C_{23}H_{22}Cl_2N_4O_2.0.4$ $H_2O$: C, 59.34; H, 4.96; N, 12.04. Found: C, 59.32; H, 4.89; N, 11.75.

Example 22

Preparation of 4-[Hydroxy-(3-methyl-3H-imidazol-4-yl)-methyl]-2-(naphthalen-2-yloxy)-benzonitrile Hydrochloride Step A: Preparation of 2-Fluoro-4-formylbenzonitrile 2-Fluoro-4-hydroxymethylbenzonitrile (Example 9, Step C) 10 g, 0,066 mol) and triethylamine (32.3 mL, 0.231 mol) were dissolved in $CH_2Cl_2$ (100 mL)-DMSO (20 mL) at <5° C. with stirring and treated dropwise with a solution of pyridine.$SO_3$ complex (31.5 g, 0.198 mol) in DMSO (70 mL) maintaining the reaction mixture temperature at <10° C. The reaction mixture was stirred at 5° C. for 1 hr after the addition, then at 20° C. for 1 hr, then partitioned between $CH_2Cl_2$ and $H_2O$. The organic layer was separated, washed well with $H_2O$, brine, and dried ($Na_2SO_4$). Filtration and concentration gave the title compound after purification by chromatography (silica gel, hexane: EtOAc, 3:1). $^1H$ NMR ($CDCl_3$) δ 10.06 (d, 1H, J=2 Hz), 7.86 (dd, 1H, J=5, 8 Hz), 7.798 (dd, 1H, J=1, 8 Hz), 7.728 (dd, 1H, J=1, 8 Hz).

Step B: Preparation of 2-Fluoro-4-[hydroxy-(1-trityl-1H-imidazol-4-yl)-methyl]-benzonitrile To a solution of 4-iodo-1-trityl-1H-imidazole (5.00 g, 11.5 mmol) in anhydrous $CH_2Cl_2$ (30 mL) was added a 3.0M solution of ethylmagnesium bromide (6.58 mL, 19.7 mmol) with stirring under Ar. After 3 h, the reaction mixture was cooled to –78° C. and a solution of 2-fluoro-4-formyl-benzonitrile (1.70 g, 11.5 mmol) dissolved in $CH_2Cl_2$ (20 mL) was added dropwise. The reaction was allowed to warm to RT over 2 h, quenched with saturated $NH_4Cl$ solution, diluted with satd. $NaHCO_3$ solution to pH=8.5, and extracted with $CH_2Cl_2$ (3×). The combined organic layers were dried ($MgSO_4$), concentrated and purified using $SiO_2$ chromatography (0–1% MeOH/$CH_2Cl_2$) to yield the title compound.

Step C: Preparation of Acetic Acid (4-Cyano-3-fluoro-phenyl)-(1-trityl-1H-imidazol-4-yl)-methyl Ester 2-Fluoro-4-[hydroxy-(1-trityl-1H-imidazol-4-yl)-methyl]-benzonitrile (4.05 g, 8.81 mmol), pyridine (2.14 mL, 26.4 mmol), and acetic anhydride (12.5 mL, 132 mmol) were stirred in anhydrous DMF (60 mL) for 3 h under Ar. The reaction was concentrated in uacuo, diluted with EtOAc (250 mL), washed with $H_2O$ (2×), brine, dried ($MgSO_4$) and concentrated to give the title compound.

Step D: Preparation of Acetic Acid (4-Cyano-3-fluoro-phenyl)-(3-methyl-3H-imidazol-4-yl)-methyl Ester Acetic acid (4-cyano-3-fluoro-phenyl)-(1-trityl-1H-imidazol-4-yl)-methyl ester (4.60 g, 9.17 mmol) and dimethyl sulfate (0.83 mL, 8.81 mmol) were dissolved in EtOAc (20 mL) and heated at 60° C. overnight under Ar. The reaction was concentrated in vacuo, diluted with MeOH (30 mL), and refluxed for 1 h. Concentrated in vacuo and purified using $SiO_2$ chromatography (0.5–4% MeOH/$CH_2Cl_2$ with $NH_4OH$) to give the title compound.

Step E: Preparation of 2-Fluoro-4-[hydroxy-(3-methyl-3H-imidazol-4-yl)-methyl]-benzonitrile Acetic acid (4-cyano-3-fluoro-phenyl)-(3-methyl-3H-imidazol-4-yl)-methyl ester (1.26 g, 4.59 mmol) and NaOH (5.5 mL, 5.5 mmol) were dissolved in THF (15 mL) and $H_2O$ (25 mL). After 1 h, the reaction was diluted with satd. $NaHCO_3$ solution, extracted with $CH_2Cl_2$ (3×), dried ($MgSO_4$) and concentrated to give the title compound.

Step F: Preparation of 4-[Hydroxy-(3-methyl-3H-imidazol-4-yl)-methyl]-2-(naphthalen-2-yloxy)-benzonitrile Hydrochloride 2-Fluoro-4-[hydroxy-(3-methyl-3H-imidazol-4-yl)-methyl]-benzonitrile (0.099 g, 0.428 mmol), 2-naphthol (0.062 g, 0.4287 mmol) and $Cs_2CO_3$ (0.279 g, 0.856 mmol) were dissolved in anhydrous DMSO (5 mL) and heated at 80° C. under Ar for 1.5 h. The reaction was diluted with EtOAc, washed with satd. $NaHCO_3$ solution, water, and brine. The organic layer was dried ($MgSO_4$), concentrated and purified using $SiO_2$ chromatography (1–2.5% MeOHl/CH2Cl2). The purified compound was dissolved in $CH_2Cl_2$ and treated with 1N HCl ethereal solution to give the title compound.

FAB MS (M+1)=365. Analysis calculated for $C_{22}H_{17}N_3O_2.1.00$ HCl.1.60 $H_2O$: C, 62.81; H, 5.08; N, 9.99 Found: C, 62.81; H, 4.98; N, 10.20.

Example 23

Preparation of 4-[Amino-(3-methyl-3H-imidazol-4-yl)-methyl]-2-(naphthalen-2-yloxy)-benzonitrile 4-[Hydroxy-(3-methyl-3H-imidazol-4-yl)-methyl]-2-(naphthalen-2-yloxy)-benzonitrile (as described in Example 22) (0.219 g, 0.616 mmol) was dissolved in $SOCl_2$ (5 mL) and stirred at RT for 2 h under $Ar_2$. The solution was concentrated in vacuo and azeotroped with $CH_2Cl_2$ (3×). The solid was dissolved in $CHCl_3$ (20 mL) and cooled to –78° C. $NH_{3(g)}$ was bubbled through the solution, and the reaction was stirred for 4 h while warming to RT under Ar. The solution was concentrated in vacuo and the title compound was obtained after purification (RPLC (95/5–5/95 $H_2O/CH_3CN$ with 0.1% TFA, flow=65 mL/min).

Example 24

Preparation of 4-[1-Hydroxy-1-(3-methyl-3H-imidazol-4-yl)-ethyl]-2-(naphthalen-2-yloxy)-benzonitrile Step A: Preparation of 4-(3-methyl-3H-imidazole-4-carbonyl)-2-(naphthalen-2-yloxy)-benzonitrile 2-Fluoro-4-[hydroxy-(3-methyl-3H-imidazol-4-yl)-methyl]-benzonitrile (as described in Example 22, Step E) (0.172 g, 0.743 mmol), 2-naphthol (0.107 g, 0.743 mmol) and $Cs_2CO_3$ (0.727 g, 2.23 mmol) were dissolved in anhydrous DMF (5 mL) and heated at 60° C. under Ar for 2 days. The reaction was diluted with EtOAc, washed with satd. $NaHCO_3$ solution, water, and brine. The organic layer was dried ($MgSO_4$), concentrated and purified using $SiO_2$ chromatography (1–2% MeOH/CH2Cl2) to give the title compound.

Step B: Preparation of 4-[1-Hydroxy-1-(3-methyl-3H-imidazol-4-yl)-ethyl]-2-(naphthalen-2-yloxy)-benzonitrile 4-(3-Methyl-3H-imidazole-4-carbonyl)-2-(naphthalen-2-yloxy)-benzonitrile (0.109 g, 0.308 mmol) was dissolved in anhydrous THF (5 mL) and a 3.0 M solution of MeMgBr (0.35 mL, 1.05 mmol) was added and stirred at RT. The reaction was quenched with $NH_4Cl$ after 1 h, concentrated, diluted with EtOAc, washed with satd. $NaHCO_3$ solution, water, brine, dried ($MgSO_4$) and concentrated to give the title compound. FT/ICR MS (M+1)=370.

Analysis calculated for $C_{23}H_{19}N_3O_2$.0.40 EtOAc.0.05 $H_2O$: C, 72.85; H, 5.54; N, 10.36 Found: C, 72.87; H, 5.31; N, 10.29.

Example 25

Preparation of 4-[1-Amino-1-(3-methyl-3H-imidazol-4-yl)-ethyl]-2-(naphthalen-2-yloxy)-benzonitrile Hydrochloride 4-[1-Hydroxy-1-(3-methyl-3H-imidazol-4-yl)-ethyl]-2-(naphthalen-2-yloxy)-benzonitrile (as described in Example 24) (0.068 g, 0.184 mmol) was dissolved in $SOCl_2$ (5 mL) and stirred at RT for 1.5 h. The solution was concentrated in vacuo and azeotroped with anhydrous $CH_2Cl_2$ (3×). The solid was dissolved in $CHCl_3$ (5 mL) and cooled to −78° C. $NH_{3(g)}$ was bubbled through the solution and stirred for 4 h while warming to RT under Ar. The solution was concentrated in vacuo and purified using reverse phase chromatography (95/5–5/95 $H_2O/CH_3CN$ with 0.1% TFA, flow=65 mL/min). The compound was converted to its free base using saturated $NaHCO_3$ solution, extracted with $CH_2Cl_2$ (3×), dried ($MgSO_4$), filtered and treated with 1N HCl ethereal solution to give the title compound. FT/ICR MS (M+1)=369.

Using the method described above, but substituting 3-{2-cyano-5-[1-hydroxy-1-(3-methyl-3H-imidazol-4-yl)-ethyl]-phenoxy}-N-ethyl-N-phenyl-benzamide (as described in Example 26, Step C), the following compound was prepared:
3-{2-cyano-5-[1-amino-1-(3-methyl-3H-imidazol-4-yl)-ethyl]-phenoxy}-N-ethyl-N-phenyl-benzamide.

FT/ICR MS (M+1)=466 Analysis calculated for $C_{28}H_{27}N_5O_2$.0.15 $H_2O$: C, 71.81; H, 5.88; N, 14.96; Found: C, 71.86; H, 5.59; N, 14.78.

Example 26

Preparation of 3-{2-Cyano-5-[1-hydroxy-1-(3-methyl-3H-imidazol-4-yl)-ethyl]-phenoxy}-N-ethyl-N-phenyl-benzamide Step A: Preparation of 2-Fluoro-4-(3-methyl-3H-imidazole-4-carbonyl)-benzonitrile 2-Fluoro-4-[hydroxy-(3-methyl-3H-imidazol-4-yl)-methyl]-benzonitrile (as described in Example 22, Step E) (0.655 g, 2.83 mmol) and $MnO_2$ (1.23 g, 14.2 mmol) were stirred in $CH_2Cl_2$ (50 mL) and $CH_3CN$ (5 mL) for 72 h. The solution was filtered and concentrated to yield the title compound.

Step B: Preparation of 2-Fluoro-4-[1-hydroxy-1-(3-methyl-3H-imidazol-4-yl)-ethyl]-benzonitrile 2-Fluoro-4-(3-methyl-3H-imidazole-4-carbonyl)-benzonitrile (0.603 g, 2.63 mmol) was dissolved in anhydrous THF (30 mL). A solution of 3.0M MeMgBr in diethyl ether (2.55 mL, 7.65 mmol) was added and stirred for 15 min. The reaction was quenched with $NH_4Cl$ solution, diluted with $CH_2Cl_2$ and saturated $NaHCO_3$ solution and seperated. The aqueous layer was back extracted with $CH_2Cl_2$ (3×), the combined organic layers dried ($MgSO_4$) and concentrated to give the title compound.

Step C: Preparation of 3-{2-Cyano-5-[1-hydroxy-1-(3-methyl-3H-imidazol-4-yl)-ethyl]-phenoxy}-N-ethyl-N-phenyl-benzamide 2-Fluoro-4-[1-hydroxy-1-(3-methyl-3H-imidazol-4-yl)-ethyl]-benzonitrile (0.054 g, 0.220 mmol), N-ethyl-3-hydroxy-N-phenyl-benzamide (0.053 g, 0.220 mmol) and $Cs_2CO_3$ (0.143 g, 0.440 mmol) were dissolved in anhydrous DMF (5 mL) and heated at 60° C. under Ar for 4 days. The reaction was diluted with EtOAc, washed with satd. $NaHCO_3$ solution, water, and brine. The organic layer was dried ($MgSO_4$), concentrated and purified using $SiO_2$ chromatography (1–3% $MeOH/CH_2Cl_2$) to give the title compound. FAB MS (M+1)=467.

Analysis calculated for $C_{28}H_{26}N_4O_2$.0–65 $H_2O$: C, 70.31; H, 5.75; N, 11.72 Found: C, 70.31; H, 5.65; N, 11.77.

Using the procedures described above but substituting the requisite phenol in Step C, the following compounds were prepared:
4-[1-hydroxy-1-(3-methyl-3H-imidazol-4-yl)-ethyl]-2-(3-phenylamino-phenoxy)-benzonitrile
FAB MS (M+1)=411.
4-[1-hydroxy-1-(3-methyl-3H-imidazol-4-yl)-ethyl]-2-(3-phenoxy-phenoxy)-benzonitrile
FAB MS (M+1)=412.
2-(3-benzoyl-phenoxy)-4-[1-hydroxy-1-(3-methyl-3H-imidazol-4-yl)-ethyl]-benzonitrile
FAB MS (M+1)=424.
2-(3-tert-butyl-phenoxy)-4-[1-hydroxy-1-(3-methyl-3H-imidazol-4-yl)-ethyl]benzonitrile
FAB MS (M+1)=376.
2-(3-diethylamino-phenoxy)-4-[1-hydroxy-1-(3-methyl-3H-imidazol-4-yl)-ethyl]-benzonitrile
FAB MS (M+1)=391.

Example 27

Preparation of 2-(5-Chloro-2-oxo-2H-[1,2'] bipyridinyl-5'-ylmethoxy)-4-imidazol-1-ylmethyl-benzonitrile Step A: Preparation of 5-Chloro-5'-methyl-[1,2']bipyridinyl-2-one 5-Chloro-2-pyridinol (2.26 g, 17.4 mmol), 2-bromo-5-methylpyridine (3.00 g, 17.4 mmol), copper (0.022 g, 0.35 mmol) and $K_2CO_3$ (2.66 g, 19.2 mmol) were heated at 180° C. for 16 hrs. The brown reaction mixture was cooled, diluted with EtOAc and washed with saturated $NaHCO_3$. The aqueous layer was extracted with EtOAc (2×) and the combined organic extracts were washed with brine, dried ($Na_2SO_4$) and evaporated in vacuo. The residue was chromatographed (silica gel, EtOAc: $CH_2Cl_2$ 20:80 to 50:50 gradient elution) to afford the title compound as a white solid.

$^1$H NMR (400 MHz, $CDCl_3$) δ 8.37 (s, 1H), 7.96(d, J=3.0 Hz, 1H), 7.83 (d, J=8.4 Hz, 1H), 7.65 (dd, J=2.4 and 8.2 Hz, 1H), 7.32 (dd, J=2.9 and 9.7 Hz, 1H), 6.61 (d, J=9.7 Hz, 1H) and 2.39 (s, 3H)ppm.

Step B: Preparation of 5'-Bromomethyl-5-chloro-[1,2'] bipyridinyl-2-one

A solution of 5-chloro-5'-methyl-[1,2']bipyridinyl-2-one (as described in Step A above) (1.00 g, 4.53 mmol), N-bromosuccinimide (0.81 g, 4.53 mmol) and AIBN (0.030 g, 0.18 mmol) in $CCl_4$ (40 mL) was heated at reflux for 2 hrs. The solids were filtered and the filtrate collected. The solvent was evaporated in vacuo and the residue chromatographed (silica gel, EtOAc: $CH_2Cl_2$ 25:75 to 50:50 gradient elution) to afford the title bromide.

$^1$H NMR (400 MHz, CDCl$_3$) δ 8.55 (s, 1H), 8.04 (d, J=2.9 Hz, 1H), 8.01 (d, J=8.4 Hz, 1H), 7.88 (dd, J=2.4 and 8.6 Hz, 1H), 7.34 (dd, J=2.9 and 9.8 Hz, 1H), 6.61 (d, J=9.9 Hz, 1H) and 4.51 (s, 2H) ppm.

Step C: Preparation of 2-(5-Chloro-2-oxo-2H-[1,2']bipyridinyl-5'-ylmethoxy)-4-imidazol-1-ylmethyl-benzonitrile Cesium carbonate (0.123 g, 0.376 mmol) was added to a solution of 2-hydroxy-4-imidazol-1-ylmethyl-benzonitrile (as described in Example 4, Step F) (0.050 g, 0.25 mmol) and 5'-bromomethyl-5-chloro-[1,2']bipyridinyl-2-one (Step H) (0.079 g, 0.263 mmol) in anhydrous DMF (5 mL) and stirred at ambient temperature overnight. The reaction mixture was partitioned between EtOAc and aqueous saturated NaHCO$_3$ solution, the organic layer separated, washed with H$_2$O, brine and dried (MgSO$_4$). Filtration and concentration to dryness gave the title compound after chromatography (silica gel, 1–4% CH$_3$OH/CH$_2$Cl$_2$). FAB MS 418 (M+1).

Example 28

Preparation of 4-Imidazol-1-ylmethyl-2-[2-(2-oxo-2H-pyridin-1-yl)-phenoxy]-benzonitrile Step A: Preparation of 2-(2-Oxo-2H-pyridin-1-yl)-anisole 2-Iodoanisole (1.30 mL, 0.01 mol), 2-hydroxypyridine (0.95 g, 0.01 mol), anhydrous K$_2$CO$_3$ (2.76 g, 0.02 mol) and copper powder (0.0636 g, 0.001 mol) were combined and heated at 200° C. for 2 hr. The reaction mixture was cooled, EtOAc added, and filtered. The filtrate was washed with H$_2$O, aqueous saturated NaHCO$_3$ solution, brine, and dried (Na$_2$SO$_4$). Filtration and concentration gave the title compound after chromatography (silica gel, 2% CH$_3$OH, CH$_2$Cl$_2$).

$^1$H NMR (CDCl$_3$) δ 7.36–7.44 (m, 2H), 7.25–7.29 (m, 1H), 7.18–7.22 (m, 1H), 7.03–7.08 (m, 2H), 6.65 (d, 1H, J=10 Hz), 6.195 (td, 1H, J=1, 7 Hz), 3.82 (s, 3H).

Step B: Preparation of 2-(2-Oxo-2H-pyridin-1-yl)-phenol

Sodium ethanethiol (0.108 g, 1.29 mmol) was added to a solution of 2-(2-oxo-2H-pyridin-1-yl)-anisole (0.100 g, 0.497 mmol) in DMF (2 mL), and the reaction mixture was heated at 100° C. for 3 hr. The reaction mixture was partitioned between CHCl$_3$ and saturated aqueous ammonium chloride and treated with 8N HCl (pH=1). The organic layer was separated, washed with H$_2$O, brine, dried (Na$_2$SO$_4$), filtered, concentrated, and taken up in EtOAc, then extracted with 2% NaOH solution. The aqueous basic layer was acidified with 10% HCl solution, then extracted with EtOAc, the organic layer washed with brine, dried (Na$_2$SO$_4$), filtered, and concentrated to give the desired product.

Step C: Preparation of 4-Imidazol-1-ylmethyl-2-[2-(2-oxo-2H-pyridin-1-yl)-phenoxy]-benzonitrile 2-Fluoro-4-imidazol-1-ylmethyl-benzonitrile (as described in Example 9, Step E) (0.0276 g, 0.137 mmol), 2-(2-oxo-2H-pyridin-1-yl)-phenol (0.0257 g, 0.137 mmol) and cesium carbonate (0.089 g, 0.274 mmol) were combined in DMF (1.2 mL) and heated at 70° C. for 18 hr. The title compound was obtained after RP HPLC on a Waters Prep Pak column eluting with a 0.1% TFA/H$_2$O: 0.1% TFA/CH$_3$CN gradient followed by conversion to the free base.

FAB MS 369 (M+1). Analysis calculated for C$_{22}$H$_{16}$N$_4$O$_2$.0.3 Et$_2$O: C, 71.33; H, 4.90; N,14.34. Found: C, 71.36; H, 4.83; N, 14.31.

Using the procedures described above, but using the appropriate iodoanisole in Step C, the following compound is prepared:

4-Imidazol-1-ylmethyl-2-[3-(2-oxo-2H-pyridin-1-yl)-phenoxy]-benzonitrile

FAB MS 369 (M+1).

Example 29

In vitro Inhibition of Ras Farnesyl Transferase

Assays of farnesyl-protein transferase. Partially purified bovine FPTase and Ras peptides (Ras-CVLS, Ras-CVIM and Ras-CAIL (SEQ.ID.NO.: 12) were prepared as described by Schaber et al., *J. Biol. Chem.* 265:14701–14704 (1990), Pompliano, et al., *Biochemistry* 31:3800 (1992) and Gibbs et al., *PNAS* U.S.A. 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention described in the above Examples were tested for inhibitory activity against human FPTase by the assay described above and were found to have IC$_{50}$ of <50 μM.

Example 30

Modified in vitro GGTase Inhibition Asssay

The modified geranylgeranyl-protein transferase inhibition assay is carried out at room temperature. A typical reaction contains (in a final volume of 50 μL): [$^3$H] geranylgeranyl diphosphate, biotinylated Ras peptide, 50 mM HEPES, pH 7.5, a modulating anion (for example 10 mM glycerophosphate or 5 mM ATP), 5 mM MgCl$_2$, 10 μM ZnCl$_2$, 0.1% PEG (15–20,000), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 13). Reactions are initiated by the addition of GGTase and stopped at timed intervals (typically 15 min) by the addition of 200 μL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. $IC_{50}$ values are determined with Ras peptide near $K_M$ concentrations. Enzyme and nonsaturating substrate conditions for inhibitor $IC_{50}$ determinations are as follows: 75 pM GGTase-I, 1.6 μM Ras peptide, 100 nM geranylgeranyl diphosphate.

Example 31

Cell-based in vitro Ras Prenylation Assay

The cell lines used in this assay consist of either Rat1 or NIH3T3 cells transformed by either viral H-ras; an N-ras chimeric gene in which the C-terminal hypervariable region of viral-H-ras was substituted with the corresponding region from the N-ras gene; or ras-CVLL, a viral-H-ras mutant in which the C-terminal exon encodes leucine instead of serine, making the encoded protein a substrate for geranylgeranylation by GGTase-I. The assay can also be performed using cell lines transformed with human H-ras, N-ras or K4B-ras. The assay is performed essentially as described in DeClue, J. E. et al., Cancer Research 51:712–717, (1991). Cells in 10 cm dishes at 50–75% confluency are treated with the test compound(s) (final concentration of solvent, methanol or dimethyl sulfoxide, is 0.1%). After 4 hours at 37° C., the cells are labelled in 3 ml methionine-free DMEM supplemented with 10% regular DMEM, 2% fetal bovine serum, 400 μCi[$^{35}$S]methionine (1000 Ci/mmol) and test compound (s). Cells treated with lovastatin, a compound that blocks Ras processing in cells by inhibiting the rate-limiting step in the isoprenoid biosynthetic pathway (Hancock, J. F. et al. Cell, 57:1167 (1989); DeClue, J. E. et al. Cancer Res., 51:712 (1991); Sinensky, M. et al. J. Biol. Chem., 265:19937 (1990)), serve as a positive control in this assay. After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Alternatively, four hours after the additon of the labelling media, the media is removed, the cells washed, and 3 ml of media containing the same or a different test compound added. Following an additional 16 hour incubation, the lysis is carried out as above. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., J. Virol. 43:294–304, (1982)). Following a 2 hour antibody incubation at 4° C., 200 μl of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to prenylated and nonprenylated Ras proteins are compared to determine the percent inhibition of prenyl transfer to protein.

Example 32

Cell-based in vitro Anchorage Independent Growth Assay (SALSA)

SALSA (Soft Agar-Like Surrogate Assay) measures the inhibition of anchorage-independent growth by prenyl-transferase inhibitors. Only transformed cells are able to grow anchorage-independently in the SALSA format. Additionally, cells growing in the SALSA format grow in clumps, resembling the colonies formed in soft agar. SALSA may been used to measure the growth inhibition by prenyltransferase inhibitors in a variety of transformed cell lines, including Rat1 fibroblasts transformed with viral-H-ras (H-ras/rat1), as well as a panel of human tumor cell lines (HTL's).

SALSA is performed in 96-well plates that are coated with a thin film of the polymer, PolyHEMA (Poly(2-hydroxyethyl methacrylate)), which prevents cells from attaching to the plate. Rat1 fibroblast cells transformed with v-Ha-ras (this cell line has been deposited in the ATCC on Aug. 19, 1997 under the terms of the Budapest convention and has been given a designation of ATCC CRL 12387) are seeded at 5000 cells/well, grown for 4 hr, then vehicle or half-log dilutions of test compound (in either an 8 or 12 point titration) are added. The cells are then grown for 6 days at 37 degrees, without changing the growth media or adding fresh compound. At day 6, cell growth is assessed via a colorimetric assay that measures the cleavage of the tetrazolium dye, MTT, to an insoluble purple formazan, a reaction dependent upon mitochondrial dehydrogenases. At day 6, the cells are incubated for 4 hr with 0.5 mg/ml MTT, and then SDS is added to 9% w/v to lyse the cells and solubilize the insoluble MTT-formazan. The amount of MTT metabolism is quantitated via spectrophotometric detection at 570 nM. Dose-inhibition curves and $IC_{50}$'s are determined.

Example 33

Construction of SEAP Reporter Plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI was constructed by Deborah Jones (Merck) and contains 5 sequential copies of the 'dyad symmetry response element' cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR1 and HpaI. The ends of the linear DNA fragments were filled in with the Klenow fragment of E. coli DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme BglII and the ends filled in with Kienow DNA Polymerase I. The SEAP DNA fragment was blunt end ligated into the pCMV-RE-AKI vector and the ligation products were transformed into DH5-alpha E. coli cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Cloning of a Myristylated Viral-H-ras Expression Plasmid

A DNA fragment containing viral-H-ras can be PCRed from plasmid "H-1" (Ellis R. et al. J. Virol. 36, 408, 1980) using the following oligos.

Sense Strand:
5'TCTCCTCGAGGCCACCATGGGGAGTAG-CAAGAGCAAGCCTAA GGACCCCAGC-CAGCGCCGGATGACAGAATACAAGCT-TGTGGTG G 3'. (SEQ.ID.NO.: 14).
Antisense: 5'CACATCTAGATCAGGACAGCACA-GACTTGCAGC 3'. (SEQ.ID.NO.: 15)

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site.To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3'end. The XhoI-XbaI fragment can be ligated into the mammalian expression plasmid pCI (Promega) cut with XhoI and XbaI. This results in a plasmid in which the recombinant myr-viral-H-ras gene is constitutively transcribed from the CMV promoter of the pCI vector.

Cloning of a Viral-H-ras-CVLL Expression Plasmid

A viral-H-ras clone with a C-terminal sequence encoding the amino acids CVLL can be cloned from the plasmid "H-1" (Ellis R. et al. J. Virol. 36, 408, 1980) by PCR using the following oligos.

Sense Strand:
5'TCTCCTCGAGGCCACCATGACAGAATACAAG v CTTGTGGTGG-3' (SEQ.ID.NO.: 16).
Antisense strand:
5'CACTCTAGACTGGTGTCAGAGCAGCACACA CTTGCAGC-3' (SEQ.ID.NO.: 17)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid in which the mutated viral-H-ras-CVLL gene is constitutively transcribed from the CMV promoter of the pCI vector.

Cloning of c-H-ras-Leu61 Expression Plasmid

The human c-H-ras gene can be PCRed from a human cerebral cortex cDNA library (Clontech) using the following oligonucleotide primers.

Sense Strand:
5'-GAGAGAATTCGCCACCATGACGGAATATAAG CTGGTGG-3' (SEQ.ID.NO.: 18).
Antisense Strand:
5'-GAGAGTCGACGCGTCAGGAGAGCACACACT TGC-3' (SEQ.ID.NO.: 19).

The primers will amplify a c-H-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-H-ras fragment can be ligated ligated into an EcoRI-Sal I cut mutagenesis vector pAlter-1 (Promega). Mutation of glutamine-61 to a leucine can be accomplished using the manufacturer's protocols and the following oligonucleotide:
5'-CCGCCGGCCTGGAGGAGTACAG-3' (SEQ.ID.NO.: 20).

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid will constitutively transcribe c-H-ras-Leu61 from the CMV promoter of the pCI vector.

Cloning of a c-N-ras-Val-12 Expression Plasmid

The human c-N-ras gene can be PCRed from a human cerebral cortex cDNA library (Clontech) using the following oligonucleotide primers.

Sense Strand:
5'-GAGAGAATTCGCCACCATGACTGAGTACAAA CTGGTGG-3' (SEQ.ID.NO.: 21).
Antisense Strand:
5'-GAGAGTCGACTTGTTACATCACCACACATGGC-3' (SEQ.ID.NO.: 22).

The primers will amplify a c-N-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-N-ras fragment can be ligated into an EcoRI-Sal I cut mutagenesis vector pAlter-1 (Promega). Mutation of glycine-12 to a valine can be accomplished using the manufacturer's protocols and the following oligonucleotide:
5'-GTTGGAGCAGTTGGTGTTGGG-3' (SEQ.ID.NO.: 23).

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid will constitutively transcribe c-N-ras-Val-12 from the CMV promoter of the pCI vector.

Cloning of a c-K-ras-Val-12 Expression Plasmid

The human c-K-ras gene can be PCRed from a human cerebral cortex cDNA library (Clontech) using the following oligonucleotide primers.

Sense Strand:
5'-GAGAGGTACCGCCACCATGACTGAATATAAA CTTGTGG-3' (SEQ.ID.NO.: 24)
Antisense Strand:
5'-CTCTGTCGACGTATTTACATAATTACACACTT TGTC-3' (SEQ.ID.NO.: 25).

The primers will amplify a c-K-ras encoding DNA fragment with the primers contributing an optimized 'Kozak' translation start sequence, a KpnI site at the N-terminus and a Sal I stite at the C-terminal end. After trimming the ends of the PCR product with Kpn I and Sal I, the c-K-ras fragment can be ligated into a KpnI-Sal I cut mutagenesis vector pAlter-1 (Promega). Mutation of cysteine-12 to a valine can be accomplished using the manufacturer's protocols and the following oligonucleotide:
5'-GTAGTTGGAGCTGTTGGCGTAGGC-3' (SEQ.ID.NO.: 26).

After selection and sequencing for the correct nucleotide substitution, the mutated c-K-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K-ras-Val-12 from the CMV promoter of the pCI vector.

SEAP Assay

Human C33A cells (human epitheial carcenoma—ATTC collection) are seeded in 10 cm tissue culture plates in DMEM+10% fetal calf serum+1×Pen/Strep+1×glutamine+1×NEAA. Cells are grown at 37° C. in a 5% $CO_2$ atmosphere until they reach 50–80% of conflunecy.

The transient transfection is performed by the $CaPO_4$ method (Sambrook et al., 1989). Thus, expression plasmids for H-ras, N-ras, K-ras, Myr-ras or H-ras-CVLL are co-precipitated with the DSESEAP reporter construct. For 10 cm plates 600 µl of $CaCl_2$-DNA solution is added dropwise while vortexing to 600 µl of 2×HBS buffer to give 1.2 ml of precipitate solution (see recipes below). This is allowed to sit at room temperature for 20 to 30 minutes. While the precipitate is forming, the media on the C33A cells is replaced with DMEM (minus phenol red; Gibco cat. #31053-028)+0.5% charcoal stripped calf serum+1×(Pen/Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+1×(Pen/Strep, Glutamine and NEAA). Transfected cells are plated in a 96 well microtiter plate (100 µl/well) to which drug, diluted in media, has already been added in a volume of 100 µl. The final volume per well is 200 µl with each drug concentration repeated in triplicate over a range of half-log steps.

Incubation of cells and drugs is for 36 hrs at 37° under $CO_2$. At the end of the incubation period, cells are examined microscopically for evidence of cell distress. Next, 100 µl of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 µl media is combinRased with 200 µl of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

| DNA-$CaPO_4$ precipitate for 10 cm. plate of cells | |
|---|---|
| Ras expression plasmid (1 µg/µl) | 10 µl |
| DSE-SEAP Plasmid (1 µg/µl) | 2 µl |
| Sheared Calf Thymus DNA (1 µg/µl) | 8 µl |

| -continued | |
|---|---|
| DNA-$CaPO_4$ precipitate for 10 cm. plate of cells | |
| 2M $CaCl_2$ | 74 µl |
| $dH_2O$ | 506 µl |

2×HBS Buffer
  280 mM NaCl
  10 mM KCl
  1.5 mM $Na_2HPO_4 2H_2O$
  12 mM dextrose
  50 mM HEPES
  Final pH=7.05
Luminesence Buffer (26 ml)
  Assay Buffer 20 ml
  Emerald Reagent™ (Tropix) 2.5 ml
  100 mM homoarginine 2.5 ml
  CSPD Reagent® (Tropix) 1.0 ml
Assay Buffer
  Add 0.05M $Na_2CO_3$ to 0.05M $NaHCO_3$ to obtain pH 9.5. Make 1 mM in $MgCl_2$ Example 34

In Vivo Tumor Growth Inhibition Assay (nude mouse)

In vivo efficacy as an inhibitor of the growth of cancer cells may be confirmed by several protocols well known in the art. Examples of such in vivo efficacy studies are described by N. E. Kohl et al. (*Nature Medicine*, 1:792–797 (1995)) and N. E. Kohl et al. (*Proc. Nat. Acad. Sci. U.S.A.*, 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, compound combination or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. A compound of formula A:

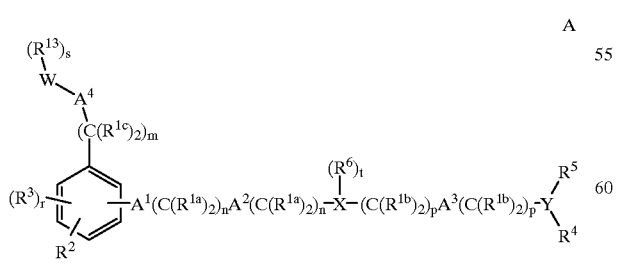

wherein:

$R^{1a}$, $R^{1b}$ and $R^{1c}$ are independently selected from:
a) hydrogen,
b) unsubstituted or substituted aryl, unsubstituted or substituted morpholinyl, $C_3$–$C_{10}$ cycloalkyl, $C_2$–$C_6$ alkenyl, $C_2$–$C_6$ alkynyl, $R^8O$—, $R^9S(O)_q$, CN, $NO_2$, $R^8C(O)$—, $R^8OC(O)$—, $R^8(C_1$–$C_6$ alkyl)O—, $N_3$ or $N(R^8)_2$;
c) $C_1$–$C_6$ alkyl, unsubstituted or substituted by aryl, morpholinyl, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N_3$, or $R^8C(O)O$—;

$R^2$ is CN;

$R^3$, $R^4$ and $R^5$ are independently selected from:
H, CN, $NO_2$, halogen, unsubstituted or substituted $C_1$–$C_6$ alkyl, $N_3$, $R^9S(O)_q$, HC≡C—, unsubstituted or substituted aryl, unsubstituted or substituted morpholinyl, $CF_3$, $CF_3O$—, $CF_3CH_2O$—, $C_3$–$C_{10}$ cycloalkyl, $OR^8$, $N(R^8)_2$, —$C(O)R^8$, —$O(C_1$–$C_6$ alkyl)$OR^8$, —$NHC(O)R^8$, aralkyl, —$(C_1$–$C_6$ alkyl)

OR$^8$, —(C$_1$–C$_6$ alkyl)C(O)R$^8$, —CH=CH—R$^8$ and $$-\underset{OH}{\overset{|}{C}}=\overset{H}{\overset{|}{C}}-R^8;$$

R$^6$ is independently selected from:
  a) hydrogen,
  b) CN,
  c) NO$_2$,
  d) halogen,
  e) aryl, unsubstituted or substituted,
  f) C$_1$–C$_6$ alkyl, unsubstituted or substituted,
  g) R$^8$O—,
  h) N$_3$,
  i) R$^9$S(O)$_q$—,
  j) —HC=CH$_2$,
  k) —C≡CH,
  l) CF$_3$,
  m) R$^8$O(C=O)—, and
  n) R$^8$(O=C)O—;
R$^8$ is independently selected from
  hydrogen, unsubstituted or substituted C$_1$–C$_6$ alkyl, cycloalkyl, benzyl, and unsubstituted or substituted aryl;
R$^9$ is independently selected from:
  H, unsubstituted or substituted C$_1$–C$_6$ alkyl, benzyl, and unsubstituted or substituted aryl;
R$^{13}$ is independently selected from
  H, unsubstituted or substituted C$_1$–C$_6$ alkyl, unsubstituted or substituted aryl, unsubstituted or substituted morpholinyl, —(C$_1$–C$_6$ alkyl)OR$^8$, —(C$_1$–C$_6$ alkyl)OC(O)(C$_1$–C$_6$ alkyl), —(C$_1$–C$_6$ alkyl)N(R$^8$)$_2$, and —(C$_1$–C$_6$ alkyl)NHC(O)(C$_1$–C$_6$ alkyl)R$^8$;
A$^1$, A$^2$ and A$^3$ are independently selected from:
  a) a bond,
  b) —HC=CH—,
  c) —C≡C—,
  d) —O—,
  e) —(C=O)—,
  f) —O(C=O)—,
  g) —(C=O)O—,
  h) —NR$^8$—,
  i) —C(O)N(R$^8$)—,
  j) —N(R$^8$)C(O)—,
  k) —NHC(O)NH—,
  l) —S(O)$_q$—,
  m) —S(O)$_q$NH—, and
  n) —NHS(O)$_q$—;
A$^4$ is selected from:
  a) a bond,
  b) C(O),
  c) C=CH$_2$, and
  d) spiro C$_3$–C$_6$ cycloalkyl;
W is imidazolyl;
X is selected from:
  a) aryl,
  b) cycloalkyl,
  c) morpholinyl, and
  d) a bond;
Y is selected from:
  a) aryl, unsubstituted or substituted
  b) morpholinyl, unsubstituted or substituted, and
  c) cycloalkyl;
m is 0, 1, 2, 3 or 4;
n is 0, 1, 2, 3 or 4;
p is 0, 1, 2, 3 or 4;
q is 0, 1 or 2;
r is 0, 1, 2 or 3;
s is 0, 1, 2, 3 or 4; and
t is 0, 1, 2 or 3;
provided that $$-\!\!\!\{\!\!-A^1(C(R^{1a})_2)_nA^2(C(R^{1a})_2)_n\overset{(R^6)_t}{\overset{|}{-X}}\!\!-(C(R^{1b})_2)_pA^3(C(R^{1b})_2)_p\!\!-\!\!\}\!\!-$$

is not a bond;
or a pharmaceutically acceptable salt thereof.

2. The compound of claim 1, illustrated by formula A:

$$\text{A}$$

(structure with (R$^{13}$)$_s$, W, A$^4$, (C(R$^{1c}$)$_2$)$_m$, (R$^3$)$_r$, R$^2$, —A$^1$(C(R$^{1a}$)$_2$)$_n$A$^2$(C(R$^{1a}$)$_2$)$_n$—X—(C(R$^{1b}$)$_2$)$_p$A$^3$(C(R$^{1b}$)$_2$)$_p$—Y, R$^4$, R$^5$, (R$^6$)$_t$)

wherein:
  R$^{1a}$, R$^{1b}$ and R$^{1c}$ are independently selected from:
    a) hydrogen,
    b) unsubstituted or substituted aryl, unsubstituted or substituted morpholinyl, C$_3$–C$_{10}$ cycloalkyl, C$_2$–C$_6$ alkenyl, C$_2$–C$_6$ alkynyl, R$^8$O—, R$^9$S(O)$_q$—, CN, NO$_2$, R$^8$C(O)—, R$^8$OC(O)—, R$^8$(C$_1$–C$_6$ alkyl)O—, N$_3$, or N(R$^8$)$_2$;
    c) C$_1$–C$_6$ alkyl, unsubstituted or substituted by aryl, morpholinyl, C$_3$–C$_{10}$ cycloalkyl, C$_2$–C$_6$ alkenyl, C$_2$–C$_6$ alkynyl, R$^8$O—, R$^9$S(O)$_q$—, CN, R$^8$C(O)—, R$^8$OC(O)—, N$_3$, or R$^8$C(O)O—;
  R$^2$ is CN;
  R$^3$, R$^4$ and R$^5$ are independently selected from:
    H, CN, NO$_2$, halogen, unsubstituted or substituted C$_1$–C$_6$ alkyl, N$_3$, R$^9$S(O)$_q$, —C≡CH, unsubstituted or substituted aryl, unsubstituted or substituted morpholinyl, CF$_3$, CF$_3$O—, CF$_3$CH$_2$O—, C$_3$–C$_{10}$ cycloalkyl, OR$^8$, N(R$^8$)$_2$, —C(O)R$^8$, —O(C$_1$–C$_6$ alkyl)OR$^8$, —NHC(O)R$^8$, aralkyl, —(C$_1$–C$_6$ alkyl)OR$^8$, —(C$_1$–C$_6$ alkyl)C(O)R$^8$, —CH=CH—R$^8$ and $$-\underset{OH}{\overset{|}{C}}=\overset{H}{\overset{|}{C}}-R^8;$$

R$^6$ is independently selected from:
  a) hydrogen,
  b) CN,
  c) NO$_2$,
  d) halogen,
  e) aryl, unsubstituted or substituted,
  f) C$_1$–C$_6$ alkyl, unsubstituted or substituted,
  g) R$^8$O—, unsubstituted or substituted,
  h) N$_3$,
  i) R$^9$S(O)$_q$—,
  j) —HC=CH$_2$, k) —C≡CH,
l) $CF_3$
m) $R^8O(C=O)$—, and
n) $R^8 (O=C)O$—;

$R^8$ is independently selected from
hydrogen, unsubstituted or substituted $C_1$–$C_6$ alkyl, cycloalkyl, benzyl and unsubstituted or substituted aryl;

$R^9$ is independently selected from
H, unsubstituted or substituted $C_1$–$C_6$ alkyl, benzyl and unsubstituted or substituted aryl;

$R^{13}$ is independently selected from
H, unsubstituted or substituted $C_1$–$C_6$ alkyl, unsubstituted or substituted aryl, unsubstituted or substituted morpholinyl, —($C_1$–$C_6$ alkyl)$OR^8$, —($C_1$–$C_6$ alkyl)OC(O)($C_1$–$C_6$ alkyl), —($C_1$–$C_6$ alkyl)$N(R^8)_2$, and —($C_1$–$C_6$ alkyl)NHC(O)($C_1$–$C_6$ alkyl)$R^8$;

$A^1$, $A^2$ and $A^3$ are independently selected from:
a) a bond,
b) —HC=CH—,
c) —C≡C—,
d) —O—,
e) —(C=O)—,
f) —O(C=O)—,
g) —(C=O)O—,
h) —$NR^8$—,
i) —C(O)N($R^8$)—,
j) —N($R^8$)C(O)—,
k) —NHC(O)NH—,
l) —S(O)$_q$—,
m) —S(O)$_q$NH—, and
n) —NHS(O)$_q$—;

$A^4$ is selected from a bond, C(O), C=$CH_2$, or spiro $C_3$–$C_6$ cycloalkyl;

W is imidazolyl;

X is selected from:
a) aryl,
b) cycloalkyl,
c) morpholinyl, and
d) a bond;

Y is selected from:
a) aryl,
b) morpholinyl, and
c) cycloalkyl;

m is 0, 1, 2, 3 or 4;
n is 0, 1, 2, 3 or 4;
p is 0, 1, 2, 3 or 4;
q is 0, 1 or 2;
r is 1 or 2;

s is 0, 1, 2, 3 or 4; and
t is 0, 1, 2 or 3;
provided that

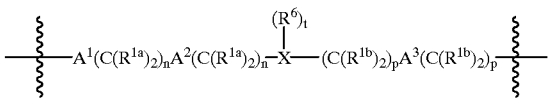

is not a bond;

or a pharmaceutically acceptable salt thereof.

3. The compound of claim 1, illustrated by formula B:

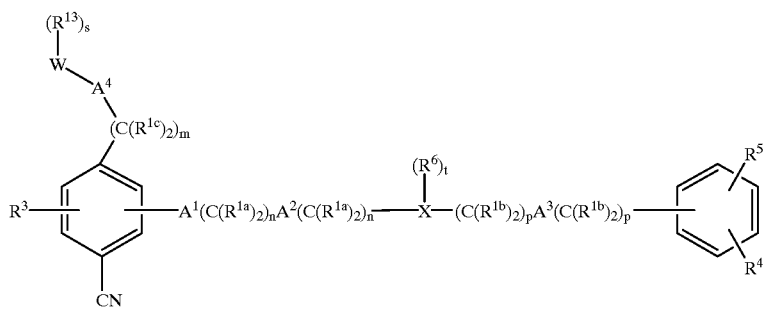

B wherein:

$R^{1a}$, $R^{1b}$ and $R^{1c}$ are independently selected from:
a) hydrogen,
b) unsubstituted or substituted aryl, unsubstituted or substituted morpholinyl, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $R^8(C_1$–$C_6$ alkyl)O— or $N_3$, $N(R^8)_2$;
c) $C_1$–$C_6$ alkyl, unsubstituted or substituted by aryl, morpholinyl, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N_3$, or $R^8C(O)O$—;

$R^3$, $R^4$ and $R^5$ are independently selected from:
H, CN, $NO_2$, halogen, unsubstituted or substituted $C_1$–$C_6$ alkyl, $N_3$, $R^9S(O)_q$, HC≡C—, unsubstituted or substituted aryl, unsubstituted or substituted morpholinyl, $CF_3$, $CF_3O$—, $CF_3CH_2O$—, $C_3$–$C_{10}$ cycloalkyl, $OR^8$, $N(R^8)_2$, —C(O)$R^8$, —O($C_1$–$C_6$ alkyl)$OR^8$, —NHC(O)$R^8$, aralkyl, —($C_1$–$C_6$ alkyl)$OR^8$, —($C_1$–$C_6$ alkyl)C(O)$R^8$, —CH=CH—$R^8$ and

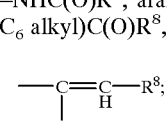

$R^6$ is independently selected from:
a) hydrogen,
b) CN,
c) $NO_2$,
d) halogen,
e) aryl, unsubstituted or substituted,
f) $C_1$–$C_6$ alkyl, unsubstituted or substituted,
g) $R^8O$—,
h) $N_3$,
i) $R^9S(O)_q$—, j) —HC=CH$_2$,
k) —C≡CH,
l) CF$_3$
m) R$^8$O(C=O)—, and
n) R$^8$(O=C)O—;

R$^8$ is independently selected from
  hydrogen, unsubstituted or substituted C$_1$–C$_6$ alkyl, cycloalkyl, benzyl and unsubstituted or substituted aryl;

R$^9$ is independently selected from
  H, unsubstituted or substituted C$_1$–C$_6$ alkyl, benzyl and unsubstituted or substituted aryl;

provided that $$-\!\!-\!\!A^1(C(R^{1a})_2)_nA^2(C(R^{1a})_2)_n\!\!-\!\!\overset{(R^6)_t}{X}\!\!-\!\!(C(R^{1b})_2)_pA^3(C(R^{1b})_2)_p\!\!-\!\!-$$

is not a bond;
or a pharmaceutically acceptable salt thereof.

4. The compound of claim 3, illustrated by formula B:

B

[Chemical structure showing a central phenyl ring with CN substituent, R$^3$ group, connected via A$^1$(C(R$^{1a}$)$_2$)$_n$A$^2$(C(R$^{1a}$)$_2$)$_n$—X(R$^6$)$_t$—(C(R$^{1b}$)$_2$)$_p$A$^3$(C(R$^{1b}$)$_2$)$_p$— to another phenyl ring with R$^4$ and R$^5$ substituents; and bearing a (C(R$^{1c}$)$_2$)$_m$—A$^4$—W(R$^{13}$)$_s$ substituent]

R$^{13}$ is independently selected from
  H, unsubstituted or substituted C$_1$–C$_6$ alkyl, unsubstituted or substituted aryl, unsubstituted or substituted morpholinyl, —(C$_1$–C$_6$ alkyl)OR$^8$, —(C$_1$–C$_6$ alkyl)OC(O)(C$_1$–C$_6$ alkyl), —(C$_{C6}$ alkyl)N(R$^8$)$_2$, and —(C$_1$–C$_6$ alkyl)NHC(O)(C$_1$–C$_6$ alkyl)R$^8$;

A$^1$, A$^2$ and A$^3$ are independently selected from:
  a) a bond,
  b) —HC=CH—,
  c) —C≡C—,
  d) —O—,
  e) —(C=O)—,
  f) —O(C=O)—,
  g) —(C=O)O—,
  h) —NR$^8$—,
  i) —C(O)N(R$^8$)—,
  j) —N(R$^8$)C(O)—,
  k) —NHC(O)NH—,
  l) —S(O)$_q$—,
  m) —S(O)$_q$NH—, and
  n) —NHS(O)$_q$—;

A$^4$ is selected from a bond, C(O), C=CH$_2$, or spiro C$_3$–C$_6$ cycloalkyl;

W is imidazolyl;

X is selected from:
  a) aryl,
  b) cycloalkyl,
  c) morpholinyl, and
  d) a bond;

m is 0, 1, 2, 3 or 4;
n is 0, 1, 2, 3 or 4;
p is 0, 1, 2, 3 or 4;
q is 0 or 2;
s is 0, 1, 2, 3 or 4; and
t is 0, 1, 2 or 3;

wherein:
R$^{1a}$, R$^{1b}$ and R$^{1c}$ are independently selected from:
  a) hydrogen,
  b) unsubstituted or substituted aryl, unsubstituted or substituted morpholinyl, C$_3$–C$_{10}$ cycloalkyl, C$_2$–C$_6$ alkenyl, C$_2$–C$_6$ alkynyl, R$^8$O—, R$^9$S(O)$_q$—, CN, NO$_2$, R$^8$C(O)—, R$^8$OC(O)—, R$^8$(C$_1$–C$_6$ alkyl)O—, N$_3$, or N(R$^8$)$_2$;
  c) C$_1$–C$_6$ alkyl, unsubstituted or substituted by aryl, Morpholinyl, C$_3$–C$_{10}$ cycloalkyl, C$_2$–C$_6$ alkenyl, C$_2$–C$_6$ alkynyl, R$^8$O—, R$^9$S(O)$_q$—, CN, R$^8$C(O)—, R$^8$OC(O)—, N$_3$, or R$^8$C(O)O—;

R$^3$, R$^4$ and R$^5$ are independently selected from:
  H, CN, NO$_2$, halogen, unsubstituted or substituted C$_1$–C$_6$ alkyl, N$_3$, R$^9$S(O)$_q$, HC≡C—, unsubstituted or substituted aryl, unsubstituted or substituted morpholinyl, CF$_3$, CF$_3$O—, CF$_3$CH$_2$O—, C$_3$–C$_{10}$ cycloalkyl, OR$^8$, N(R$^8$)$_2$, —C(O)R$^8$, —O(C$_1$–C$_6$ alkyl)OR$^8$, —NHC(O)R$^8$, aralkyl, —(C$_1$–C$_6$ alkyl)OR$^8$, —(C$_1$–C$_6$ alkyl)C(O)R$^8$, —CH=CH—R$^8$ and $$-\!\!\underset{\underset{OH}{|}}{C}\!\!=\!\!\overset{H}{\underset{}{C}}\!\!-\!\!R^8;$$

R$^6$ is independently selected from:
  a) hydrogen,
  b) CN,
  c) NO$_2$,
  d) halogen,
  e) aryl, unsubstituted or substituted,
  f) C$_1$–C$_6$ alkyl, unsubstituted or substituted,
  g) R$^8$O—,
  h) N$_3$,
  i) R$^9$S(O)$_q$,
  j) —HC=CH$_2$,
  k) —C≡CH,
  l) CF$_3$, m) R⁸O(C=O)—, and
n) R⁸ (O=C)O—;
R⁸ is independently selected from
  hydrogen, unsubstituted or substituted $C_1$–$C_6$ alkyl, cycloalkyl, benzyl and unsubstituted or substituted aryl;
R⁹ is independently selected from
  H, unsubstituted or substituted $C_1$–$C_6$ alkyl, benzyl and unsubstituted or substituted aryl;
R¹³ is independently selected from
  H, unsubstituted or substituted $C_1$–$C_6$ alkyl, unsubstituted or substituted aryl, unsubstituted or substituted morpholinyl, —($C_1$–$C_6$ alkyl)OR⁸, —($C_1$–$C_6$ alkyl)OC(O)($C_1$–$C_6$ alkyl), —($C_1$–$C_6$ alkyl)N(R⁸)₂, and —($C_1$–$C_6$ alkyl)NHC(O)($C_1$–$C_6$ alkyl)R⁸;
A¹ is selected from:

a) a bond,
b) —O—,
c) —(C=O)—,
d) —NR⁸—,
e) —C(O)N(R⁸)—, and
f) —S(O)$_q$—;
A² and A³ are independently selected from:
a) a bond,
b) —HC=CH—,
c) —C≡C—,
d) —O—,
e) —(C=O)—,
f) —O(C=O)—,
g) —(C=O)O—,
h) —NR⁸—,
i) —C(O)N(R⁸)—,
j) —N(R⁸)C(O)—,
k) —NHC(O)NH—,
l) —S(O)$_q$—,
m) —S(O)$_q$NH—, and
n) —NHS(O)$_q$—;
A⁴ is selected from a bond, C(O), C=CH₂, or spiro $C_3$–$C_6$ cycloalkyl;
W is imidazolyl;
X is selected from:
a) aryl,
b) morpholinyl, and
c) a bond;
m is 0, 1, 2, 3 or 4;
n is 0, 1, 2, 3 or 4;
p is 0, 1, 2, 3 or 4;
q is 0, 1 or 2;

s is 0, 1, 2, 3 or 4; and
t is 0, 1, 2 or 3;

provided that

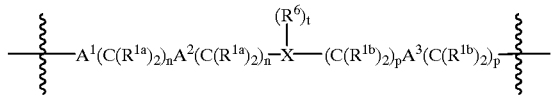

is not a bond;

or a pharmaceutically acceptable salt thereof.

5. The compound of claim 1, illustrated by formula C:

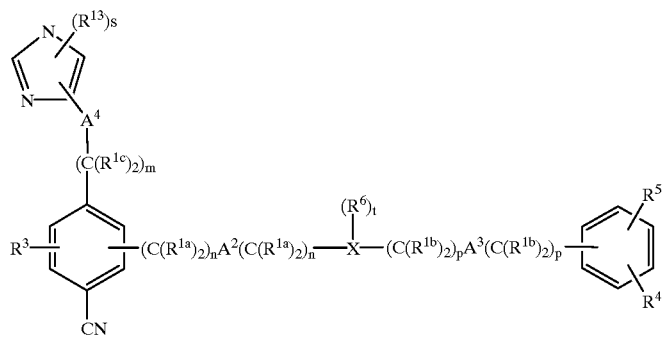

wherein:
R¹ᵃ, R¹ᵇ and R¹ᶜ are independently selected from:
  a) hydrogen,
  b) unsubstituted or substituted aryl, unsubstituted or substituted morpholinyl, $C_3$–$C_{10}$ cycloalkyl, $C_2$–$C_6$ alkenyl, $C_2$–$C_6$ alkynyl, R⁸O—, R⁹S(O)$_q$—, CN, NO₂, R⁸C(O)—, R⁸OC(O)—, R⁸($C_1$–$C_6$ alkyl)O—, N₃ or N(R⁸)₂;
  c) $C_1$–$C_6$ alkyl, unsubstituted or substituted by aryl, morpholinyl, $C_3$–$C_{10}$ cycloalkyl, $C_2$–$C_6$ alkenyl, $C_2$–$C_6$ alkynyl, R⁸O—, R⁹S(O)$_q$—, CN, R⁸C(O)—, R⁸OC(O)—, N₃, or R⁸C(O)O—;
R³, R⁴ and R⁵ are independently selected from:
  H, CN, NO₂, halogen, unsubstituted or substituted $C_1$–$C_6$ alkyl, N₃, R⁹S(O)$_q$, HC≡C—, unsubstituted or substituted aryl, unsubstituted or substituted morpholinyl, CF₃, CF₃O—, CF₃CH₂O—, $C_3$–$C_{10}$ cycloalkyl, OR⁸, N(R⁸)₂, —C(O)R⁸, —O($C_1$–$C_6$ alkyl)OR⁸, —NHC(O)R⁸, aralkyl, —($C_1$–$C_6$ alkyl)OR⁸, —($C_1$–$C_6$ alkyl)C(O)R⁸, —CH=CH—R⁸ and

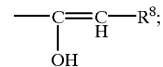

R⁶ is independently selected from:
  a) hydrogen,
  b) CN,
  c) NO₂,
  d) halogen,
  e) aryl, unsubstituted or substituted,
  f) $C_1$–$C_6$ alkyl, unsubstituted or substituted,
  g) R⁸O—, h) $N_3$,
i) $R^9S(O)_q$—,
j) $CF_3$,
k) $R^8O(C=O)$—, and
l) $R^8(O=C)O$—;

$R^8$ is independently selected from
hydrogen, unsubstituted or substituted $C_1$–$C_6$ alkyl, cycloalkyl, benzyl and unsubstituted or substituted aryl;

$R^9$ is independently selected from
H, unsubstituted or substituted $C_1$–$C_6$ alkyl, benzyl and unsubstituted or substituted aryl;

$R^{13}$ is independently selected from
H, unsubstituted or substituted $C_1$–$C_6$ alkyl, unsubstituted or substituted aryl, unsubstituted or substituted morpholinyl, —($C_1$–$C_6$ alkyl)$OR^8$, —($C_1$–$C_6$ alkyl)OC(O)($C_1$–$C_6$ alkyl), —($C_1$–$C_6$ alkyl)N($R^8$)$_2$, and —($C_1$–$C_6$ alkyl)NHC(O)($C_1$–$C_6$ alkyl)$R^8$;

$A^2$ is selected from:
a) a bond,
b) —HC=CH—,
c) —C≡C—,
d) —O—,
e) —(C=O)—,
f) —O(C=O)—,
g) —(C=O)O—,
h) —$NR^8$—,
i) —C(O)N($R^8$)—,
j) —N($R^8$)C(O)—,
k) —NHC(O)NH—,
l) —S(O)$_q$—,
m) —S(O)$_q$NH—, and
n) —NHS(O)$_q$—;

$A^3$ is selected from:
a) a bond,
b) —O—,
c) —S(O)$_q$—,
d) —S(O)$_q$NH—,
e) —$NR^8$—,
f) —(C=O)—,
g) —(C=O)O—,
h) —O(C=O)—,
i) —C(O)N($R^8$)—,
j) —N($R^8$)C(O)—, and
k) —NHC(O)NH—;

$A^4$ is selected from a bond, C(O), C=$CH_2$, or spiro $C_3$–$C_6$ cycloalkyl;

X is selected from:
a) aryl,
b) morpholinyl, and
c) a bond;

m is 0, 1, 2, 3 or 4;
n is 0, 1, 2, 3 or 4;
p is 0, 1, 2, 3 or 4;
q is 0, 1 or 2;
s is 0, 1, 2, 3 or 4; and
t is 0, 1, 2 or 3;

provided that

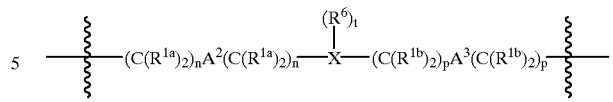

is not a bond;
or a pharmaceutically acceptable salt thereof.

6. The compound of claim 1, illustrated by formula E:

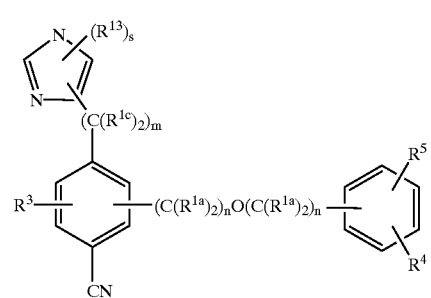

wherein:
$R^{1a}$ and $R^{1c}$ are independently selected from:
a) hydrogen,
b) unsubstituted or substituted aryl, unsubstituted or substituted morpholinyl, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $R^8(C_1$–$C_6$ alkyl)O—, $N_3$, or $N(R^8)_2$;
c) $C_1$–$C_6$ alkyl, unsubstituted or substituted by aryl, morpholinyl, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N_3$, or $R^8C(O)O$—;

$R^3$, $R^4$ and $R^5$ are independently selected from:
H, CN, $NO_2$, halogen, unsubstituted or substituted $C_1$–$C_6$ alkyl, $N_3$, $R^9S(O)_q$, HC≡C—, unsubstituted or substituted aryl, unsubstituted or substituted morpholinyl, $CF_3$, $CF_3O$—, $CF_3CH_2O$—, $C_3$–$C_{10}$ cycloalkyl, $OR^8$, $N(R^8)_2$, —C(O)$R^8$, —O($C_1$–$C_6$ alkyl)$OR^8$, —NHC(O)$R^8$, aralkyl, —($C_1$–$C_6$ alkyl)$OR^8$, —($C_1$–$C_6$ alkyl)C(O)$R^8$, —CH=CH—$R^8$ and

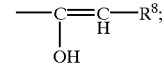

$R^8$ is independently selected from
hydrogen, unsubstituted or substituted $C_1$–$C_6$ alkyl, cycloalkyl, benzyl and unsubstituted or substituted aryl;

$R^9$ is independently selected from
H, unsubstituted or substituted $C_1$–$C_6$ alkyl, benzyl and unsubstituted or substituted aryl;

$R^{13}$ is independently selected from
H, unsubstituted or substituted $C_1$–$C_6$ alkyl, unsubstituted or substituted aryl, unsubstituted or substituted morpholinyl, —($C_1$–$C_6$ alkyl)$OR^8$, —($C_1$–$C_6$ alkyl)OC(O)($C_1$–$C_6$ alkyl), —($C_1$–$C_6$ alkyl)N($R^8$)$_2$, and —($C_1$–$C_6$ alkyl)NHC(O)($C_1$–$C_6$ alkyl)$R^8$;

m is 0, 1, 2, 3 or 4;
n is 0, 1, 2, 3 or 4;
q is 0, 1 or 2; and s is 0, 1, 2, 3 or 4;
or a pharnaceutically acceptable salt thereof.

7. A compound of formula I:

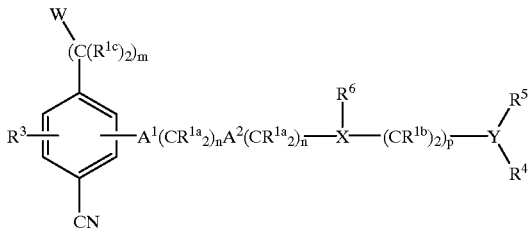

I wherein:

$R^{1a}$, $R^{1b}$ and $R^{1c}$ are independently selected from:
a) hydrogen,
b) unsubstituted or substituted aryl; unsubstituted or substituted morpholinyl, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, or $N_3$;
c) $C_1$–$C_6$ alkyl, unsubstituted or substituted by aryl, morpholinyl, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N_3$, or $R^8C(O)O$—;

$R^3$, $R^4$ and $R^5$ are independently selected from:
a) H,
b) CN,
c) $NO_2$,
d) halogen,
e) $C_1$–$C_6$ alkyl,
f) $C_1$–$C_6$ alkoxy,
g) $N_3$,
h) $R^9S(O)_q$,
i) —HC=$CH_2$,
j) —C≡CH,
k) aryl, unsubstituted or substituted,
l) morpholinyl, unsubstituted or substituted,
m) $CF_3O$—,
n) $CF_3CH_2O$—,
o) $C_3$–$C_{10}$ cycloalkyl, and
p) $CF_3$;

$R^6$ is independently selected from:
a) hydrogen,
b) CN,
c) $NO_2$,
d) halogen,
e) aryl, unsubstituted or substituted,
f) $C_1$–$C_6$ alkyl, unsubstituted or substituted,
g) $R^8O$,
h) $N_3$,
i) $R^9S(O)_q$,
j) —HC=$CH_2$,
k) —C≡CH,
l) $CF_3$
m) $R^8O(C=O)$, and
n) $R^8$ (O=C)O;

$R^8$ is independently selected from hydrogen, $C_1$–$C_6$ alkyl, benzyl and aryl;

$R^9$ is independently selected from $C_1$–$C_6$ alkyl, benzyl and aryl;

$A^1$ and $A^2$ are independently selected from:
a) a bond,
b) —HC=CH—,
c) —C≡C—,
d) O,
e) $S(O)_q$,
f) $O(C=O)$,
g) (O=C), and
h) (C=O)O;

W is imidazolyl;

X is selected from:
a) aryl,
b) cycloalkyl,
c) morpholinyl, and
d) a bond;

Y is selected from:
a) aryl, unsubstituted or substituted, and
b) morpholinyl, unsubstituted or substituted;

m is 0, 1, 2, 3 or 4;
n is 0, 1, 2, 3 or 4;
p is 0, 1, 2, 3 or 4; and
q is 0, 1 or 2;
provided that

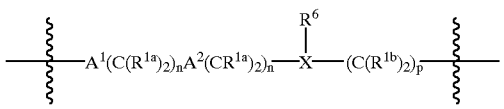

is not a bond;
or a pharmaceutically acceptable salt thereof.

8. The compound of claim 7, illustrated by formula Ia:

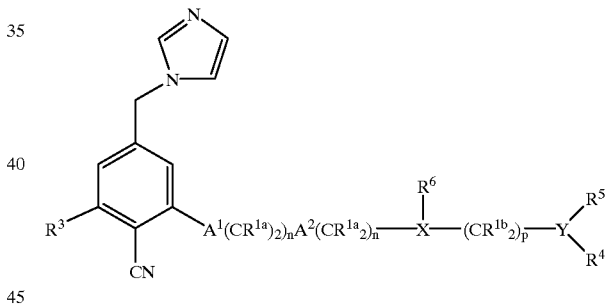

Ia wherein:

$R^{1a}$ is selected from: hydrogen or $C_1$–$C_6$ alkyl;

$R^{1b}$ is independently selected from:
a) hydrogen,
b) aryl, morpholinyl, $C_3$–$C_{10}$ cycloalkyl, $R^8O$— or $C_2$–$C_6$ alkenyl,
c) $C_1$–$C_6$ alkyl unsubstituted or substituted by aryl, morpholinyl, cycloalkyl, alkenyl, or $R^8O$—;

$R^3$ and $R^4$ are independently selected from hydrogen, F, Cl, Br, $N_3$, CN, $C_1$–$C_6$ alkyl, substituted or unsubstituted aryl and substituted or unsubstituted morpholinyl;

$R^5$ is selected from:
a) hydrogen, and
b) $C_1$–$C_6$ alkyl substituted with hydrogen or a group selected from unsubstituted or substituted aryl, unsubstituted or substituted morpholinyl, unsubstituted or substituted $C_3$–$C_{10}$ cycloalkyl, $CF_3$, $NO_2$, $R^8O$—, $R^9S(O)_q$—, $R^8C(O)$—, $R^8OC(O)$—, $N_3$, and CN;

$R^6$ is independently selected from:
a) hydrogen, b) $C_1$–$C_6$ alkyl, $C_1$–$C_6$ perfluoroalkyl, F, Cl, CN, $NO_2$, and c) $C_1$–$C_6$ alkyl substituted by $C_1$–$C_6$ perfluoroalkyl, $R^8O$—, $R^8C(O)$—, or $R^8OC(O)$—;

$R^8$ is independently selected from hydrogen, $C_1$–$C_6$ alkyl, benzyl and aryl;

$R^9$ is independently selected from $C_1$–$C_6$ alkyl, benzyl and aryl;

$A^1$ and $A^2$ are independently selected from: a bond, —HC=CH—, —C≡C—, O, $S(O)_q$, $O(C=O)$, and $(O=C)O$;

X is selected from:
a) aryl,
b) cycloalkyl,
c) morpholinyl, and
d) a bond;

Y is selected from:
a) aryl, unsubstituted or substituted, and
b) morpholinyl, unsubstituted or substituted;

n is 0, 1, 2, 3 or 4;

p is 0, 1, 2, 3 or 4; and q is 0, 1 or 2;

provided that

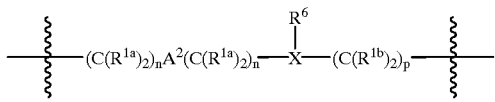

is not a bond;

or a pharmaceutically acceptable salt thereof.

9. The compound of claim 7, illustrated by formula Ib:

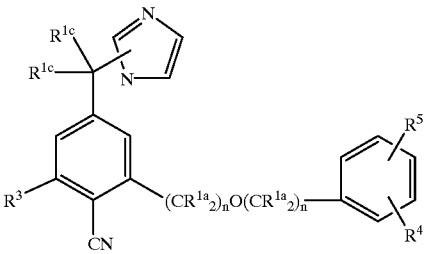

wherein:

$R^{1a}$ is selected from:
a) hydrogen,
b) unsubstituted or substituted aryl; unsubstituted or substituted morpholinyl; $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, or $N_3$;
c) $C_1$–$C_6$ alkyl, unsubstituted or substituted by aryl, morpholinyl, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N_3$, or —$R^8C(O)O$—;

$R^{1c}$ is independently selected from: H, unsubstituted or substituted $C_1$–$C_6$ alkyl, and unsubstituted or substituted aryl;

$R^3$ is selected from hydrogen, F, Cl, Br, $N_3$, CN, $C_1$–$C_6$ alkyl, substituted or unsubstituted aryl and substituted or unsubstituted morpholinyl;

$R^4$ and $R^5$ are independently selected from:
a) H,
b) halogen,
c) aryl, unsubstituted or substituted, and
d) $C_1$–$C_6$ alkyl;

$R^8$ is independently selected from hydrogen, $C_1$–$C_6$ alkyl, benzyl and aryl;

$R^9$ is independently selected from $C_1$–$C_6$ alkyl, benzyl and aryl;

n is independently selected from: 0, 1, 2, 3 or 4; and q is 0, 1 or 2;

or a pharmaceutically acceptable salt thereof.

10. A compound which inhibits a prenyl-protein transferase, selected from the group consisting of:

3-(biphenyl-4-ylmethoxy)-4-imidazol-1-ylmethyl-benzonitrile;

3-(biphenyl-4-yl-2-ethoxy)-4-imidazol-1-ylmethylbenzonitrile;

3-(biphenyl-3-ylmethoxy)-4-imidazol-1-ylmethyl-benzonitrile;

2-(biphenyl-4-ylmethoxy)-4-imidazol-1-ylmethyl-benzonitrile;

2-(biphenyl-4-yl-2-ethoxy)-4-imidazol-1-ylmethyl-benzonitrile;

2-(3-chlorophenoxy)-4-imidazol-1-ylmethyl-benzonitrile;

2-(4-chlorophenyl-2-ethoxy)-4-imidazol-1-ylmethyl-benzonitrile;

2-(3-chlorophenyl-2-ethoxy)-4-imidazol-1-ylmethyl-benzonitrile;

2-(2-chlorophenyl-2-ethoxy)-4-imidazol-1-ylmethyl-benzonitrile;

2-(phenyl-2-ethoxy)-4-imidazol-1-ylmethyl-benzonitrile;

2-(3-chlorobenzyloxy)-4-imidazol-1-ylmethyl-benzonitrile;

2-(4-chlorobenzyloxy)-4-imidazol-1-ylmethyl-benzonitrile;

2-(2,4-dichlorobenzyloxy)-4-imidazol-1-ylmethyl-benzonitrile;

2-(benzyloxy)-4-imidazol-1-ylmethyl-benzonitrile;

2-(biphenyl-2-ylmethoxy)-4-imidazol-1-ylmethyl-benzonitrile;

2-(phenyl-4-butoxy)-4-imidazol-1-ylmethyl-benzonitrile;

2-(phenyl-3-propoxy)-4-imidazol-1-ylmethyl-benzonitrile;

2-(biphenyl-4-yl-2-ethoxy)-4-(2-methyl-imidazol-1-yl)methyl-benzonitrile;

2-(biphenyl-4-yl-2-ethoxy)-4-benzimidazol-1-yl)methyl-benzonitrile;

4-imidazol-1-ylmethyl-2-(naphthalen-2-yloxy)-benzonitrile;

2-(3-cyanophenoxy)-4-imidazol-1-ylmethyl-benzonitrile;

2-(3-bromophenoxy)-4-imidazol-1-ylmethyl-benzonitrile;

2-(biphen-3-yloxy)-4-imidazol-1-ylmethyl-benzonitrile;

2-(biphen-4-yloxy)-4-imidazol-1-ylmethyl-benzonitrile;

2-(3-acetylphenoxy)-4-imidazol-1-ylmethyl-benzonitrile;

2-(2-acetylphenoxy)-4-imidazol-1-ylmethyl-benzonitrile;

2-(3-trifluoromethylphenoxy)-4-imidazol-1-ylmethyl-benzonitrile;

2-(3-methylphenoxy)-4-imidazol-1-ylmethyl-benzonitrile;

2-(2-methylphenoxy)-4-imidazol-1-ylmethyl-benzonitrile;

2-(4-methylphenoxy)-4-imidazol-1-ylmethyl-benzonitrile;
2-(3-methoxyphenoxy)-4-imidazol-1-ylmethyl-benzonitrile;
2-(2-methoxyphenoxy)-4-imidazol-1-ylmethyl-benzonitrile;
2-(4-methoxyphenoxy)-4-imidazol-1-ylmethyl-benzonitrile;
2-(3,5-dimethylphenoxy)-4-imidazol-1-ylmethyl-benzonitrile;
2-(3,4-dimethylphenoxy)-4-imidazol-1-ylmethyl-benzonitrile;
2-(3,5-dimethoxyphenoxy)-4-imidazol-1-ylmethyl-benzonitrile;
2-(1-naphthyloxy)-4-imidazol-1-ylmethyl-benzonitrile;
2-(2,4-dichlorophenoxy)-4-imidazol-1-ylmethyl-benzonitrile;
2-(3-fluorophenoxy)-4-imidazol-1-ylmethyl-benzonitrile;
2-(3-t-butylphenoxy)-4-imidazol-1-ylmethyl-benzonitrile;
2-[3-(N,N-diethylamino)phenoxy]-4-imidazol-1-ylmethyl-benzonitrile;
2-(3-n-propylphenoxy)-4-imidazol-1-ylmethyl-benzonitrile;
2-(2,3-dimethoxyphenoxy)-4-imidazol-1-ylmethyl-benzonitrile;
2-(2,3-dimethylphenoxy)-4-imidazol-1-ylmethyl-benzonitrile;
2-(3,4-dimethoxyphenoxy)-4-imidazol-1-ylmethyl-benzonitrile;
2-(2,5-dimethoxyphenoxy)-4-imidazol-1-ylmethyl-benzonitrile;
2-(3,4-dichlorophenoxy)-4-imidazol-1-ylmethyl-benzonitrile;
2-(2,4-dimethylphenoxy)-4-imidazol-1-ylmethyl-benzonitrile;
2-(4-chloro-2-methylphenoxy)-4-imidazol-1-ylmethyl-benzonitrile;
2-(5-chloro-2-methylphenoxy)-4-imidazol-1-ylmethyl-benzonitrile;
2-(2-chloro-4,5-dimethylphenoxy)-4-imidazol-1-ylmethyl-benzonitrile;
2-(5-hydroxymethyl-2-methoxyphenoxy)-4-imidazol-1-ylmethyl-benzonitrile;
4-imidazol-1-ylmethyl-2-(3-phenylamino-phenoxy)-benzonitrile;
4-imidazol-1-ylmethyl-2-[3-(2-methylphenylamino)-phenoxy]-benzonitrile;
4-imidazol-1-ylmethyl-2-(3-phenoxy-phenoxy)-benzonitrile;
2-(2-benzoyl-phenoxy)-4-imidazol-1-ylmethyl-benzonitrile;
1-(5-chloro-2-methoxy-phenyl)-3-[3-(2-cyano-5-inidazol-1-ylmethyl-phenoxy)-phenyl]-urea;
1-(2,5-dimethoxy-phenyl)-3-[3-(2-cyano-5-imidazol-1-ylmethyl-phenoxy)-phenyl]-urea;
2-(3-benzyloxy-phenoxy)-4-imidazol-1-ylmethyl-benzonitrile;
2-(4-benzyloxy-phenoxy)-4-imidazol-1-ylmethyl-benzonitrile;
2-(2-benzyl-phenoxy)-4-imidazol-1-ylmethyl-benzonitrile;
2-(3-ethynyl-phenoxy)-4-imidazol-1-ylmethyl-benzonitrile;
2-(4-acetyl-3-methyl-phenoxy)-4-imidazol-1-ylmethyl-benzonitrile;
4-imidazol-1-ylmethyl-2-(5,6,7,8-tetrahydro-naphthalen-1-yloxy)-benzonitrile;
4-imidazol-1-ylmethyl-2-(8-oxo-5,6,7,8-tetrahydro-naphthalen-1-yloxy)-benzonitrile;
2-[3-(2-hydroxy-ethoxy)-phenoxy]-4-imidazol-1-ylmethyl-benzonitrile;
4'-(2-cyano-5-imidazol-1-ylmethyl-phenoxy)-biphenyl-4-carbonitrile;
N-[3-(2-cyano-5-imidazol-1-ylmethyl-phenoxy)-phenyl]-acetamide;
4-imidazol-1-ylmethyl-2-(9-oxo-9H-fluoren-4-yloxy)-benzonitrile;
3-(2-cyano-5-imidazol-1-ylmethyl-phenoxy)-N-phenyl-benzamide;
3-(2-cyano-5-imidazol-1-ylmethyl-phenoxy)-N-ethyl-N-phenyl-benzamide;
3-(2-cyano-5-imidazol-1-ylmethyl-phenoxy)-N-cyclopropylmethyl-N-phenyl-benzamide;
N-[3-(2-cyano-5-imidazol-1-ylmethyl-phenoxy)-phenyl]-benzenesulfonamide;
4-imidazol-1-ylmethyl-2-(5,6,7,8-tetrahydro-naphthalen-2-yloxy)-benzonitrile;
4-imidazol-1-ylmethyl-2-(2-methoxy-4-propenyl-phenoxy)-benzonitrile;
4-imidazol-1-ylmethyl-2-[4-(3-oxo-butyl)-phenoxy]-benzonitrile;
2-(3-chlorophenoxy)-5-imidazol-1-ylmethyl-benzonitrile;
2-(4-chlorophenoxy)-4-imidazol-1-ylmethyl-benzonitrile;
2-(3,5-dichlorophenoxy)-4-imidazol-1-ylmethyl-benzonitrile;
2-(2-chlorophenoxy)-4-imidazol-1-ylmethyl-benzonitrile;
2-(3-chlorophenoxy)-5-(4-phenyl-imidazol-1-ylmethyl)-benzonitrile;
2-(biphen-2-yloxy)-4-imidazol-1-ylmethyl-benzonitrile;
2-(phenoxy)-4-imidazol-1-ylmethyl-benzonitrile;
2-(2-chloro-4-methoxyphenoxy)-4-imidazol-1-ylmethyl-benzonitrile;
2-(2-chlorophenylsulfanyl)-4-imidazol-1-ylmethyl-benzonitrile;
4-imidazol-1-ylmethyl-2-(naphthalen-2-ylsulfanyl)-benzonitrile;
2-(2,4-dichlorophenylsulfanyl)-4-imidazol-1-ylmethyl-benzonitrile;
2-(2,4-dichloro-benzenesulfinyl)-4-imidazol-1-ylmethyl-benzonitrile;
2-(2,4-dichloro-benzenesulfonyl)-4-imidazol-1-ylmethyl-benzonitrile;
2-(4-chloro-2-methoxyphenoxy)-4-imidazol-1-ylmethyl-benzonitrile;
2-(2-chlorophenoxy)-4-(5-methyl-imidazol-1-ylmethyl)-benzonitrile;
2-(2-chlorophenoxy)-4-(4-methyl-imidazol-1-ylmethyl)-benzonitrile;
2-(2,4-dichlorophenoxy)-4-(2-methyl-imidazol-1-ylmethyl)-benzonitrile;

N-[3-(2-cyano-5-imidazol-1-ylmethyl-phenoxy)-phenyl]-benzamide;

2-[3-(2-cyano-5-imidazol-1-ylmethyl-phenoxy)-phenyl]-N-phenyl-acetamide;

N-[3-(2-cyano-5-imidazol-1-ylmethyl-phenoxy)-phenyl]-2-phenyl-acetamide;

2-(2,3-dimethoxyphenoxy)-4-(2,4-dimethyl-imidazol-1-ylmethyl)-benzonitrile;

4-(2-methyl-imidazol-1-ylmethyl)-2-(naphthalen-2-yloxy)-benzonitrile;

4-(1-imidazol-1-yl-1-methyl-ethyl)-2-(naphthalen-2-yloxy)-benzonitrile;

1-[4-iodo-3-(naphthalen-2-yloxy)-benzyl]-1H-imidazole;

acetic acid 3-[3-(2-chloro-phenoxy)-4-cyano-benzyl]-3H-imidazol-4-ylmethyl ester;

2-(2-chloro-phenoxy)-4-(5-hydroxymethyl-imidazol-1-ylmethyl)-benzonitrile;

4-(5-aminomethyl-imidazol-1-ylmethyl)-2-(2-chloro-phenoxy)-benzonitrile;

N-{3-[4-cyano-3-(2,3-dimethoxy-phenoxy)-benzyl]-3H-imidazol-4-ylmethyl}-2-cyclohexyl-acetamide;

2-(3-chloro-phenoxy)-4-[(4-chloro-phenyl)-imidazol-1-yl-methyl]-benzonitrile;

2-(3-chloro-phenoxy)-4-[1-(4-chloro-phenyl)-2-hydroxy-1-imidazol-1-yl-ethyl]-benzonitrile 2-(3-chloro-phenoxy)-4-[(4-chloro-phenyl)-hydroxy-(3H-imidazol-4-yl)-methyl]-benzonitrile;

2-(2,4-dichloro-phenylsulfanyl)-4-[5-(2-morpholin-4-yl-ethyl)-imidazol-1-ylmethyl]-benzonitrile;

2-(2,4-dichloro-phenoxy)-4-[5-(2-morpholin-4-yl-ethyl)-imidazol-1-ylmethyl]-benzonitrile;

4-[hydroxy-(3-methyl-3H-imidazol-4-yl)-methyl]-2-(naphthalen-2-yloxy)-benzonitrile;

4-[amino-(3-methyl-3H-imidazol-4-yl)-methyl]-2-(naphthalen-2-yloxy)-benzonitrile;

4-[1-hydroxy-1-(3-methyl-3H-imidazol-4-yl)-ethyl]-2-(naphthalen-2-yloxy)-benzonitrile;

4-[1-amino-1-(3-methyl-3H-imidazol-4-yl)-ethyl]-2-(naphthalen-2-yloxy)-benzonitrile hydrochloride;

3-{2-cyano-5-[1-amino-1-(3-methyl-3H-imidazol-4-yl)-ethyl]-phenoxy}-N-ethyl-N-phenyl-benzamide;

3-{2-cyano-5-[1-hydroxy-1-(3-methyl-3H-imidazol-4-yl)-ethyl]-phenoxy}-N-ethyl-N-phenyl-benzamide;

4-[1-hydroxy-1-(3-methyl-3H-imidazol-4-yl)-ethyl]-2-(3-phenylamino-phenoxy)-benzonitrile;

4-[1-hydroxy-1-(3-methyl-3H-imidazol-4-yl)-ethyl]-2-(3-phenoxy-phenoxy)-benzonitrile;

2-(3-benzoyl-phenoxy)-4-[1-hydroxy-1-(3-methyl-3H-imidazol-4-yl)-ethyl]-benzonitrile;

2-(3-tert-butyl-phenoxy)-4-[1-hydroxy-1-(3-methyl-3H-imidazol-4-yl)-ethyl]-benzonitrile;

2-(3-diethylamino-phenoxy)-4-[1-hydroxy-1-(3-methyl-3H-imidazol-4-yl)-ethyl]-benzonitrile;

or a pharnnaceutically acceptable salt thereof.

11. The compound according to claim 10 which is:

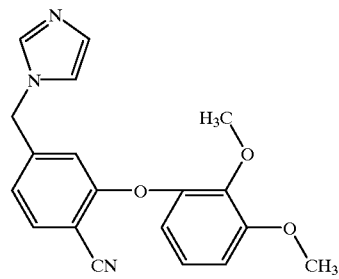

2-(2,3-Dimethoxyphenoxy)-4-imidazol-1-ylmethyl-benzonitrile;

or a pharmaceutically acceptable salt thereof.

12. The compound according to claim 10 which is:

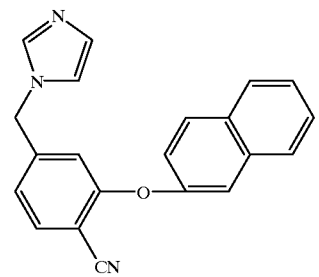

4-Imidazol-1-ylmethyl-2-(naphthalen-2-yloxy)-benzonitrile or a pharmaceutically acceptable salt thereof.

13. The compound according to claim 10 which is:

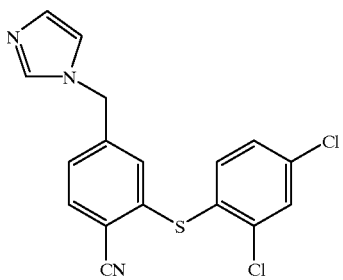

2-(2,4-Dichlorophenylsulfanyl)-4-imidazol-1-ylmethyl-benzonitrile or a pharmaceutically acceptable salt thereof.

14. The compound according to claim 10 which is:

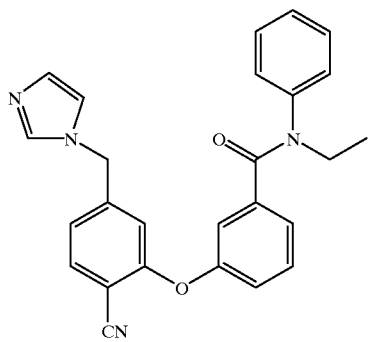

3-(2-Cyano-5-imidazol-1-ylmethyl-phenoxy)-N-ethyl-N-phenyl-benzamide
or a pharmaceutically acceptable salt thereof.

15. The compound according to claim 10 which is:

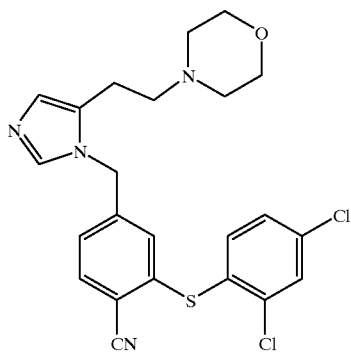

2-(2,4-dichloro-phenylsulfanyl)-4-[5-(2-morpholin-4-yl-ethyl)-imidazol-1-ylmethyl]-benzonitrile
or a pharmaceutically acceptable salt thereof.

16. A pharmaceutical composition comprising a pharmaceutical carrier, and dispersed therein, a therapeutically effective amount of a compound of claim 1.

17. A pharmaceutical composition comprising a pharmaceutical carrier, and dispersed therein, a therapeutically effective amount of a compound of claim 5.

18. A pharmaceutical composition comprising a pharmaceutical carrier, and dispersed therein, a therapeutically effective amount of a compound of claim 10.

19. A method for inhibiting a prenyl-protein transferase which comprises administering to a mammal in need thereof a therapeutically effective amount of a composition of claim 16.

20. A method for inhibiting a prenyl-protein transferase which comprises administering to a mammal in need thereof a therapeutically effective amount of a composition of claim 17.

21. A method for inhibiting a prenyl-protein transferase which comprises administering to a mammal in need thereof a therapeutically effective amount of a composition of claim 18.

22. A method for treating cancer which comprises administering to a mammal in need thereof a therapeutically effective amount of a composition of claim 16.

23. A method for treating cancer which comprises administering to a mammal in need thereof a therapeutically effective amount of a composition of claim 17.

24. A method for treating cancer which comprises administering to a mammal in need thereof a therapeutically effective amount of a composition of claim 18.

25. A method for treating neurofibromen benign proliferative disorder which comprises administering to a mammal in need thereof a therapeutically effective amount of a composition of claim 16.

26. A method for treating blindness related to retinal vascularization which comprises administering to a mammal in need thereof a therapeutically effective amount of a composition of claim 16.

27. A method for treating infections from hepatitis delta and related viruses which comprises administering to a mammal in need thereof a therapeutically effective amount of a composition of claim 16.

28. A method for preventing restenosis which comprises administering to a mammal in need thereof a therapeutically effective amount of a composition of claim 16.

29. A method for treating polycystic kidney disease which comprises administering to a mammal in need thereof a therapeutically effective amount of a composition of claim 16.

30. A pharmaceutical composition made by combining the compound of claim 1 and a pharmaceutically acceptable carrier.

31. A process for making a pharmaceutical composition comprising combining a compound of claim 1 and a pharmaceutically acceptable carrier.

* * * * *

UNITED STATES PATENT AND TRADEMARK OFFICE
CERTIFICATE OF CORRECTION

PATENT NO. : 6,297,239 B1
DATED : October 2, 2001
INVENTOR(S) : S. Jane deSolms, John H. Hutchinson, Anthony W. Shaw, Samuel L. Graham and Terrence M. Ciccarone It is certified that error appears in the above-identified patent and that said Letters Patent is hereby corrected as shown below:

Column 95,
Line 33 should read as follows -- $OC(O)(C_1-C_6 \text{ alkyl})$, $-C_1-C_6 \text{ alkyl})N(R^8)_2$, and -- .

Column 96,
Line 64 should read as follows -- i) $R^9S(O)_q$-, -- .

Column 102,
The structure between lines 22-28 should read:

Column 105,
Line 58, the first word should read as follows -- imidazol -- .

Column 107,
At the end of line 31 insert the following -- ; -- .

Signed and Sealed this

Fourteenth Day of May, 2002

*Attest:*

*Attesting Officer*

JAMES E. ROGAN
*Director of the United States Patent and Trademark Office*

SEQUENCE LISTING

<160> NUMBER OF SEQ ID NOS: 26

<210> SEQ ID NO 1
<211> LENGTH: 4
<212> TYPE: PRT
<213> ORGANISM: Homosapien

<400> SEQUENCE: 1

Cys Val Ile Met
1

<210> SEQ ID NO 2
<211> LENGTH: 4
<212> TYPE: PRT
<213> ORGANISM: Homosapien

<400> SEQUENCE: 2

Cys Val Leu Leu
1

<210> SEQ ID NO 3
<211> LENGTH: 4
<212> TYPE: PRT
<213> ORGANISM: Homosapien

<400> SEQUENCE: 3

Cys Val Val Met
1

<210> SEQ ID NO 4
<211> LENGTH: 4
<212> TYPE: PRT
<213> ORGANISM: Homosapien

<400> SEQUENCE: 4

Cys Ile Ile Met
1

<210> SEQ ID NO 5
<211> LENGTH: 4
<212> TYPE: PRT
<213> ORGANISM: Homosapien

<400> SEQUENCE: 5

Cys Leu Leu Leu
1

<210> SEQ ID NO 6
<211> LENGTH: 4
<212> TYPE: PRT
<213> ORGANISM: Homosapien

<400> SEQUENCE: 6

Cys Gln Leu Leu
1

<210> SEQ ID NO 7
<211> LENGTH: 4
<212> TYPE: PRT
<213> ORGANISM: Homosapien

<400> SEQUENCE: 7

Cys Ser Ile Met
1

<210> SEQ ID NO 8
<211> LENGTH: 4
<212> TYPE: PRT
<213> ORGANISM: Homosapien

<400> SEQUENCE: 8

Cys Ala Ile Met

-continued

```
<210> SEQ ID NO 9
<211> LENGTH: 4
<212> TYPE: PRT
<213> ORGANISM: Homosapien

<400> SEQUENCE: 9

Cys Lys Val Leu
 1

<210> SEQ ID NO 10
<211> LENGTH: 4
<212> TYPE: PRT
<213> ORGANISM: Homosapien

<400> SEQUENCE: 10

Cys Leu Ile Met
 1

<210> SEQ ID NO 11
<211> LENGTH: 4
<212> TYPE: PRT
<213> ORGANISM: Homosapien

<400> SEQUENCE: 11

Cys Val Leu Ser
 1

<210> SEQ ID NO 12
<211> LENGTH: 4
<212> TYPE: PRT
<213> ORGANISM: Homosapien

<400> SEQUENCE: 12

Cys Ala Ile Leu
 1

<210> SEQ ID NO 13
<211> LENGTH: 15
<212> TYPE: PRT
<213> ORGANISM: Homosapien

<400> SEQUENCE: 13

Gly Lys Lys Lys Lys Lys Ser Lys Thr Lys Cys Val Ile Met
 1               5                  10                  15

<210> SEQ ID NO 14
<211> LENGTH: 86
<212> TYPE: DNA
<213> ORGANISM: Artificial Sequence
<220> FEATURE:
<223> OTHER INFORMATION: completely synthesized

<400> SEQUENCE: 14
tctcctcgag gccaccatgg ggagtagcaa gagcaagcct aaggacccca gccagcgccg     60
gatgacagaa tacaagcttg tggtgg                                         86

<210> SEQ ID NO 15
<211> LENGTH: 33
<212> TYPE: DNA
<213> ORGANISM: Artificial Sequence
<220> FEATURE:
<223> OTHER INFORMATION: completely synthesized
```

```
<400> SEQUENCE: 15
cacatctaga tcaggacagc acagacttgc agc                            33

<210> SEQ ID NO 16
<211> LENGTH: 41
<212> TYPE: DNA
<213> ORGANISM: Artificial Sequence
<220> FEATURE:
<223> OTHER INFORMATION: completely synthesized

<400> SEQUENCE: 16
tctcctcgag gccaccatga cagaatacaa gcttgtggtg g                   41

<210> SEQ ID NO 17
<211> LENGTH: 38
<212> TYPE: DNA
<213> ORGANISM: Artificial Sequence
<220> FEATURE:
<223> OTHER INFORMATION: completely synthesized

<400> SEQUENCE: 17
cactctagac tggtgtcaga gcagcacaca cttgcagc                       38

<210> SEQ ID NO 18
<211> LENGTH: 38
<212> TYPE: DNA
<213> ORGANISM: Artificial Sequence
<220> FEATURE:
<223> OTHER INFORMATION: completely synthesized

<400> SEQUENCE: 18
gagagaattc gccaccatga cggaatataa gctggtgg                       38

<210> SEQ ID NO 19
<211> LENGTH: 33
<212> TYPE: DNA
<213> ORGANISM: Artificial Sequence
<220> FEATURE:
<223> OTHER INFORMATION: completely synthesized

<400> SEQUENCE: 19
gagagtcgac gcgtcaggag agcacacact tgc                            33

<210> SEQ ID NO 20
<211> LENGTH: 22
<212> TYPE: DNA
<213> ORGANISM: Artificial Sequence
<220> FEATURE:
<223> OTHER INFORMATION: completely synthesized

<400> SEQUENCE: 20
ccgccggcct ggaggagtac ag                                        22

<210> SEQ ID NO 21
<211> LENGTH: 38
<212> TYPE: DNA
<213> ORGANISM: Artificial Sequence
<220> FEATURE:
<223> OTHER INFORMATION: completely synthesized

<400> SEQUENCE: 21
gagagaattc gccaccatga ctgagtacaa actggtgg                       38

<210> SEQ ID NO 22
<211> LENGTH: 32
```

```
<212> TYPE: DNA
<213> ORGANISM: Artificial Sequence
<220> FEATURE:
<223> OTHER INFORMATION: completely synthesized

<400> SEQUENCE: 22
gagagtcgac ttgttacatc accacacatg gc                              32

<210> SEQ ID NO 23
<211> LENGTH: 21
<212> TYPE: DNA
<213> ORGANISM: Artificial Sequence
<220> FEATURE:
<223> OTHER INFORMATION: completely synthesized

<400> SEQUENCE: 23
gttggagcag ttggtgttgg g                                          21

<210> SEQ ID NO 24
<211> LENGTH: 38
<212> TYPE: DNA
<213> ORGANISM: Artificial Sequence
<220> FEATURE:
<223> OTHER INFORMATION: completely synthesized

<400> SEQUENCE: 24
gagaggtacc gccaccatga ctgaatataa acttgtgg                        38

<210> SEQ ID NO 25
<211> LENGTH: 36
<212> TYPE: DNA
<213> ORGANISM: Artificial Sequence
<220> FEATURE:
<223> OTHER INFORMATION: completely synthesized

<400> SEQUENCE: 25
ctctgtcgac gtatttacat aattacacac tttgtc                          36

<210> SEQ ID NO 26
<211> LENGTH: 24
<212> TYPE: DNA
<213> ORGANISM: Artificial Sequence
<220> FEATURE:
<223> OTHER INFORMATION: completely synthesized

<400> SEQUENCE: 26
gtagttggag ctgttggcgt aggc                                       24
```